(12) United States Patent
Ochoa et al.

(10) Patent No.: US 10,253,366 B2
(45) Date of Patent: *Apr. 9, 2019

(54) DISCRIMINATION OF BLOOD TYPE VARIANTS

(71) Applicant: Progenika Biopharma S.A., Derio (ES)

(72) Inventors: Jorge Ochoa, Derio (ES); Monica Lopez, Derio (ES); Araitz Molano, Derio (ES); Diego Tejedor, Derio (ES); Antonio Martinez, Derio (ES)

(73) Assignee: Progenika Biopharma, S.A., Derio (ES)

( * ) Notice: Subject to any disclaimer, the term of this patent is extended or adjusted under 35 U.S.C. 154(b) by 367 days.

This patent is subject to a terminal disclaimer.

(21) Appl. No.: 15/142,881

(22) Filed: Apr. 29, 2016

(65) Prior Publication Data
US 2016/0244830 A1    Aug. 25, 2016

Related U.S. Application Data

(63) Continuation of application No. 13/791,284, filed on Mar. 8, 2013, now Pat. No. 9,359,643.

(51) Int. Cl.
*C12Q 1/68* (2018.01)
*C12Q 1/6881* (2018.01)

(52) U.S. Cl.
CPC ..... *C12Q 1/6881* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS 5,846,727 A * 12/1998 Soper ............... B01J 19/0093
                                                435/6.12
2012/0172239 A1   7/2012 Ochoa et al.

FOREIGN PATENT DOCUMENTS

| EP | 1780217 | 5/2007 |
|---|---|---|
| EP | 2471949 | 7/2012 |
| WO | WO 01/77384 | 10/2001 |
| WO | WO 02/38594 | 5/2002 |
| WO | WO 2012/171990 | 12/2012 |

OTHER PUBLICATIONS

Genbank Accession No. HF536496 (NCBI, NLM, Nov. 26, 2012).*
Genbank, NCBI Reference Sequence: NG_007494.1, version GI: 171184448, 2013 (19 pages).
Genbank, NCBI Reference Sequence: NG_009208.2, version GI: 301336136, 2013 (19 pages).
International Search Report and Written Opinion for International Application No. PCT/EP2014/052411, dated Apr. 10, 2014 (14 pages).
NEB Catalog, pp. 121, 284, 1998/1999.
Pham et al., "Heterogeneous molecular background of the weak C, VS+, $hr^B$-, $Hr^B$-phenotype in black persons," *Transfusion*, vol. 49, pp. 495-504, 2009.
Sala et al., "Analysis of the Protein S Gene in Protein S Deficiency," *Methods in Molecular Medicine*, vol. 31, pp. 249-268, 1999.
Silvy et al., "Identification of novel polymorphism restricted to the $(C)ce^s$ type 1 haplotype avoids risk of transfusion deadlock in SCD patients," *Br. J. Haematol*, vol. 160, pp. 863-867, 2013 (including 2 pages of Supporting Information).
Tax et al., "RHC and RHc genotyping in different ethnic groups," *Transfusion*, vol. 42, pp. 634-644, 2002.
Westhoff et al., "DIIIa and DIII Type 5 are encoded by the same allele and are associated with altered RHCE*ce alleles: clinical implications," *Transfusion*, vol. 50, pp. 1303-1311, 2010 (Author manuscript version, 17 pages).

* cited by examiner

*Primary Examiner* — Jehanne S Sitton
(74) *Attorney, Agent, or Firm* — Klarquist Sparkman, LLP

(57) ABSTRACT

The present invention provides a method for detecting the presence or absence of, or for discriminating between, blood type variants, including RHD*r's, RHD*DIIIa and RHD*DIVa-2. The method comprises amplifying by PCR a sample obtained from a human subject at intron 3 of the RHD gene locus. The invention also provides products, in particular, probes, primers and kits for use in the method of the invention.

17 Claims, 7 Drawing Sheets

Specification includes a Sequence Listing.

| | RHD | | | RHCE | | RHD | Serology |
|---|---|---|---|---|---|---|---|
| | presence or absence of an RHD/RHCE hybrid exon 3 allele | exon 4 (position 602) | exon 7 (position 1048) | presence/absence of an RHCE*C allele | exon 7 (position 1006) | intron 3 at position 3100 | |
| r's | presence | G | C | absence | T | G | C+w |
| DIIIa | presence | G | G | absence | G or T | A | C- |
| DIVa | presence | C | C | absence | G | A | C- |
| New variant | presence | G | G | absence | G | G | C- |

Figure 3

```
              3010       3020       3030       3040       3050
RHD      TTATTCCCAA GGCAAATATG GAAATTTGAT CATGTACTAA TCATAATAAA
RHCE*ce  .......... .......... ...G...... ....A.G... ......C...
r's      .......... .......... .:::::::::.:::::::::. :::::::-...
DIVa     .......... .......... ...A...... ....G.A... ......A...
DIIIa    .......... .......... ...A...... ....G.A... ......A...
#425     .......... .......... ...A...... ....G.A... ......A...

3060       3070       3080       3090       3100
RHD      GCTGGATTCT CTTTAAGAGA TTGAGAAATT AAAAGGCAAA AGCTGATATA
RHCE*ce  .......... .......... .......... .......... .........A
r's      .......... .......... .......... .......... .........G
DIVa     .......... .......... .......... .......... .........A
DIIIa    .......... .......... .......... .......... .........A
425     .......... .......... .......... .......... .........G 3110       3120       3130       3140       3150
RHD      TCATGTTTAG TTATATTGTG AGTCTTATAA GAAGCTGGGA GGCAACCCCA
RHCE*ce  .......... .....C.... .......... .......... ..........
r's      .......... .....T.... .......... .......... ..........
DIVa     .......... .....T.... .......... .......... ..........
DIIIa    .......... .....T.... .......... .......... ..........
#425     .......... .....T.... .......... .......... ..........

3160       3170       3180       3190       3200
RHD      TTAACTCACC AGAATACAGA ACTCAGTCTC ACAACTTACA TATAATTCCT
RHCE*ce  .......... .......... .......... .........A ..........
r's      .......... .......... .......... ........:: ::::::::::
DIVa     .......... .......... .......... .........G ..........
DIIIa    .......... .......... .......... .........G ..........
#425     .......... .......... .......... .........G ..........

3210       3220       3230       3240       3250
RHD      CTCAAACCTT TTCCTCAAAG ATTAAATTCT GAAAATAATC TTGTGATTAA
RHCE*ce  .......... .......... -......... .......... ..........
r's      :::::::::: ...... -......... .......... ..........
DIVa     .......... .......... A......... .......... ..........
DIIIa    .......... .......... A......... .......... ..........
#425     .......... .......... A......... .......... ..........

RHD      (SEQ ID NO: 29)
RHCE*ce  (SEQ ID NO: 30)
r's      (SEQ ID NO: 31)
DIVa     (SEQ ID NO: 29)
DIIIa    (SEQ ID NO: 29)
#425     (SEQ ID NO: 32)
```

Figure 7

DISCRIMINATION OF BLOOD TYPE VARIANTS

CROSS REFERENCE TO RELATED APPLICATION

This claims the benefit of U.S. application Ser. No. 13/791,284, filed Mar. 8, 2013, which is incorporated herein by reference in its entirety.

FIELD OF THE INVENTION

The invention relates to methods for genotyping and blood cell antigen determination, which in particular may discriminate the RHD*r's or RHD*r's-like blood type variants, which encode $C^{+W}$ antigen and no D antigen, from RHD*DIIIa, RHD*DIVa-2 and other blood type variants. The invention also relates to products, in particular, probes, primers and kits for use in such methods.

BACKGROUND TO THE INVENTION

The success of blood transfusion often depends on the degree of compatibility between donor and recipient. The degree of compatibility, in turn, is a function of the similarity in Red Blood Cell (RBC) antigen content between donor and recipient. Expression of many RBC antigens in an individual can be predicted from the analysis of their genomic DNA. Therefore, analysis of donor and/or recipient DNA can be used to facilitate blood matching and thus enable proper blood transfusion practice.

Hemolytic reactions are more common in multi-transfused than in singly transfused individuals, not only because of the increased probability of such an event as the number of transfused units increases, but also because of the accumulative nature of the immune response in the recipient. An example of a condition whose treatment includes repeated blood transfusions is Sickle Cell Disease (SCD). From the above follows that a high degree of compatibility with donor blood is often critical for the long-term success of transfusion in SCD patients.

While SCD is more prevalent among individuals of African ancestry, the blood donor population in the USA and other Western countries is largely Caucasian. As a consequence of this disparity, differences in RBC antigens between both racial groups often become responsible for blood transfusion failures in SCD patients.

The genetic variant RHD*DIIIa-CE(4-7)-D, also known as RHD-CE-D$^s$, RHD-CE(4-7)-D, (C)ce$^s$, or r$^s$, (RHD*r$^s$ henceforth) can be found in up to 5-10% of the African-American population, but is extremely rare in Caucasians. This variant poses a special challenge to blood transfusion because it encodes a rather complex antigen profile, which includes absence of D antigen, altered forms of C ($C^{+W}$) and e antigens, expression of low-frequency VS antigen, no expression of V antigen, and absence of the high-frequency hr$^B$ antigen. Among them, D and C antigens are the clinically most relevant ones.

The antigenic complexity of RHD*r$^s$ correlates with its genetic complexity, which includes a substitution of part of RHD exon 3, RHD exons 4-7, and the intervening introns by their RHCE counterparts, a G>T substitution at position 186 (exon 2), a C>T substitution at position 410 (hybrid exon 3), a C>G substitution at position 733 (exon 5), and a G>T substitution at position 1006 (exon 7). In addition to the changes in the RHD gene, RHD*r$^s$ occurs in cis with RHCE*ce$^s$1006T, an RHCE gene that also encodes substitutions C>G at position 733 (exon 5) and G>T at position 1006 (exon 7).

To add to the antigenic and genetic complexity, knowledge about the molecular basis of RHD*r$^{ts}$ is incomplete. For instance, the precise points of RHCE/RHD recombination have not been reported to date. Furthermore, two types of RHD*r$^{ts}$ variant have been described and named Type 1 and Type 2, which differ not only in their genetic composition but also in their antigen profiles.

Several publications (Westhoff et al., Transfusion (2010), 50: 1303-1311, Pham et al., Transfusion (2009), 49: 495-504, and Tax et al., Transfusion (2002) 42: 6234-6644) have uncovered the genetic similarity between RHD*r$^{ts}$ and other RHD variants, in particular RHD*DIIIa and RHD*DIVa/RHD*DIVa-2 (RHD*DIVa-2 henceforth). A number of molecular methods for the specific detection of RHD*r$^{ts}$ rely on the detection of polymorphisms located in D-CE hybrid exon 3 locus of RHD. These polymorphisms are now known to be shared with variants RHD*DIIIa and RHD*DIVa-2. Consequently, to date, identification of RHD*r$^{ts}$ in a sample by DNA analysis requires detection of hybrid exon 3 polymorphisms and discrimination from RHD*DIIIa and RHD*DIVa-2. This discrimination is clinically relevant since the latter variants encode a different antigen profile, which includes expression of partial D and absence of $C^{+W}$.

EP1780217 describes the detection of RHD positive haplotypes in D-negative individuals. Silvy et al., British Journal of Haematology, (2012 Dec. 30) doi: 10.1111/bjh. 12179 [Epub ahead of print], describe identification of a polymorphism said to be restricted to the (C)ce$^s$ type 1 haplotype. WO2012/171990 describes discrimination of blood type variants in a method making use of polymorphisms in intron 7 of the RHD gene and/or intron 7 of the RHCE gene. EP2471949 describes a method for the identification by molecular techniques of genetic variants that encode no D antigen (D$^-$) and altered C antigen ($C^{+W}$).

Antibody reagents commonly used to detect C antigen do not discriminate between $C^{+W}$ and $C^+$. Therefore, the phenotype is often reported as $C^+$. In cases where the antibody reagent does discriminate between $C^{+W}$ and $C^+$ but the sample contains a normal RHCE*C allele in trans to a RHD*r$^{ts}$ allele, $C^{+W}$ is obscured by $C^+$, resulting in a $C^+$ phenotype for the sample. Therefore, RHCE*C needs to be tested for and shown absent prior to assignment of a $C^{+W}$ phenotype to a sample. Accordingly, there remains a need for further methods for distinguishing RHD*r's from RHD*DIIIa and RHD*DIVa-2. The present invention addresses these and other objects.

SUMMARY OF THE INVENTION

The present inventors have surprisingly found that methods and, in particular, PCR primers as described herein are able to amplify a portion of intron 3 of the RHD gene found in r$^{ts}$ samples in a specific manner, and that this specificity is retained even under multiplex PCR conditions. Considerable disadvantages of previously-described primers and reaction methods are addressed by the methods and primers of the present invention, as demonstrated by the examples herein. The present invention mitigates false positive readings displayed by previously-described methods and primers, and is advantageously able to discriminate r$^{ts}$ from closely-related alleles, including a newly-described variant of RHD*DIIIa.

Accordingly, the present invention provides, in a first aspect, an oligonucleotide polymerase chain reaction (PCR) primer, the nucleotide sequence of which is of the formula:

X-Y-Z wherein:

X is $X_1$ or $X_2$, wherein:
  $X_1$ is the final n nucleotides in the nucleotide sequence ATATGGAAATTTGATCATGT (SEQ ID NO: 1), wherein n is a number between 0 and 20, inclusive; and
  $X_2$ is a variant of $X_1$ differing by no more than one nucleotide substitution;

Y is $Y_1$ or $Y_2$, wherein:
  $Y_1$ is the nucleotide sequence $AS_1TAATS_2ATAC$ (SEQ ID NO: 2), wherein $S_1$ and $S_2$ are independently selected from G and C; and
  $Y_2$ is a variant of $Y_1$ differing from $Y_1$ by no more than one nucleotide substitution, provided that said nucleotide substitution is not a substitution of the first A or final C of $Y_1$;

Z is the first m nucleotides in the nucleotide sequence TAAAG, wherein m is a number between 0 and 5, inclusive.

In some cases, the primer of this and other aspects of the invention is such that $X_1$ is the nucleotide sequence of AAATTTGATCATGT (SEQ ID NO: 3) or ATGT. That is to say, n may, in some cases, be 14 or 4. In certain cases, n may be 0, 1, 2, 3, 4, 5, 6, 7, 8, 9, 10, 11, 12, 13, 14, 15, 16, 17, 18, 19 or 20.

In some cases in accordance with this and other aspects of the present invention, $Y_1$ is selected from the group consisting of: ACTAATCATAC (SEQ ID NO: 4); ACTAATGATAC (SEQ ID NO: 5); and AGTAATCATAC (SEQ ID NO: 6). Preferably, if $S_1$ is G, $S_2$ is C. Likewise, if $S_1$ is C, $S_2$ is preferably G. Thus, the selection of $S_1$ and $S_2$ may be chosen to keep the number of mismatches with the intended target template sequence to not more than one nucleotide mismatch. However, it is specifically contemplated herein that the number of mismatches may be more than one. For example, in certain cases, both $S_1$ and $S_2$ may be G. Alternatively, the number of nucleotide mismatches may be zero. In certain cases, both $S_1$ and $S_2$ may be C.

In some cases in accordance with this and other aspects of the present invention, m is 0. Therefore, the primer of the invention may have no Z, with the result that the last nucleotide in Y (which is a C that corresponds to the C/A polymorphic nucleotide at position 3046 of RHD intron 3, as numbered in FIG. 7) is the 3' nucleotide of the primer of the invention. Alternatively, m may be 1, 2, 3, 4 or 5.

In some cases in accordance with this and other aspects of the present invention, the primer is not more than 30, 29, 28, 27, 26, 25, 24, 23, 22, 21 or 20 nucleotides in length. In some cases, the primer may be at least 10, 11, 12, 13, 14, 15, 16, 17, 18, 19, 20, 21, 22, 23, 24 or at least 25 nucleotides in length. In certain cases the primer may be between 10 and 30 nucleotides in length, such as between 15 and 25 nucleotides in length. Particular cases include a primer in accordance with the first aspect of the invention which has a length of exactly 10, 11, 12, 13, 14, 15, 16, 17, 18, 19, 20, 21, 22, 23, 24, 25, 26, 27, 28, 29 or 30 nucleotides.

In some cases in accordance with this and other aspects of the present invention, the primer may be DNA or RNA. The primer is preferably DNA.

In some cases in accordance with this and other aspects of the present invention, the primer may include one or more, e.g. 1, 2, 3, 4 or 5 altered or non-natural bases and/or derivatised or modified nucleotide bases. In particular, one or more bases (e.g. a 5' or a 3' base) may be biotinylated or conjugated to a detectable label. Alternatively or additionally, one or more bases (e.g. 1, 2, 3, 4 or 5 nucleotide bases) may be locked nucleic acid (LNA) bases.

In some cases in accordance with this and other aspects of the present invention, the nucleotide sequence of the primer consists of a nucleotide sequence selected from the group consisting of:

(i)
                                          (SEQ ID NO: 7)
AAATTTGATCATGTACTAATCATAC;

(ii)
                                          (SEQ ID NO: 8)
ATGTACTAATCATAC;

(iii)
                                          (SEQ ID NO: 9)
AAATTTGATCATGTACTAATGATAC;
and (iv)
                                         (SEQ ID NO: 10)
AAATTTGATCATGTAGTAATCATAC.

In some cases in accordance with this and other aspects of the present invention, the primer is suitable for use as a forward PCR primer in a PCR amplification of a portion of the $r^{'s}$ allele of intron 3 of the RHD gene.

In a second aspect, the present invention provides a plurality of oligonucleotide primers comprising:
  (i) an oligonucleotide primer of the first aspect of the invention; and
  (ii) (a) a reverse primer that hybridises to a portion of intron 3 of $r^{'s}$, or its complement, which portion includes at least one position of single nucleotide polymorphism (SNP) that differs between $r^{'s}$ and RHD; or
  (b) one or more primers that hybridise to a region of the RHD gene and or the RHCE gene.

Preferably, said reverse primer (ii) (a) hybridises to the reverse complement of a portion of the $r^{'s}$ intron 3 sequence that is shown in FIG. 7 and which lies 3' of position 3050, as numbered in FIG. 7. In some cases in accordance with this and other aspects of the present invention said reverse primer hybridises to a portion of intron 3 of $r^{'s}$, or its complement, which portion includes the G/A polymorphism position 3189 of intron 3 of the RHD gene, said numbering being as shown in FIG. 7.

In some cases in accordance with the second aspect of the present invention, the plurality of primers comprises:
  (i) an oligonucleotide primer of the first aspect of the invention; and
  (ii) at least one primer selected from the group consisting of:
    (a) an oligonucleotide primer of between 26 and 30 nucleotides in length comprising the nucleotide sequence GGAAAAGGTTTGAGAGGAATTATATT (SEQ ID NO: 11) or a variant thereof differing by not more than 3 (e.g. not more than 2 or not more than 1) nucleotide substitutions from the nucleotide sequence of SEQ ID NO: 11, provided that said substitutions do not include substitution of the final T in the nucleotide sequence of SEQ ID NO: 11;
    (b) an oligonucleotide primer consisting of the nucleotide sequence GGAAAAGGTTTGAGAGGAATTATATT (SEQ ID NO: 11);
    (c) the RHCE c forward primer consisting of the nucleotide sequence TGGGCTTCCTCACCTCAAA (SEQ ID NO: 12);

(d) the RHCE c reverse primer consisting of the nucleotide sequence TGATGACCACCTTCCCAGG (SEQ ID NO: 13);

(e) the RHCE C forward primer consisting of the nucleotide sequence GGCCACCACCATTTGAA (SEQ ID NO: 14);

(f) the RHCE C reverse primer consisting of the nucleotide sequence GGTAGCAGGCGTCTGTAAAAA (SEQ ID NO: 15);

(g) the RHCE exon 1 forward primer consisting of the nucleotide sequence CATAGACAGGCCAGCACAG (SEQ ID NO: 16);

(h) the RHCE exon 1 reverse primer consisting of the nucleotide sequence TGCCCCTGGAGAACCAT (SEQ ID NO: 17);

(i) the RHCE exon 5 forward primer consisting of the nucleotide sequence AAATTAAAATAAGCATTTGACCATC (SEQ ID NO: 18);

(j) the RHCE exon 5 reverse primer consisting of the nucleotide sequence CCTGAGATGGCTGTCACCAC (SEQ ID NO: 19);

(k) the RHCE exon 7 forward primer consisting of the nucleotide sequence ACATGCCATTGCCGTTC (SEQ ID NO: 20); and (l) the RHCE exon 7 reverse primer consisting of the nucleotide sequence TCTCACCTGCCAATCTGCT (SEQ ID NO: 21).

In some cases the plurality of oligonucleotide primers comprise at least:
an oligonucleotide primer of the first aspect of the invention, and
an oligonucleotide primer of between 26 and 30 nucleotides in length comprising the nucleotide sequence GGAAAAGGTTTGAGAGGAATTATATT (SEQ ID NO: 11) or a variant thereof differing by not more than 3 (e.g. not more than 2 or not more than 1) nucleotide substitutions from the nucleotide sequence of SEQ ID NO: 11, provided that said substitutions do not include substitution of the final T in the nucleotide sequence of SEQ ID NO: 11.

In some cases the plurality of oligonucleotide primers comprise at least the primer pair:

```
                                        (SEQ ID NO: 7)
AAATTTGATCATGTACTAATCATAC;
and (SEQ ID NO: 11)
GGAAAAGGTTTGAGAGGAATTATATT.
```

In a third aspect the present invention provides a kit for assessing a subject's blood type, said kit comprising:
a plurality of primers of the second aspect of the invention;
optionally, one or more probes and/or primers that span one or more polymorphic positions in intron 3, exon 3, exon 4, intron 7 and/or exon 7 of the RHD gene locus; and/or
optionally, one or more probes and/or primers that span one or more polymorphic positions in exon 7 of the RHCE gene locus.

In a fourth aspect, the present invention provides a system for use in determining a subject's blood type, the system comprising:
a kit of the third aspect of the invention; and
at least one detector arranged to detect a signal from detectably labelled DNA obtained from said subject or a detectably labelled amplicon produced by PCR amplification carried out on DNA obtained from said subject;
at least one controller in communication with the at least one detector, the controller being programmed with computer-readable instructions to transform said signal into predicted blood type haplotypes, and optionally, to transform said predicted blood type haplotypes into a predicted blood type phenotype.

In a fifth aspect the present invention provides a method for determining the presence or absence of, or for discriminating between, blood type alleles in a DNA-containing sample, which method comprises amplification by polymerase chain reaction (PCR) of at least a portion of intron 3 of the RHD gene, wherein said PCR employs at least a forward primer and a reverse primer each capable of hybridising to the $r^s$ sequence set forth in SEQ ID NO: 31 (FIG. 7), or its complement, and wherein said forward primer is the primer of the first aspect of the invention.

In some cases in accordance with the method of this and other aspects of the invention, the blood type alleles are alleles that comprise an RHD/RHCE hybrid exon 3. In particular, the blood type alleles may be selected from the group consisting of: RHD*$r^s$; RHD*$r^s$-like; RHD*$r^s$ Type 1; RHD*$r^s$ Type 2; RHD*DIIIa; RHD*DIIIa IVS3+3100G; RHD*DIII_FN; RHD*DIVa-2; RHD*DIVa; RHD*DIII-type4; RHD*DIII-type6; RHD*DIII-type7; RHD*DIII-type8; RHCE*$ce^s$; RHCE*$ce^s$1006T; RHCE*$ce^s$1006C; RHCE*ce733G; RHCE*ce48C,733G,1025T; RHCE*ce48C,697G,733G; RHCE*ce340T,733G; and RHCE*ce48C,733G,748A.

In some cases in accordance with the method of this and other aspects of the invention the PCR amplifies $r^s$, but does not amplify one or more of: RHD; RHCE*ce; RHD*DIIIa; RHD*DIIIa IVS3+3100G; and RHD*DIVa. In particular, said PCR may in certain cases amplify $r^s$, but not any of RHD; RHCE*ce; RHD*DIIIa; RHD*DIIIa IVS3+3100G; and RHD*DIVa.

In some cases in accordance with the method of this and other aspects of the invention the method is for discriminating $r^s$ from RHD*DIIIa IVS3+3100G. The ability to distinguish $r^s$ from the newly-described variant, "RHD*DIIIa IVS3+3100G", which as far as the present inventors are aware has not previously been reported, is a major advance. The newly-described variant, "RHD*DIIIa IVS3+3100G" comprises the same RHD intron 3 position 3100 A to G polymorphism that has previously been reported to be specific for $r^s$ (see Silvy et al., 2012). Reliance on the presence of the RHD intron 3 position 3100 A to G polymorphism to uniquely identify $r^s$ would be expected to result in false positive results. The provision of a method that discriminates $r^s$ from RHD*DIIIa IVS3+3100G is expected to provide a significant clinical contribution.

The method in accordance with this and other aspects of the present invention utilises a forward primer of the first aspect of the invention. Particular examples include a primer that consists of the nucleotide sequence AAATTTGATCATGTACTAATCATAC (SEQ ID NO: 7). The method further utilises a suitable reverse primer, which may be any reverse primer capable of yielding a PCR product when used in combination with the forward primer of the first aspect of the invention. In certain cases, the reverse primer is capable of hybridising to a portion of intron 3 of $r^s$, or its complement, which portion includes at least one position of single nucleotide polymorphism (SNP) that differs between $r^s$ and RHD. In a certain cases, said position of SNP comprises the G/A polymorphism at position 3189 of intron 3 of the RHD gene, said numbering being as shown in FIG. 7 (see also SEQ ID NO: 31). In some cases, the reverse primer is of between 26 and 30 nucleotides in length and comprises the nucleotide sequence GGAAAAGGTTTGAGAGGAATTATATT (SEQ ID NO: 11). In certain cases, the reverse primer consists of the nucleotide sequence GGAAAAGGTTTGAGAGGAAT-TATATT (SEQ ID NO: 11).

In some cases in accordance with the method of this and other aspects of the invention the PCR is multiplex PCR. The multiplex PCR may further comprise amplification of one or more RHD and/or RHCE gene segments other than RHD intron 3. In some cases, the one or more RHD and/or RHCE gene segments are selected from the group consisting of: RHCE c; RHCE C; RHCE exon 1; RHCE exon 5; and RHCE exon 7. Accordingly, the method may employ additional PCR primers to be used in multiplex with the above-described PCR primers. In certain cases, the multiplex PCR further comprises employing 1, 2, 3, 4, 5, 6, 7, 8, 9 or all 10 of the following primers:
 (i) the RHCE c forward primer consisting of the nucleotide sequence TGGGCTTCCTCACCTCAAA (SEQ ID NO: 12);
 (ii) the RHCE c reverse primer consisting of the nucleotide sequence TGATGACCACCTTCCCAGG (SEQ ID NO: 13);
 (iii) the RHCE C forward primer consisting of the nucleotide sequence GGCCACCACCATTTGAA (SEQ ID NO: 14);
 (iv) the RHCE C reverse primer consisting of the nucleotide sequence GGTAGCAGGCGTCTGTAAAAA (SEQ ID NO: 15);
 (v) the RHCE exon 1 forward primer consisting of the nucleotide sequence CATAGACAGGCCAGCACAG (SEQ ID NO: 16);
 (vi) the RHCE exon 1 reverse primer consisting of the nucleotide sequence TGCCCCTGGAGAACCAT (SEQ ID NO: 17);
 (vii) the RHCE exon 5 forward primer consisting of the nucleotide sequence AAATTAAAATAAGCATTT-GACCATC (SEQ ID NO: 18);
 (viii) the RHCE exon 5 reverse primer consisting of the nucleotide sequence CCTGAGATGGCTGTCACCAC (SEQ ID NO: 19);
 (ix) the RHCE exon 7 forward primer consisting of the nucleotide sequence ACATGCCATTGCCGTTC (SEQ ID NO: 20); and
 (x) the RHCE exon 7 reverse primer consisting of the nucleotide sequence TCTCACCTGCCAATCTGCT (SEQ ID NO: 21).

Preferably, the primers are employed in pairs, said primers being paired as follows: (i) with (ii); (iii) with (iv); (v) with (vi); (vii) with (viii); and (ix) with (x).

In some cases in accordance with the method of the present invention, the sample is a sample which has previously been determined to comprise an RHD-RHCE hybrid exon 3.

Alternatively, the sample may be suspected to comprise an RHD-RHCE hybrid exon 3 or be an unknown sample. The method may therefore further comprise a preceding step of determining whether the sample contains an RHD-RHCE hybrid exon 3.

In some cases in accordance with the method of the present invention, the method further comprises determining the presence or absence of an RHCE*C allele in the sample. In some cases the method further comprises genotyping the sample at one or more positions of polymorphisms in the RHD and/or RHCE gene loci. In certain cases, the method comprises genotyping the sample at position 410 of the RHD exon 3. In certain cases, the method comprises genotyping the sample at position 602 of the RHD exon 4. In certain cases, method comprises genotyping the sample at position 1048 of the RHD exon 7. In certain cases, the method comprises genotyping the sample at position 1006 of the RHCE exon 7. In certain cases, the method comprises genotyping the sample at position 3100 of the RHD intron 3.

In some cases in accordance with the method of the present invention, the method comprises genotyping not more than 50, 40, 30, 25, 20, 15, or not more than 10, single nucleotide polymorphic positions in the RHD gene locus and/or the RHCE gene locus.

In some cases in accordance with the method of the present invention, the method further comprises predicting an RHD phenotype and/or an RHCE phenotype for the subject based on, at least, the degree of amplification by PCR of said at least one portion of intron 3 of the RHD gene. This may, for example, include a visual or computer-aided inspection of the intensity of a band on a gel where the intensity is related to the degree of amplification of the PCR product. The skilled person will of course be readily able to make us of suitable techniques to evaluate the degree of PCR amplification, e.g., for classification of a sample as containing $r^{’s}$. Such techniques include, without limitation, real time PCR (qPCR), Luminex bead-based detection and agarose gel-based evaluation. The method may comprise detecting a positive result for $r^{’s}$-specific PCR amplification and thereby classifying a sample as containing an $r^{’s}$ allele. In some cases, the phenotype prediction is further based on:
 (i) the presence or absence of an RHD/RHCE hybrid exon 3;
 (ii) the identity of one or both alleles present at position 602 of the RHD exon 4;
 (iii) the identity of one or both alleles present at position 1048 of the RHD exon 7;
 (iv) the presence or absence of an RHCE*C allele in the RHCE gene locus;
 (v) the identity of one or both alleles present at position 1006 of the RHCE exon 7; and/or
 (vi) the identity of one or both alleles present at position 3100 of the RHD intron 3.

In some cases the sample is found to contain $r^{’s}$ and is therefore predicted to have $C^{+W}$ serology.

In accordance with this and other aspects of the present invention, the sample is preferably obtained or has been previously obtained from a human subject. In some cases the subject is undergoing, or is a candidate for, blood transfusion or bone marrow transplantation. In some cases the subject has sickle cell disease (SCD) or Thalassemia major. In some cases the subject has non-Caucasian ancestry. In some cases, the subject has African ancestry.

In accordance with this and other aspects of the present invention, the sample may be any suitable biological sample from which it is possible to obtain nucleic acid, particularly genomic DNA, for use in a PCR reaction. Suitable samples include any material of bodily origin (liquid, solid or aspirate) such as blood, hair, cheek cells and skin cells.

In accordance with this and other aspects of the present invention, the sample may be subjected to one or more treatments to extract a nucleic acid prior to or as part of said amplification by PCR.

In accordance with this and other aspects of the present invention, the method may comprise Allele-Specific Polymerase Chain Reaction (ASP).

In accordance with this and other aspects of the present invention, the method may comprise labelling a nucleic acid obtained from the sample or labelling the amplicon produced by said PCR amplification.

In accordance with this and other aspects of the present invention, the method may further comprise carrying out serological analysis on a blood sample that has been obtained from the subject. This may be particularly useful to corroborate or clarify a phenotype prediction made. Combining the genotype-based prediction of blood type with a serological-based prediction may be useful, e.g., to improve accuracy or to resolve ambiguous results. However, it is also specifically contemplated herein that the method of this and other aspects of the present invention may not comprise carrying out serological analysis. Removing the need to carry out serological analysis provides considerable savings in terms of time, cost and/or resources.

In a sixth aspect the present invention provides a method of blood matching, the method comprising:

carrying out the method of the fifth aspect of the invention on a recipient sample from a recipient subject in need of donor blood and on a donor sample from a potential donor subject;

comparing the blood type alleles present in the recipient sample with those present in the donor subject and thereby determining the compatibility of the recipient subject to receive blood from the potential donor subject.

In accordance with the present invention, the subject may be undergoing, or may be a candidate for, blood transfusion. In some cases, the subject may have SCD, or any other disease requiring repeated blood transfusions, such as Thalassemia major or certain blood cell malignancies.

In accordance with the present invention, the subject may be of non-Caucasian race. In particular, the subject may be of African ancestry (e.g. "Black persons"). In certain cases, the subject may have an ancestral origin in a Mediterranean country.

In accordance with the method of the invention, the sample may be any suitable biological sample from which it is possible to amplify at least a portion of intron 3 of the RHD gene locus and/or from which it is possible to determine the genotype of the subject at one or more polymorphic positions in the RHD gene and/or the RHCE gene. In certain case, the sample may conveniently take the form of a blood sample.

In certain cases in accordance with the method of the invention, the method may comprise carrying out an Allele-Specific Polymerase Chain Reaction (ASP) and/or Allele-Specific Hybridization (ASH).

In certain cases in accordance with the method of this and other aspects of the invention, the method may comprise labelling a nucleic acid obtained from the sample or labelling an amplicon derived from a nucleic acid obtained from the sample. The label is preferably a detectable label. In some cases, DNA derived from the sample, e.g. PCR product resulting from use of the DNA from the sample as template, may be labelled using a fluorescent label or dye (e.g. by conjugating said fluorescent label or dye to the PCR product before or after fragmentation of the PCR product).

In some cases, the method in accordance with the sixth aspect of the invention may be carried out for a plurality of recipient subjects and a plurality of potential donor subjects.

The invention will now be described in more detail, by way of example and not limitation, by reference to the accompanying drawings. Many equivalent modifications and variations will be apparent to those skilled in the art when given this disclosure. Accordingly, the exemplary embodiments of the invention set forth are considered to be illustrative and not limiting. Various changes to the described embodiments may be made without departing from the scope of the invention. All documents cited herein are expressly incorporated by reference.

DESCRIPTION OF THE FIGURES

FIG. 3 shows a table of certain RHD and RHCE exon and intron features for $r^s$, DIIIa, DIVa and the new variant "RHD*DIIIa IVS3+3100G";

FIG. 7 shows an alignment of a portion of intron 3 of the RHD gene numbered positions 3001 to 3250, numbered according to the RHD sequence (upper row). An identical nucleotide to that above is represented by a dot; an omitted/deleted nucleotide (i.e., a gap) is represented by a dash. The sequences shown are (from top to bottom): RHD, RHCE*ce, $r^s$, DIVa, DIIIa and the newly-described variant RHD*DIIIa IVS3+3100G (shown as #425). The locations of the reference forward primer and reverse primer are indicated by shaded boxes.

SEQUENCE LISTING

Figure 1:
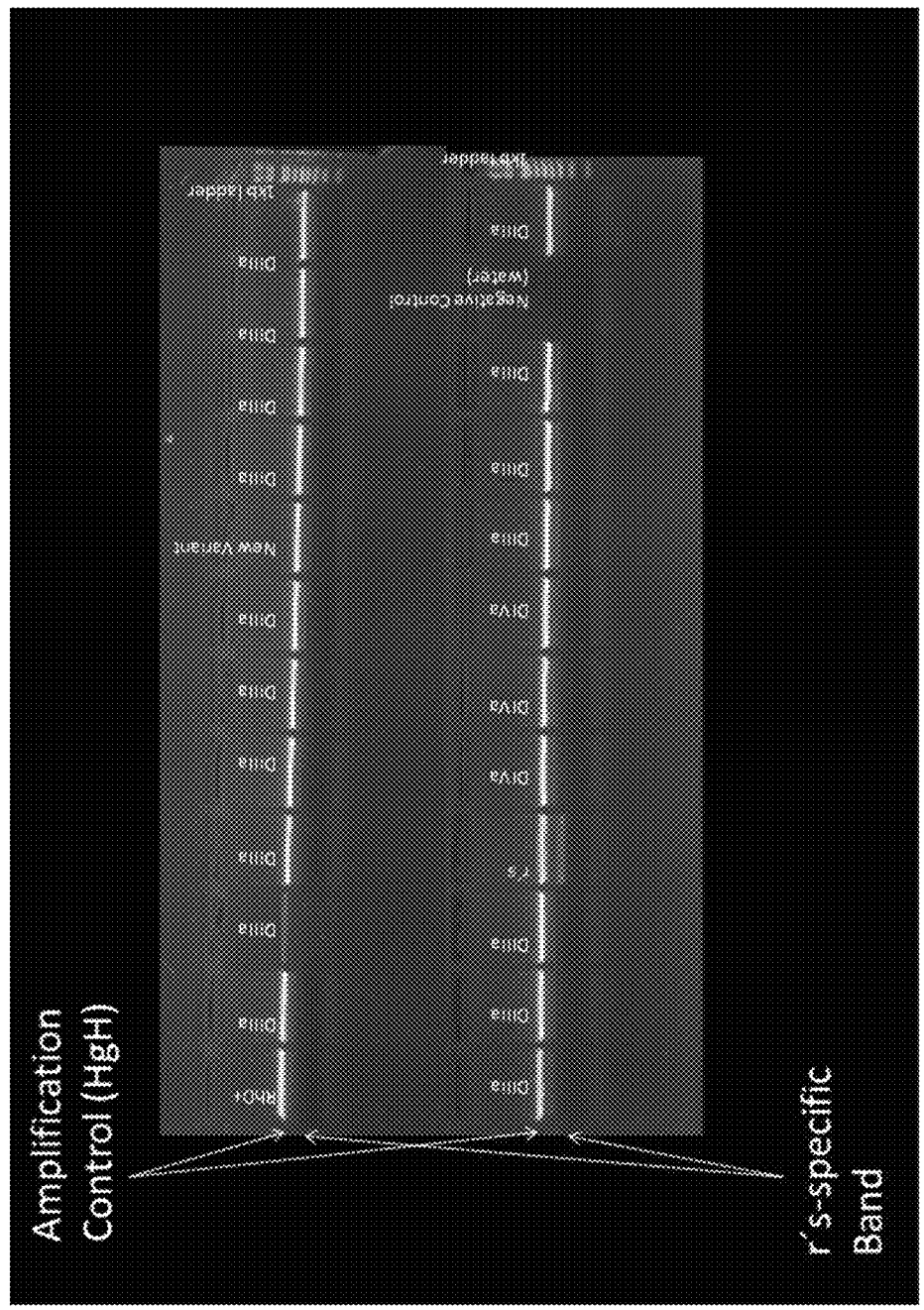
FIG. 1 shows a gel image depicting the PCR results of a reaction utilising primers for an amplification control (HgH) (upper band) and $r^s$ (lower band) for a variety of samples (including RhD$^+$, DIIIa, RHD*DIIIa IVS3+3100G, $r^s$, DIVa and a negative control.

The Sequence Listing is submitted as an ASCII text file in the form of the file named Sequence_Listing.txt, which was created on Apr. 28, 2016, and is 177,195 bytes, which is incorporated by reference herein.

DETAILED DESCRIPTION OF THE INVENTION

The present invention finds use in the determination of the clinically relevant RHD- and RHCE-encoded antigen phenotypes of a blood sample. The invention provides a method for detecting the presence or absence of, or for discriminating between, blood type variants, which method comprises amplification by polymerase chain reaction (PCR) of at least a portion of intron 3 of the RHD gene, wherein said PCR employs at least a forward primer and a reverse primer each capable of hybridising to the $r^s$ sequence set forth in SEQ ID NO: 31, or its complement, and wherein said forward primer nucleotide sequence is of the formula:

X-Y-Z wherein:

X is $X_1$ or $X_2$, wherein:
   $X_1$ is the final n nucleotides in the nucleotide sequence ATATGGAAATTTGATCATGT (SEQ ID NO: 1), wherein n is a number between 0 and 20, inclusive; and
   $X_2$ is a variant of $X_1$ differing by no more than one nucleotide substitution;

Y is $Y_1$ or $Y_2$, wherein:
   $Y_1$ is the nucleotide sequence $AS_1TAATS_2ATAC$ (SEQ ID NO: 2), wherein $S_1$ and $S_2$ are independently selected from G and C; and
   $Y_2$ is a variant of $Y_1$ differing from $Y_1$ by no more than one nucleotide substitution, provided that said nucleotide substitution is not a substitution of the first A or final C of $Y_1$;

Z is the first m nucleotides in the nucleotide sequence TAAAG, wherein m is a number between 0 and 5, inclusive.

Advantageously, the method of the present invention may further comprise determining the presence or absence of an RHD/RHCE hybrid exon 3 in said sample and/or genotyping a sample obtained from a human subject at one or more positions in intron 7 of the RHD gene and/or in intron 7 of the RHCE gene. Blood typing by making use of intron 7 polymorphisms is described in WO2012/171990, the entire contents of which is expressly incorporated herein by reference. Blood typing by making use of a combination of polymorphisms in the RHD gene and/or the RHCE gene are described in US2012/0172239 and EP2471949, the entire contents of which are both expressly incorporated herein by reference.

The Rh blood group D antigen is encoded by the RHD gene, which comprises 10 exons. The complete RHD gene sequence is available at NCBI Reference Sequence: NG_007494.1 No. NG_007494.1, GI:171184448, (SEQ ID NO: 22), the entire contents of which is incorporated herein by reference.

The Rh blood group C antigen is encoded by the RHCE gene, which comprises 10 exons. The complete RHCE gene sequence is available at NCBI Reference Sequence: NG_009208.2, GI:301336136, (SEQ ID NO: 23), the entire contents of which is incorporated herein by reference.

The term "sample" as used herein is intended to encompass any material (solid, liquid or aspirate) obtained directly or indirectly from a human subject and from which the identity of one or more nucleotides in a relevant genomic locus (e.g. intron 7 or the RHD locus and/or intron 7 of the RHCE locus) can be determined. In particular, the term "sample" includes any biological fluid such as blood, plasma, urine, saliva, cerebrospinal fluid and interstitial fluid, any solid matter, such as tissue, bone and hair, any cell or cell extract, any derived cell line, such as an immortalised tumour cell line and stem cell line, an extract of any of the preceding sample types, such as fixed or paraffin-embedded tissue. In certain preferred embodiments, the sample is an extract of human genomic DNA, optionally amplified and/or purified.

As used herein, the term "genotyping" is intended to encompass any method for determining the identity of the nucleotide at a particular position such as a polymorphic position at a specified locus. Thus, genotyping includes identifying one or both alleles of a particular gene. Genotyping may employ any of a variety of techniques, including but not limited to, allele-specific hybridisation, allele-specific PCR, sequencing of all or part of a gene.

Unless specified otherwise, all nucleic acid sequences, such as primer sequences, are set forth herein in the direct 5' to 3'. Thus, for example, the primer sequence AAATTT-GATCATGTACTAATCATAC (SEQ ID NO: 7) may equally be written as 5'-AAATTTGATCATGTACTAATCATAC-3' (SEQ ID NO: 7).

As described herein in detail, certain blood type alleles are less common and a typically referred to as "variants" (e.g. RHD*$r^s$). Variant blood type alleles are in some cases referred to herein simply as "blood type variants".

Broadly, the present invention provides methods and products for the identification by molecular techniques of genetic variants RHD*$r^s$ or RHD*$r^s$-like, which encode no D antigen (D⁻), an altered form of D antigen (partial D), altered forms of C ($C^{+W}$) and e antigens, expression of low-frequency VS antigen, no expression of V antigen, and/or no $hr^B$ antigen ($hr^{B-}$) in blood cells. The present inventors have found that amplification of a region of intron 3 of the RHD locus may be $r^s$-specific when primers as described in detail herein are employed. This $r^s$-specific amplification enables discrimination between variants RHD*$r^s$ or RHD*$r^s$-like and other RHD/RHCE hybrid exon 3 variants, including but not limited to RHD*DIIIa, RHD*DIIIa IVS3+3100G, RHD*DIII_FN and RHD*DIVa-2. In certain embodiments, the method of the invention provides considerable efficiency savings in comparison with, for example, full DNA sequencing, or genotyping of a large number of polymorphisms, or determining the phenotype by serological methods. Nevertheless, it is specifically contemplated that the method of the invention may, in some cases, involve DNA sequencing in order to genotype the sample obtained from the subject.

A wide variety of techniques are suitable and may be used in accordance with the present invention. Allele-specific oligonucleotides, for example, used in a competitive or non-competitive PCR (ASP henceforth), can also be used to detect genetic variants.

In accordance with any aspect of the present invention, functional segments or their portions may be amplified, for example by PCR, using as a template genomic DNA. Amplified functional segments or their portions can be labelled (e.g. with a fluorescent label) to allow for their detection, and optionally fragmented to facilitate their pairing with oligonucleotide probes.

In accordance with any aspect of the present invention, labelled and fragmented functional segments or their portions may be incubated under conditions that maximize the sensitivity and specificity of pairing with probes attached to the solid support. The presence of probe-paired functional segments or their portions may be determined indirectly from the measurement of label, usually a fluorochrome, attached to the solid support. This measurement is referred to herein as signal intensity. By way of example, the fluorescence emitted by the fluorochrome may be collected by means of a fluorescence detection device, such as a confocal scanner.

Examples

Discrimination among genetic variants that share a RHD/RHCE hybrid exon 3 but encode different forms of D Ag (Partial D Ag vs. No D Ag) and RhC Ag (Normal C Ag vs. Altered/Weakened C Ag, sometimes abbreviated as $C^{+W}$)

The following example relates to a method of discriminating among RHD/RHCE hybrid exon 3 variants RHD*$r^s$, RHD*DIIIa and RHD*DIVa-2 and a newly-discovered variant designated herein as "RHD*DIIIa IVS3+3100G".

Genomic DNA was extracted from nucleated cells in a blood sample by cell lysis. Extracted DNA was purified on an affinity column. Both, cell lysis and DNA purification are performed with a QIAamp® Blood kit (Qiagen, Germany) by following manufacturer protocols and recommendations. Purity of DNA was determined by spectrophotometry on a Nanodrop™ instrument (Nanodrop, DE). Only DNA solutions with an $OD_{260}/OD_{280}$ 1.8±0.2 proceeded to subsequent analysis.

$r^{\prime s}$-Specific PCR Amplification

Purified DNA was used as a template for multiplexed Polymerase Chain Reaction (PCR) amplification of the gene segments of interest in a GeneAmp® 9700 thermal cycler (Perkin-Elmer, CA). Primer sequences were as follows (5'-3'):

TABLE 1

| $r^{\prime s}$ | Forward | AAATTTGATCATGTACTAATCATAC | SEQ ID NO: 7 |
| | Reverse | GGAAAAGGTTTGAGAGGAATTATATT | SEQ ID NO: 11 |

Cycling conditions consist of a denaturation/polymerase activation step at 95° C. for 15 min, followed by 40 cycles of denaturation at 95° C. for 30 sec, annealing at 60° C. for 30 sec, extension at 72° C. for 80 sec, and a final extension step at 72° C. for 7 min.

Amplified DNA was separated by electrophoresis on a 2% agarose gel, stained with SYBR® Safe dye (Invitrogen, OR), and photographed under UV illumination. Amplification vs. no amplification of a segment was determined visually by a trained laboratory technician.

The following samples of known identity were subjected to allele-specific PCR using the above $r^{\prime s}$-specific primer pair: RhD$^+$ (one sample), DIIIa (17 samples), the newly-discovered variant "RHD*DIIIa IVS3+3100G" (one sample), $r^{\prime s}$ (one sample), DIVa (3 samples) and a water negative control (one sample). As a positive control for PCR amplification, primers for amplification of HgH were also employed. The PCR reaction products were run on an agarose gel (see FIG. 1).

As shown in FIG. 1, the upper band which indicates the presence of the HgH positive control PCR product is visible for all samples with the exception of the water negative control. The $r^{\prime s}$-specific band (lower band) is visible only on the $r^{\prime s}$ sample (lower panel; lane 4). These results clearly demonstrate that $r^{\prime s}$-specific PCR is able to discriminate between $r^{\prime s}$ and other RHD/RHCE hybrid exon 3 variants such as DIIIa, DIVa and the newly-discovered variant "RHD*DIIIa IVS3+3100G".

Multiplex PCR and Probe-Based Genotyping

The following primers (5'-3') were used in multiplex with the $r^{\prime s}$ primers described above:

TABLE 2

| RHCE c | Forward | TGGGCTTCCTCACCTCAAA | SEQ ID NO: 12 |
| | Reverse | TGATGACCACCTTCCCAGG | SEQ ID NO: 13 |
| RHCE C | Forward | GGCCACCACCATTTGAA | SEQ ID NO: 14 |
| | Reverse | GGTAGCAGGCGTCTGTAAAAA | SEQ ID NO: 15 |

TABLE 3

| RHCE Exon 1 | Forward | CATAGACAGGCCAGCACAG | SEQ ID NO: 16 |
| | Reverse | TGCCCCTGGAGAACCAT | SEQ ID NO: 17 |
| RHCE Exon 5 | Forward | AAATTAAAATAAGCATTTGACCATC | SEQ ID NO: 18 |
| | Reverse | CCTGAGATGGCTGTCACCAC | SEQ ID NO: 19 |
| RHCE Exon 7 | Forward | ACATGCCATTGCCGTTC | SEQ ID NO: 20 |
| | Reverse | TCTCACCTGCCAATCTGCT | SEQ ID NO: 21 |

The following probe sequence was used to determine the presence of absence of the intron 3 amplicon:

CAAAAGCTGATATGTCATGTTTAGTTA (SEQ ID NO: 24)

A single probe may be used to determine presence or absence of the intron 3 amplicon because the PCR is allele-specific (due to the design of the forward primer). In other words, it is not necessary for the detection probe itself to interrogate a sequence that is specific to $r^{\prime s}$.

As a non-limiting example, the procedure for Luminex® xMAP®-based detection employed herein, was as follows:

DNA Sample Preparation

Human genomic DNA was extracted from whole blood with EDTA as anti-coagulant. Genomic DNA extraction was carried out in the pre-PCR area.

Genomic DNA input was 100 ng. Genomic DNA purity ($OD_{260}/OD_{280}$ ratio) was in the 1.63-1.95 range.

Genomic DNA samples were stored frozen at −15 to −25° C. for up to one month. Multiple freeze/thaw cycles were avoided.

The following procedure was applied:

Procedure

The ID-CORE XT™ protocol consists of 4 steps:

Each batch of samples was processed with a negative control (molecular biology grade water that is known to be free of any DNA contamination).

I. Amplification

Work in the pre-PCR area and use aerosol-barrier tips. Use a new tip for each DNA sample.

Briefly vortex and spin tubes before use.

It is not necessary to set up the PCR reaction on ice.

1. Turn on the thermocycler.
2. Take the following reagents out of the refrigerator and freezer: ID-CORE XT™ PCR Master Mix and HotStarTaq® DNA polymerase, respectively.

Note: HotStarTaq® DNA polymerase must be removed from the freezer immediately before use and returned to the freezer immediately after use. Alternatively use ice or a microtube cooler. The stock enzyme should be mixed by gently flicking the tube.

3. Set up the ID-CORE XT™ PCR reaction mix as shown in the following table (all volumes in μL):

|  | Number of samples | | | |
|---|---|---|---|---|
|  | 1 | 8 | 24 | 48 |
| ID-CORE XT™ PCR Master Mix | 22.5 | 180 | 540 | 1080 |
| HotStarTaq® DNA Polymerase (5 U/μL) | 0.5 | 4 | 12 | 24 |

NOTE:
the stated volumes already include an excess to account for pipetting error.

4. Vortex and spin the ID-CORE XT™ PCR reaction mix.
5. Immediately dispense 20 μL per sample into the wells of a 96-well PCR plate.
6. Add 5 μL of sample DNA, positive control DNA and negative control to the appropriate wells in this order.
7. Seal the plate with the adhesive film.
   Work in the post-PCR area.
8. Spin down the PCR plate to collect the liquid at the bottom of the wells.
9. Verify that all wells are properly sealed and that the lid of the thermocycler has reached the pre-set temperature.
10. Place the plate in the thermocycler. Place the compression pad over the plate.
11. Close the thermocycler lid and start the ID XT PCR amplification program.

| | Temperature | Time | Cycles |
|---|---|---|---|
| Polymerase | 95° C. | 15 | 1 |
| Denaturation | 95° C. | 30 s | 40 |
| Annealing | 60° C. | 30 s | 40 |
| Extension | 72° C. | 80 s | 40 |
| Final | 72° C. | 7 min | 1 |
| Hold | 4° C. | ∞ | 1 |

Amplification reaction volume: 25 μL

II. Hybridization
Work in the post-PCR area. Use a new tip for each sample. Whenever necessary during dispensing steps, dry the surface of the Costar plate using a low-lint wipe.
Handling and Storage of the ID-CORE XT™ Beads Master Mix:
   a. Beads settle and aggregate with time. Before pipetting, bring them to a homogeneous suspension by vigorous vortexing for 30 seconds.
   b. During ID-CORE XT™ Beads Master Mix dispensing, keep beads in suspension by vortexing frequently (every 8 samples).
   c. Do not centrifuge the plate once the ID-CORE XT™ Beads Master Mix has been dispensed to avoid bead aggregation.
   d. Beads contain an internal fluorescent dye. To avoid photobleaching, protect them from light during storage and usage.
Luminex® System Preparation:
   a. Turn on the Luminex® 100/200™ system between 30 minutes and 4 hours before assaying the samples.
   b. Set the XYP instrument heater temperature at 52° C. and verify that the heater block is on the plate holder.
   c. Perform Luminex® 100/200™ daily startup maintenance.
1. Turn on the thermocycler.
2. Take the ID-CORE XT™ Beads Master Mix out of the refrigerator and let equilibrate to room temperature.
3. Vortex the ID-CORE XT™ Beads Master Mix for 30 seconds.
4. Dispense 46 μL of the ID-CORE XT™ Beads Master Mix into a Costar plate. Avoid bubble formation during dispensing.
5. Spin down the PCR plate to collect the liquid at the bottom of the wells.
6. Add 4 μL of PCR product into each well of the Costar plate.
7. Mix gently by pipetting up and down several times. Avoid bubble formation during dispensing and pipetting.
8. Seal the plate with a BioRad sealing film.
9. Verify that all wells are properly sealed and that the lid of the thermocycler has reached the pre-set temperature.
10. Place the plate and the corresponding silicone compression mats on the thermocycler block.
11. Close the thermocycler lid and start the ID XT HYB hybridization program.

| | Temperature | Time |
|---|---|---|
| Denaturation | 95° C. | 2 min |
| Hybridization | 52° C. | 30 min |
| Hold | 52° C. | ∞ |

12. During the hybridization step prepare the labeling mix (see Labeling section) and perform the "Create a New Batch" step in the Luminex® software (see Data Acquisition section).
    Note: PCR products must be labeled immediately after hybridization. The process cannot be stopped after the hybridization step.
III. Labeling
Work in the post-PCR area.
1. Bring the following reagents to room temperature: SAPE and SAPE Dilution Buffer.
2. Prepare the labeling mix as shown in the following table (all volumes in μL):

|  | Number of samples | | | |
|---|---|---|---|---|
|  | 1 | 8 | 24 | 48 |
| SAPE Dilution Buffer | 87 | 696 | 2088 | 4176 |
| SAPE | 4.6 | 36.8 | 110 | 221 |

NOTE:
the stated volumes already include an excess to account for pipetting error.

3. Vortex the labeling mix and keep it protected from light at room temperature.
4. At the 52° C. hold step, open the thermocycler lid and remove the compression pads and the sealing film with care, while keeping the plate on the thermocycler for the labeling step.
5. Dispense 80 μL of the labeling mix into each well of the hybridization plate and mix gently by pipetting up and down once.
6. Analyze the samples using the Luminex® system immediately after labeling.
IV. Data Acquisition and Analysis
Luminex® System Preparation:
   Refer to Luminex® User's Manual (Luminex® 100™ IS 2.3. User Manual, Luminex® 200™ User Manual, or xPONENT® 3.1 Software Manual) for instrument preparation and operation, including daily startup, calibration, maintenance, and shutdown procedures.

1. Select Create a New Batch from an existing Protocol in the HOME page (for Luminex® IS 2.3 software) or Batches tab option (for Luminex® xPONENT® 3.1 software) and select the corresponding protocol.
2. Enter the sample IDs.
3. Follow the stepwise instructions that appear on the screen for creating batches. For further instructions on creating batches and multibatches, refer to the corresponding Luminex® User's Manual.
4. Select the Eject icon to eject the plate holder. Place the hybridization plate in the Luminex® XYP instrument heater block present on the plate holder.
5. Select the Retract icon. The samples are now ready to be analyzed.
6. Start the analysis process by clicking the Start icon (for Luminex® IS 2.3 software) or the Run icon (for Luminex® xPONENT® 3.1 software).
7. After a batch is complete, the data are exported as a Comma Separated Values (csv) file. This file is saved in a folder with the Batch Name entered into the Luminex® software.
8. Perform Luminex® 100/200™ daily shutdown maintenance.
9. The system can be turned off at this point if it is not going to be used for the remainder of the day.

Proprietary software (Progenika Biopharma S.A.) is used to transform fluorescence intensity values for the particular allelic variants detected, singly or in combination, into blood group genotypes, and from genotypes into predicted blood group phenotypes.

Figure 2:
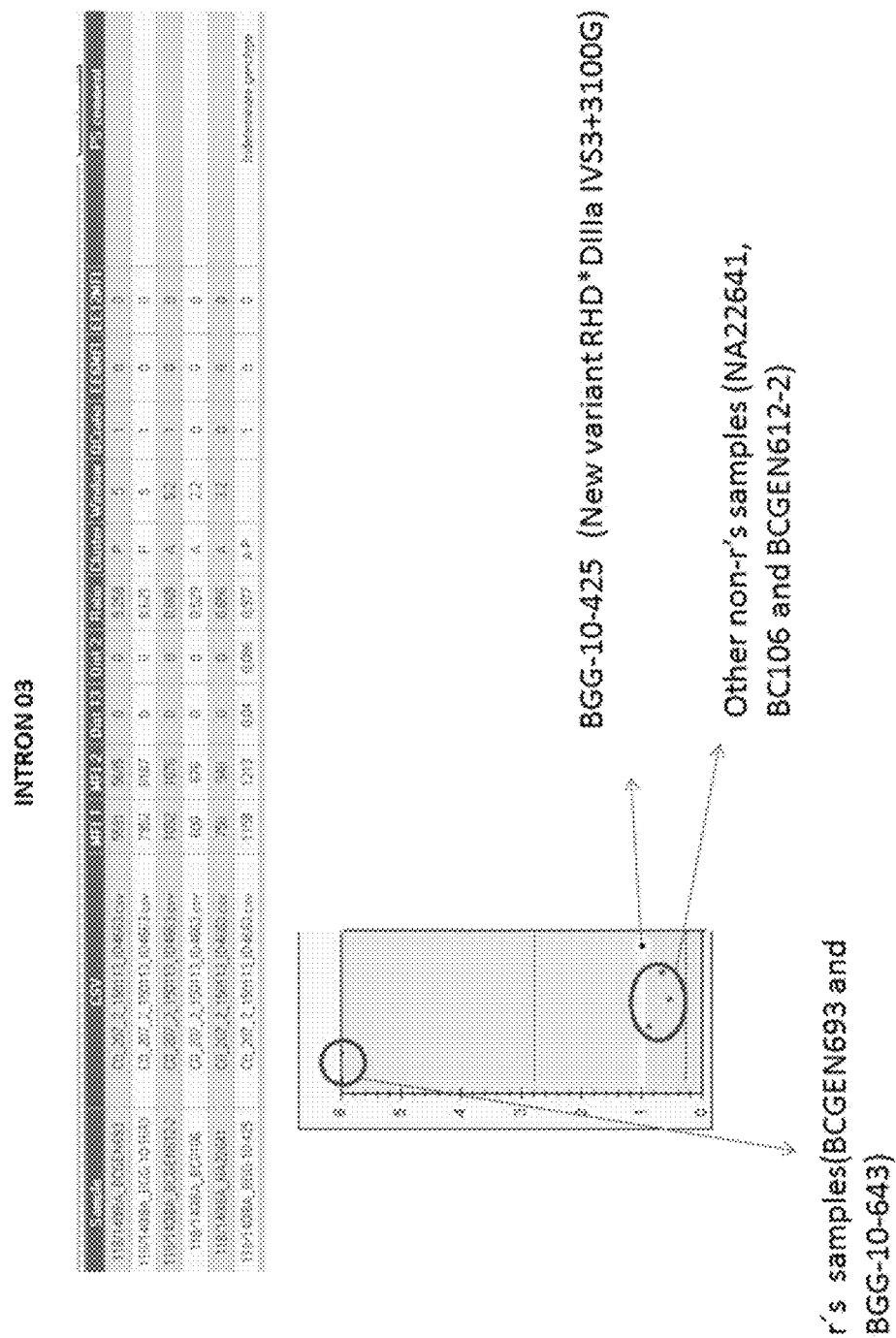
FIG. 2 shows Luminex intensity results for a variety of samples $r^s$, RHD*DIIIa IVS3+3100G and other non-$r^s$ samples following multiplex PCR using the $r^s$-specific primers shown in Table 1 and one or more primer pairs shown in Tables 2 and 3.

FIG. 2 shows the output and graphical representation (vertical axis is "normalised intensity") of a Luminex assay for $r^s$ samples, the newly-discovered variant "RHD*DIIIa IVS3+3100G", and other non-$r^s$ samples following multiplex PCR using the $r^s$-specific primers shown in Table 1 and one or more primer pairs shown in Tables 2 and 3. The data shown in FIG. 2 confirm that the $r^s$ samples are successfully amplified by PCR in multiplex and that the Luminex normalised intensity signal is markedly higher for the $r^s$ samples than for non-$r^s$ samples, including the newly-discovered variant "RHD*DIIIa IVS3+3100G". Indeed, the separation of normalised signal (greater than 6-fold higher for $r^s$ samples) provides clear unambiguous discrimination between $r^s$ samples and closely related non-$r^s$ samples, despite the relatively less stringent PCR conditions utilised for multiplex PCR. These results therefore underscore the surprising adaptability of the primers of the present invention, in particular the forward primer as set forth in Table 1, for use in multiplex allele-specific PCR for identification of $r^s$ samples.

As shown in FIG. 3, the ability of the $r^s$-specific primers of the present invention to work in multiplex with primers for amplification of other segments of the RHD gene and/or RHCE gene loci allows for efficient use of sample, e.g., to interrogate other polymorphisms relevant to the classification of blood type variants. In particular, segments including all or part of one or more RHD and/or RHCE exons and/or introns may be amplified and the amplification products interrogated by allele-specific probes in order to detect the presence or absence of, and/or identity of: an RHCE c; an RHCE C; RHCE exon 1; RHCE exon 5; RHCE exon 7; an RHD/RHCE hybrid exon 3 allele; a G/C polymorphism at position 602 of RHD exon 4; a C/G polymorphism at position 1048 of RHD exon 7; presence or absence of an RHCE*C allele; a G/T polymorphism at position 1006 of RHCE exon 7; and/or a G/A polymorphism at position 3100 of RHD intron 3.

Comparison with a Previously-Described Primer

Silvy et al., British Journal of Haematology, (2012 Dec. 30) doi: 10.1111/bjh. 12179 [Epub ahead of print], describe PCR amplification of a portion of intron 3 of the RHD gene. The amplification is said to be selective for $r^s$ (referred to therein as (C)ce$^s$ type 1 haplotype. The primer pair employed by Silvy et al. included (see FIG. 1 and Supporting information Appendix S1 of Silvy et al.):

a forward primer ("RHD-for") that is specific for RHD-containing sequence having the sequence (5' to 3'):

(SEQ ID NO: 25)
GCAAATATGGAAATTTGATCATGTA;

a reverse primer ("RHCE-rev") that is specific for RHCE-containing sequence having the sequence (5' to 3'):

(SEQ ID NO: 26)
CTTAATCACAAGATTATTTTCAGAATCTAAC;

and
a control reverse primer ("RHDCE-rev") that hybridised to both RHD-containing and RHCE-containing sequence having the sequence (5' to 3'):

(SEQ ID NO: 27)
GGGCCTTGGACAAGTTGTTA.

The method taught by Silvy et al. relies on the amplification of a 240 bp amplicon by the primer pair RHD-for and RHCE-rev being specific for $r^s$, as compared with, e.g., RHD*DIVa2 and RHD*DIIIa (see Silvy et al., FIG. 1(B)). Although Silvy et al. report amplification of 52 (C)ce$^s$ type 1 haplotype samples and negative amplification of all other samples in a 118 sample set, regardless of the RHD and RHCE alleles present, this method suffers from a number of important drawbacks. In particular, the specificity is achieved by means of the intersection of the two specific primers, RHD-for and RHCE-rev, rather than either primer itself being specific for $r^s$. This means that, for example, the RHD-for primer also hybridises to other RHD sequence-containing template, including RHD*DIIIa and RHD*DIVa2.

As described below, the present inventors have found that the method and primers of Silvy et al. result in poor discrimination of $r^s$ from, e.g., RHD*DIIIa and RHD*DIVa2 under the less stringent PCR conditions typically employed in multiplex PCR.

Moreover, Silvy et al. teach that the IVS3+3100a>g SNP is specific to (C)ce$^s$ type 1 haplotype (i.e. $r^s$). However, the present inventors have now discovered that this is not the case. In particular, a variant provisionally termed "RHD*DIIIa IVS3+3100G" has been identified herein, which is not $r^s$, but actually a variant of RHD*DIIIa having the same intron 3 position 3100 A to G polymorphism. Therefore, reliance on the presence of the intron 3 position 3100 A to G polymorphism in order to identify $r^s$ can and will lead to false positive results where a "RHD*DIIIa IVS3+3100G" sample would be incorrectly assigned as an $r^s$ sample. This is clinically relevant because "RHD*DIIIa IVS3+3100G" is C-serologically, rather than $C^{+W}$. Thus, reliance on the presence of intron 3 position 3100 A to G polymorphism in order to identify $r^s$ is undesirable.

As shown in the alignment of FIG. 7, the forward primer of Silvy et al. (RHD-for) will anneal to all of the following: RHD, $r^s$, DIVa, DIIIa and the newly-described "RHD*DIIIa IVS3+3100G" sample. Although the intersection of sequences that match the RHD-for and RHCE-rev primers of Silvy et al. can be expected to be confined to r$^{rs}$, the amplification will only be specific under stringent conditions. Under less stringent conditions, the forward primer of Silvy et al. results in a number of non-specific amplifications. In contrast, the forward primer of the present invention is specific only to r$^{rs}$.

In the process of designing the forward primers of the present invention, the inventors sought to mitigate the drawbacks associated with the forward primer disclosed in Silvy et al.

Figure 4:
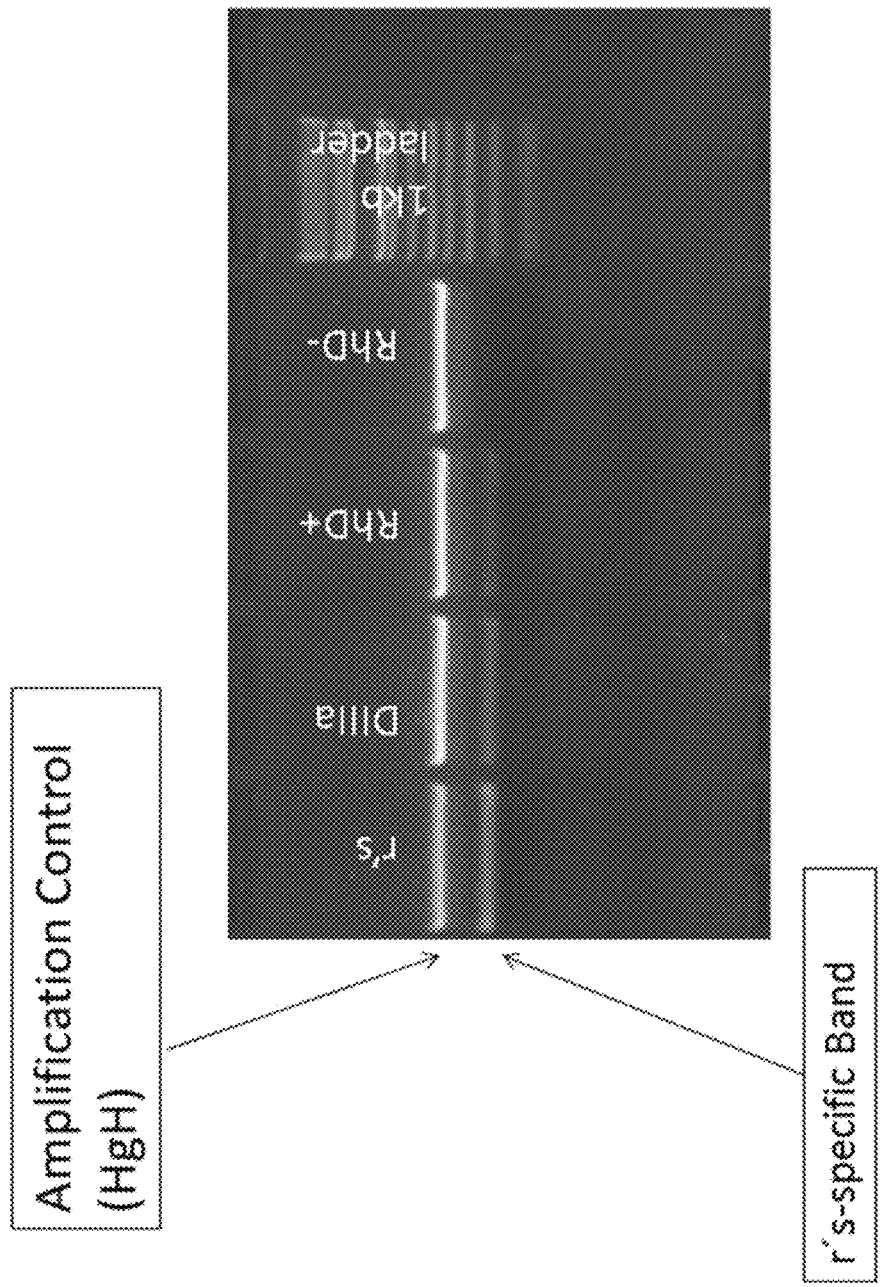
FIG. 4 shows a gel image depicting the PCR results of a reaction utilising primers for an amplification control (HgH) (upper band) and $r^s$ (lower band) for a variety of samples (including RhD$^+$, DIIIa, RhD$^-$ and $r^s$)

FIG. 4 shows the results of using the RHD-for primer of Silvy et al. having the sequence GCAAATATGGAAATTTGATCATGTA (SEQ ID NO: 25) together with the RHCE-specific reverse primer having the sequence GGAAAAGGTTTGAGAGGAATTATATT (SEQ ID NO: 11) under PCR conditions suitable for multiplex PCR. The upper band shows the amplification control (HgH), while the lower band is, theoretically, an amplicon which is specific for r$^{rs}$. Lane 1 shows that the sample "BGG-10-656", which is a known r$^{rs}$ sample is indeed amplified by the above primer combination. However, lane 2, which is the sample "BGG-10-628", being a known DIIIa sample, and lane 3, which is "L22", a known RhD+ sample, both exhibit positive amplification of the supposedly r$^{rs}$-specific amplicon. These results demonstrate that the forward primer RHD-for of Silvy et al. results in false positive results under the conditions tested. These results may be contrasted with the results obtained when using a forward primer of the present invention, in which case no such false positive results were found.

Figure 5:
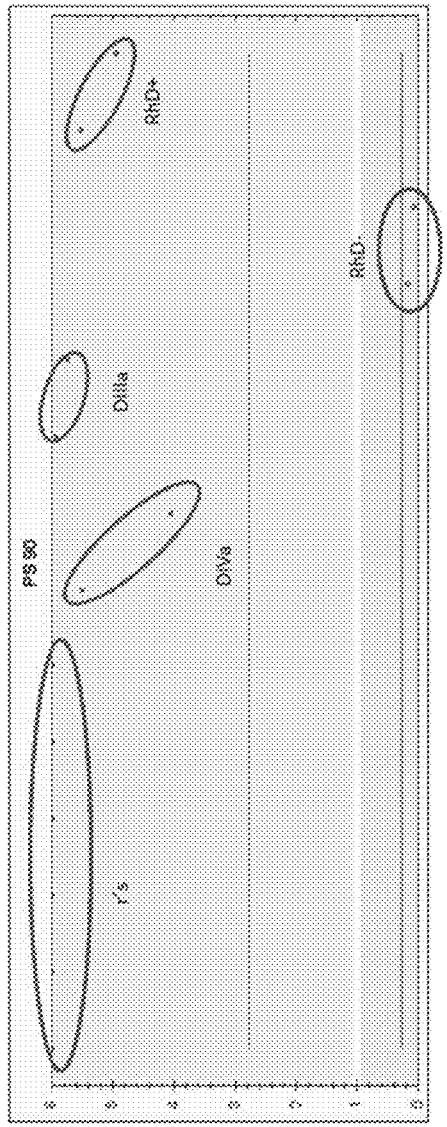
FIG. 5 shows Luminex intensity results for a variety of samples $r^s$, $r^s$/RHD+ heterozygous, $r^s$ hemizygous, DIVa-2, DIIIa, RHD− and RHD+ samples.

The results shown in FIG. 5 likewise demonstrate that the forward primer of Silvy et al. results in non-specific amplification and therefore false positive results. In particular, samples which are known DIVa, DIIIa and RhD+ all exhibited Luminex mean fluorescence intensity signal above the threshold line to be classified as r$^{rs}$ (as did the samples known to be r$^{rs}$). Samples known to be RhD− did not exhibit positive results in this experiment. These data can be contrasted with the r$^{rs}$-specific results shown in FIG. 2, wherein a forward primer of the present invention was employed.

Variant Primers of the Invention

The present inventors sought to provide primers that contain sequence modifications compared with the "reference" forward primer having the sequence AAATTTGATCATGTACTAATCATAC (SEQ ID NO: 7). By way of example, the following changes were made to the "reference" forward primer sequence, while retaining r$^{rs}$-specificity.

In a first modification, the reference primer was shortened by deleting 10 nucleotides at the 5' end, in order to decrease annealing temperature for the PCR. This modification results in the forward primer of the invention having the following nucleotide sequence: ATGTACTAATCATAC (SEQ ID NO: 8).

In a second modification, the reference primer was altered by introducing one nucleotide substitution (replacing a C with a G) to increase specificity. This modification results in the forward primer of the invention having the following nucleotide sequence (the substitution position being underlined): AAATTTGATCATGTACTAATGATAC (SEQ ID NO: 9).

In a third modification, the reference primer was altered by introducing one nucleotide substitution that differs from the substitution described above in relation to the second modification. This substitution was also a replacement of a C with a G to increase specificity, but was at a different position. This modification results in the forward primer of the invention having the following nucleotide sequence (the substitution position being underlined): AAATTTGATCATGTAGTAATCATAC (SEQ ID NO: 10).

Figure 6:
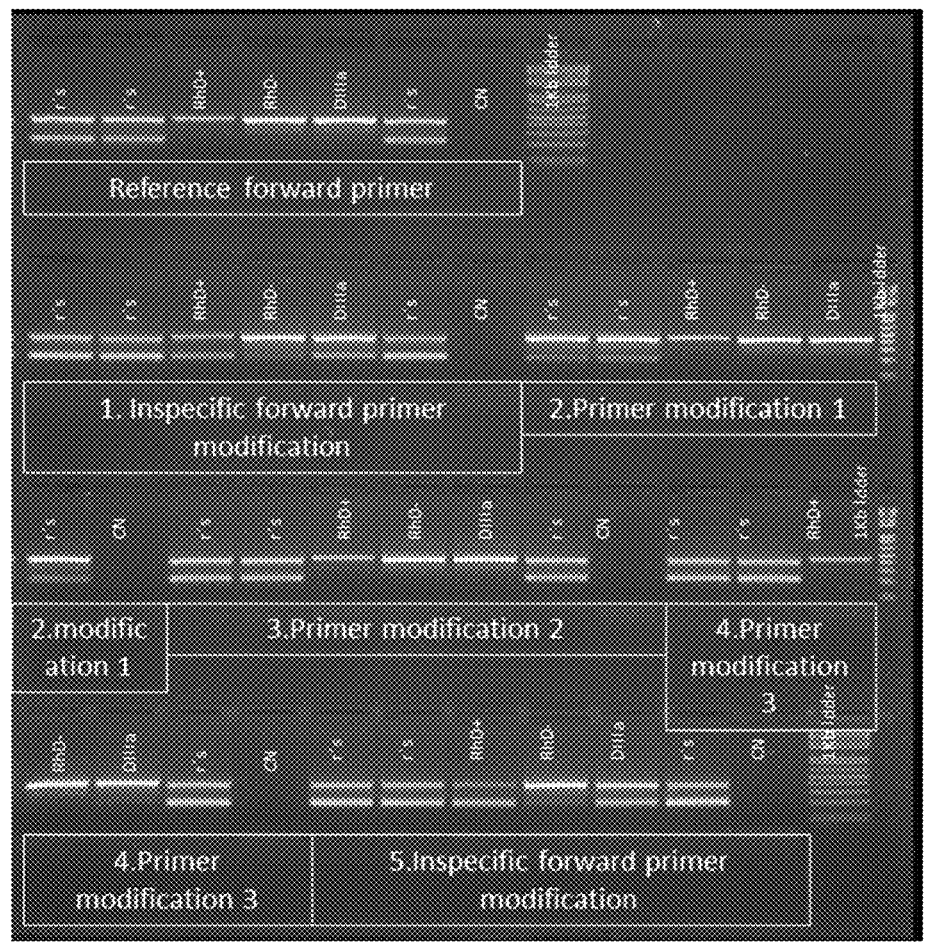
FIG. 6 shows a gel image depicting the PCR results of a number of PCR reactions comparing different primer combinations. An amplification control (HgH) (upper band) and $r^s$ (lower band) are shown for a variety of samples ($r^s$, RhD$^+$, RhD$^-$, DIIIa and a negative control.

FIG. 6 shows PCR results obtained using: the reference forward primer of the invention AAATTTGATCATGTACTAATCATAC (SEQ ID NO: 7); the "inspecific" forward primer of Silvy et al. GCAAATATGGAAATTTGATCATGTA (SEQ ID NO: 25); the variant primer of the invention having modification 1 ATGTACTAATCATAC (SEQ ID NO: 8); the variant primer of the invention having modification 2 AAATTTGATCATGTACTAATGATAC (SEQ ID NO: 9); the variant primer of the invention having modification 3 AAATTTGATCATGTAGTAATCATAC (SEQ ID NO: 10); and a modified version of the "inspecific" forward primer of Silvy et al. having the sequence G GCAAATATGGAAATTTGATCATGTA (SEQ ID NO: 28). In all cases the reverse primer used was GGAAAAGGTTTGAGAGGAATTATATT (SEQ ID NO: 11).

FIG. 6 shows the PCR amplification results of the above-described primers. The top band is a control and the lower band is intended to be an r$^{rs}$-specific amplification product, to the extent that the primers used in fact amplify in an r$^{rs}$-specific manner under the conditions employed. As shown in FIG. 6, the reference forward primer (upper panel) exhibits r$^{rs}$-specific amplification (positive for three known r's samples (lanes 1, 2 and 6) and negative for non-r$^{rs}$ (RhD+ in lane 3, RhD− in lane 4 and DIIIa in lane 5). The negative control of lane 7 shows no amplification.

The inspecific forward primer in box 1 (second panel down; left hand side) exhibits positive r$^{rs}$ band presence of not only r$^{rs}$ samples, but also RhD+ and DIIIa (see lanes 3 and 5), thus confirming false positive results.

The primer modification 1 results are shown in box 2 (spanning the second panel, right hand side and third panel, left hand side). The r$^{rs}$ band, although somewhat less bright than the upper control band, is clearly visible in all r$^{rs}$ samples (lanes 1, 2 and 6), while all other lanes (RhD+, RhD−, DIIIa and negative control) are without any r$^{rs}$ band. These results confirm that the modification to the reference forward primer (shortening it by deleting the 5' 10 nucleotides) nevertheless retains r$^{rs}$ specificity.

The primer modification 2 results are shown in box 3 (third panel, center). The r's band is clearly visible in all r's samples (lanes 1, 2 and 6), while all other lanes (RhD+, RhD−, DIIIa and negative control) are without any r$^{rs}$ band. These results confirm that the modification to the reference forward primer (C to G substitution to generate a single base mismatch) nevertheless retains or even increases r$^{rs}$ specificity.

The primer modification 3 results are shown in box 4 (spanning the third panel, right hand side and fourth panel, left hand side). The r$^{rs}$ band is clearly visible in all r$^{rs}$ samples (lanes 1, 2 and 6), while all other lanes (RhD+, RhD−, DIIIa and negative control) are without any r$^{rs}$ band. These results confirm that the modification to the reference forward primer (C to G substitution to generate a single base mismatch) nevertheless retains or even increases r$^{rs}$ specificity.

The inspecific forward primer in box 5 (fourth panel right hand side) exhibits positive r$^{rs}$ band presence of not only r$^{rs}$ samples, but also RhD+ and DIIIa (see lanes 3 and 5), thus confirming false positive results. There is even a faint r$^{rs}$ band visible in the RhD− sample (lane 4).

Taken together, the present results demonstrate that the reference forward primer of the present invention exhibits superior performance compared with that of the Silvy et al. RHD-for primer and that the forward primer of the present invention is tolerant to a number of sequence modifications, including a 5' truncation of 10 nucleotides (i.e. reducing the value of n in the formula X-Y-Z as defined herein) and nucleotide substitutions that result in mismatches with the target sequence (i.e. selection of $S_1$, $S_2$ and/or changes reflected in the substitution possibilities of $X_2$ and/or $Y_2$ of the formula X-Y-Z as defined herein. The present invention therefore provides, inter alia, a genus of related forward PCR primer designs that address the need for $r^{ts}$-specific amplification and mitigate the drawbacks associated with a previously-described primer.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, including patent documents, disclosed herein are incorporated by reference in their entirety for all purposes, particularly for the disclosure referenced herein.

The invention claimed is:

1. An oligonucleotide polymerase chain reaction (PCR) primer, the nucleotide sequence of which comprises the sequence:

```
                                    (SEQ ID NO: 10)
AAATTTGATCATGTAGTAATCATAC;
or
                                    (SEQ ID NO: 9)
AAATTTGATCATGTACTAATGATAC.
```

2. An oligonucleotide polymerase chain reaction (PCR) primer, the nucleotide sequence of which comprises the sequence:

```
                                    (SEQ ID NO: 10)
AAATTTGATCATGTAGTAATCATAC;
or
                                    (SEQ ID NO: 9)
AAATTTGATCATGTACTAATGATAC,
``` wherein at least one nucleotide of said primer is a biotinylated nucleotide, a fluorescently labelled nucleotide, or a locked nucleic acid (LNA) nucleotide.

3. The primer according to claim 1, wherein said primer is suitable for use as a forward PCR primer in a PCR amplification of a portion of the $r^{\prime S}$ allele of intron 3 of the RHD gene.

4. A plurality of oligonucleotide primers comprising:
  (i) the oligonucleotide primer as defined in claim 1; and
  (ii) at least one primer selected from the group consisting of:
    (a) an oligonucleotide primer of between 26 and 30 nucleotides in length comprising the nucleotide sequence GGAAAAGGTTTGAGAGGAATTATATT (SEQ ID NO: 11) or a variant thereof differing by not more than 3 nucleotide substitutions from the nucleotide sequence of SEQ ID NO: 11, provided that said substitutions do not include substitution of the final T of the nucleotide sequence of SEQ ID NO: 11;
    (b) an oligonucleotide primer comprising the nucleotide sequence GGAAAAGGTTTGAGAGGAATTATATT (SEQ ID NO: 11);
    (c) the RHCE c forward primer consisting of the nucleotide sequence TGGGCTTCCTCACCTCAAA (SEQ ID NO: 12);
    (d) the RHCE c reverse primer consisting of the nucleotide sequence TGATGACCACCTTCCCAGG (SEQ ID NO: 13);
    (e) the RHCE C forward primer consisting of the nucleotide sequence GGCCACCACCATTTGAA (SEQ ID NO: 14);
    (f) the RHCE C reverse primer consisting of the nucleotide sequence GGTAGCAGGCGTCTGTAAAAA (SEQ ID NO: 15);
    (g) the RHCE exon 1 forward primer consisting of the nucleotide sequence CATAGACAGGCCAGCACAG (SEQ ID NO: 16);
    (h) the RHCE exon 1 reverse primer consisting of the nucleotide sequence TGCCCCTGGAGAACCAT (SEQ ID NO: 17);
    (i) the RHCE exon 5 forward primer consisting of the nucleotide sequence AAATTAAAATAAGCATTTGACCATC (SEQ ID NO: 18);
    (j) the RHCE exon 5 reverse primer consisting of the nucleotide sequence CCTGAGATGGCTGTCACCAC (SEQ ID NO: 19);

(k) the RHCE exon 7 forward primer consisting of the nucleotide sequence ACATGCCATTGCCGTTC (SEQ ID NO: 20); and (l) the RHCE exon 7 reverse primer consisting of the nucleotide sequence TCTCACCTGCCAATCTGCT (SEQ ID NO: 21).

5. The plurality of oligonucleotide primers according to claim 4, wherein said primers comprise:

a forward primer comprising the nucleotide sequence:

```
                                    (SEQ ID NO: 10)
AAATTTGATCATGTAGTAATCATAC;
or
                                    (SEQ ID NO: 9)
AAATTTGATCATGTACTAATGATAC;
``` and a reverse primer comprising the nucleotide sequence:

```
                                    (SEQ ID NO: 11)
GGAAAAGGTTTGAGAGGAATTATATT.
```

6. A kit for assessing a subject's blood type, said kit comprising:

the plurality of primers as defined in claim 4;

optionally, one or more probes and/or primers that span one or more polymorphic positions in intron 3, exon 3, exon 4, intron 7 and/or exon 7 of the RHD gene locus; and optionally, one or more probes and/or primers that span one or more polymorphic positions in exon 7 of the RHCE gene locus.

7. A system for use in determining a subject's blood type, the system comprising:

the kit as defined in claim 6; and at least one detector arranged to detect a signal from detectably labelled DNA obtained from said subject or a detectably labelled amplicon produced by PCR amplification carried out on DNA obtained from said subject;

at least one controller in communication with the at least one detector, the controller being programmed with computer-readable instructions to transform said signal into predicted blood type haplotypes, and optionally, to transform said predicted blood type haplotypes into a predicted blood type phenotype.

8. A method for determining the presence or absence of, or for discriminating between, blood type alleles in a DNA-containing sample, which method comprises amplification by polymerase chain reaction (PCR) of at least a portion of intron 3 of the RHD gene, wherein said PCR employs at least a forward primer and a reverse primer each capable of hybridising to the portion of $r^{tS}$ intron 3 sequence set forth in SEQ ID NO: 31, or its complement, and wherein said forward primer is as defined in claim 1.

9. The method according to claim 8, wherein said blood type alleles are alleles that comprise an RHD/RHCE hybrid exon 3.

10. The method according to claim 8, wherein said blood type alleles are selected from the group consisting of: RHD*$r^{tS}$; RHD*$r^{tS}$-like; RHD*$r^{tS}$ Type 1; RHD*$r^{tS}$ Type 2; RHD*DIIIa; RHD*DIIIa IVS3+3100G; RHD*DIII_FN; RHD*DIVa-2; RHD*DIVa; RHD*DIII-type4; RHD*DIII-type6; RHD*DIII-type7; RHD*DIII-type8; RHCE*$ce^S$; RHCE*$ce^S$ 1006T; RHCE*$ce^S$ 1006C; RHCE*ce733G; RHCE*ce48C,733G,1025T; RHCE*ce48C,697G,733G; RHCE*ce340T,733G; and RHCE*ce48C,733G,748A.

11. The method according to claim 8, wherein said PCR amplifies $r^{tS}$, but does not amplify one or more of: RHD; RHCE*ce; RHD*DIIIa; RHD*DIIIa IVS3+3100G; and RHD*DIVa.

12. The method according to claim 11, wherein said PCR amplifies $r^{tS}$, but does not amplify any of RHD; RHCE*ce; RHD*DIIIa; RHD*DIIIa IVS3+3100G; and RHD*DIVa.

13. The method according to claim 8, wherein said forward primer comprises the nucleotide sequence AAATTTGATCATGTAGTAATCATAC (SEQ ID NO: 10), and said reverse primer comprises the nucleotide sequence GGAAAAGGTTTGAGAGGAATTATATT (SEQ ID NO: 11).

14. The method according to claim 8, wherein the method further comprises genotyping the sample at one or more positions of single nucleotide polymorphism (SNP) in the RHD and/or RHCE gene loci.

15. The method according to claim 14, wherein the method further comprises genotyping the sample at one or more of:

(i) position 410 of the RHD exon 3;

(ii) position 602 of the RHD exon 4;

(iii) position 1048 of the RHD exon 7;

(iv) position 1006 of the RHCE exon 7; and (v) position 3100 of the RHD intron 3.

16. A method of blood matching, the method comprising:

carrying out the method according to claim 8 on a recipient sample from a recipient subject in need of donor blood and on a donor sample from a potential donor subject;

comparing the blood type alleles present in the recipient sample with those present in the donor subject and thereby determining the compatibility of the recipient subject to receive blood from the potential donor subject.

17. An oligonucleotide primer pair comprising:

(i) an oligonucleotide forward primer comprising the nucleotide sequence of AAATTTGATCATG-TACTAATCATAC (SEQ ID NO: 7), AAATTTGAT-CATGTAGTAATCATAC (SEQ ID NO: 10), or AAATTTGATCATGTACTAATGATAC (SEQ ID NO: 9), wherein at least one nucleotide of said forward primer is a biotinylated nucleotide, a fluorescently labelled nucleotide, or a locked nucleic acid (LNA) nucleotide; and (ii) an oligonucleotide reverse primer comprising the nucleotide sequence of GGAAAAGGTTTGAGAG-GAATTATATT (SEQ ID NO: 11), wherein the oligonucleotide primer pair is capable of specific amplification of a portion of intron 3 of the RHD gene found in $r^{tS}$.

* * * * *

SEQUENCE LISTING

```
<160> NUMBER OF SEQ ID NOS: 32

<210> SEQ ID NO 1
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 1
atatggaaat ttgatcatgt                                    20

<210> SEQ ID NO 2
<211> LENGTH: 11
<212> TYPE: DNA
<213> ORGANISM: Artificial sequence
<220> FEATURE:
<223> OTHER INFORMATION: Synthetic sequence: Primer

<400> SEQUENCE: 2
astaatsata c                                             11

<210> SEQ ID NO 3
<211> LENGTH: 14
<212> TYPE: DNA
<213> ORGANISM: Artificial sequence
<220> FEATURE:
<223> OTHER INFORMATION: Synthetic sequence: Primer

<400> SEQUENCE: 3
aaatttgatc atgt                                          14

<210> SEQ ID NO 4
<211> LENGTH: 11
<212> TYPE: DNA
<213> ORGANISM: Artificial sequence
<220> FEATURE:
<223> OTHER INFORMATION: Synthetic sequence: Primer

<400> SEQUENCE: 4
actaatcata c                                             11

<210> SEQ ID NO 5
<211> LENGTH: 11
<212> TYPE: DNA
<213> ORGANISM: Artificial sequence
<220> FEATURE:
<223> OTHER INFORMATION: Synthetic sequence: Primer

<400> SEQUENCE: 5
```
actaatgata c                                                    11

<210> SEQ ID NO 6
<211> LENGTH: 11
<212> TYPE: DNA
<213> ORGANISM: Artificial sequence
<220> FEATURE:
<223> OTHER INFORMATION: Synthetic sequence: Primer

<400> SEQUENCE: 6
agtaatcata c                                                    11

<210> SEQ ID NO 7
<211> LENGTH: 25
<212> TYPE: DNA
<213> ORGANISM: Artificial sequence
<220> FEATURE:
<223> OTHER INFORMATION: Synthetic sequence: Primer

<400> SEQUENCE: 7
aaatttgatc atgtactaat catac                                     25

<210> SEQ ID NO 8
<211> LENGTH: 15
<212> TYPE: DNA
<213> ORGANISM: Artificial sequence
<220> FEATURE:
<223> OTHER INFORMATION: Synthetic sequence: Primer

<400> SEQUENCE: 8
atgtactaat catac                                                15

<210> SEQ ID NO 9
<211> LENGTH: 25
<212> TYPE: DNA
<213> ORGANISM: Artificial sequence
<220> FEATURE:
<223> OTHER INFORMATION: Synthetic sequence: Primer

<400> SEQUENCE: 9
aaatttgatc atgtactaat gatac                                     25

<210> SEQ ID NO 10
<211> LENGTH: 25
<212> TYPE: DNA
<213> ORGANISM: Artificial sequence
<220> FEATURE:
<223> OTHER INFORMATION: Synthetic sequence: Primer

<400> SEQUENCE: 10
aaatttgatc atgtagtaat catac                                     25

<210> SEQ ID NO 11
<211> LENGTH: 26
<212> TYPE: DNA
<213> ORGANISM: Artificial sequence
<220> FEATURE:
<223> OTHER INFORMATION: Synthetic sequence: Primer

<400> SEQUENCE: 11
ggaaaaggtt tgagaggaat tatatt                                    26

<210> SEQ ID NO 12
<211> LENGTH: 19
<212> TYPE: DNA
<213> ORGANISM: Artificial sequence

```
<220> FEATURE:
<223> OTHER INFORMATION: Synthetic sequence: Primer

<400> SEQUENCE: 12
tgggcttcct cacctcaaa                                                    19

<210> SEQ ID NO 13
<211> LENGTH: 19
<212> TYPE: DNA
<213> ORGANISM: Artificial sequence
<220> FEATURE:
<223> OTHER INFORMATION: Synthetic sequence: Primer

<400> SEQUENCE: 13
tgatgaccac cttcccagg                                                    19

<210> SEQ ID NO 14
<211> LENGTH: 17
<212> TYPE: DNA
<213> ORGANISM: Artificial sequence
<220> FEATURE:
<223> OTHER INFORMATION: Synthetic sequence: Primer

<400> SEQUENCE: 14
ggccaccacc atttgaa                                                      17

<210> SEQ ID NO 15
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 15
ggtagcaggc gtctgtaaaa a                                                 21

<210> SEQ ID NO 16
<211> LENGTH: 19
<212> TYPE: DNA
<213> ORGANISM: Artificial sequence
<220> FEATURE:
<223> OTHER INFORMATION: Synthetic sequence: Primer

<400> SEQUENCE: 16
catagacagg ccagcacag                                                    19

<210> SEQ ID NO 17
<211> LENGTH: 17
<212> TYPE: DNA
<213> ORGANISM: Artificial sequence
<220> FEATURE:
<223> OTHER INFORMATION: Synthetic sequence: Primer

<400> SEQUENCE: 17
tgcccctgga gaaccat                                                      17

<210> SEQ ID NO 18
<211> LENGTH: 25
<212> TYPE: DNA
<213> ORGANISM: Artificial sequence
<220> FEATURE:
<223> OTHER INFORMATION: Synthetic sequence: Primer

<400> SEQUENCE: 18
aaattaaaat aagcatttga ccatc                                             25
```

<210> SEQ ID NO 19
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 19
cctgagatgg ctgtcaccac                                               20

<210> SEQ ID NO 20
<211> LENGTH: 17
<212> TYPE: DNA
<213> ORGANISM: Artificial sequence
<220> FEATURE:
<223> OTHER INFORMATION: Synthetic sequence: Primer

<400> SEQUENCE: 20
acatgccatt gccgttc                                                  17

<210> SEQ ID NO 21
<211> LENGTH: 19
<212> TYPE: DNA
<213> ORGANISM: Artificial sequence
<220> FEATURE:
<223> OTHER INFORMATION: Synthetic sequence: Primer

<400> SEQUENCE: 21
tctcacctgc caatctgct                                                19

<210> SEQ ID NO 22
<211> LENGTH: 64956
<212> TYPE: DNA
<213> ORGANISM: Homo sapiens

<400> SEQUENCE: 22
gacaccccag ccacgccaag ccgggaagtc cccgcctcct ggagctgaac ccgcccctct    60
cccagaggtg gagctgcggg gggcgggaac aggcacggag aaaataaaca agactaaaaa   120
gtcctgagta gcgctgtgtg gccgcaaacc tgaacccacc ttttgcacca cgcgggaccc   180
ggcacgcttc ctgccaccca cccctgagag gctgcgcgg ccgaccccag tactagaaaa    240
cactcgtcac ctcaatcaag acgggtacga aggccaacgg acgccttcct ttagaacgct   300
cagcacacag agcaacttct cacgcctact ctcaaatggc gtactccaaa ctagcactcc   360
cgacgtccag ctgtgaaccc agagcggcgg aaagcccctg aacccagcgc ccgggcatgc   420
gcagacgcgt tgttgtggtg ggcgtggctc cctccggacc cggcgccccg ccctccgccc   480
cgtgtccgca tgcgcgactg agccgcgggg gtggtactgc tgcatccggg tgtctgaaga   540
tccgatgaaa taacatatgc aaaatgattg ggtccgtgat tggcattcca gaaatggtag   600
ctgttattca gccaacaaat atttattgag cacctactat ggacttccct ggtgctgagg   660
atacaacagc aaccacagca gtcaaaagtc cctgtcttca tgttgctcag attctcatag   720
gggaaagcaa ataatgaaca aatacacggc cgggcgcagt ggctcacgcc tgtaatccca   780
gtactttgcg aggccaaggt gggcaagtca cctgaggtca ggagttcgag accagactag   840
ccaacgtggt gaaaccctgt cactactaaa aatacaaaaa ttagcgcggt gtggtggctc   900
atgcctgtag tcccagctac ttgggaggct gaggaaggag aatcgcttga acctaaaagg   960
cagaagttgc aatgagccaa gatcgtgcca ctgcattcca gcctgggtga cagagtactc  1020
cgtctaaaaa aaaaacctaa atacacaagt aaaaatatag acctcgtcag atgctagtaa  1080

```
gtgctgtgaa ggaaactaaa aggggaacac aaggaaccct tgtcaagggg agaagaaagg    1140
ggagttgatg ctgtccttt aaatagggca gtcagaggcc gggcacagtg gttcacacct    1200
ataatcccag cactttggga ggttgaggtg ggtggatcac ttgaggtcag gagttcaaga    1260
ccagcctggc caacctggtg aaatcctgtc tctactaaaa aaacaaaaac tagccgggtg    1320
tggtatcacg cgcctataat cccagctact cgggaggctg aggcgggaga atcacttgaa    1380
cctgggaggt ggaggttgca gtgagccgag attgtgccat tgcagtccag cctaggcaac    1440
aagagcaaaa cttcatctca aaaaaaaaa aaaaatagg gcagtcaggg aaaactttcc    1500
tgagaagggg atggtggagg atccaggag gtgaggtggg gagcaagcca gtacagttgt    1560
tccttgactt tcgatggggt tatgtcctga taaagccatg gtaagtagga aatattgtaa    1620
gtcaaaaatg catttaatac atctaaccta cggaacatca tagcttagtc tcacctacct    1680
taaacatgct tagaacactt acattagcct acagttgggc aaaatcctct aacacaaagc    1740
ctattttatg ataaagtatt gaatatctca tgtaatgtac tgagtactgt acggaaagtg    1800
aaagacggag tggtgggatg ggaactctaa gcgcggcttc cactgcatgt gtgttgcttt    1860
cgcgccatca taaagttgaa aagcgttaag tcaaaccatc gtacgtcgga ggccatctgt    1920
atctggtagg aggagtgttt cagacagaga gaacagcagg tgcacagagt gcttttttcc    1980
cagcatttta ttatgaaaaa tttcaaacat ctaccaaaaa aagttgaaag acttgtacag    2040
tgaaaagcca tacatctcac agctagaatc aacaattaac attttactgt atttggtttt    2100
tgacttatct atcctagatc ccttgtgctt tctgtagcag gtgacctgcc ttgaagattt    2160
aaagacagaa tatcaggaaa tgtagtcaga aaatggggcc ttttataaga gtcagagggg    2220
aagagcaaaa cctctgcttt tgacaaatct gttgggagag gccaactgca gggatacctc    2280
ccttttttaa tgaaagcatt tctgttctgc gaggagcggg atcctcttgt caagcagtca    2340
gtccctgctg cttccttact ggggcaggat caggacgcac agggatttgg agtgccttgg    2400
aaccaaccac cacccacgcc gtttgccagc tggtaaacat gcccatcagg tccgggggtt    2460
ggcattgcct ggacatcttt agtgttcatc ttgctgacat ctggtgccct cgggcaggta    2520
ggtgcagttg gctgcctggt ttacagagct tgtactgggc ccaggttagc agaggtcaca    2580 tccattatc ccactgcgca gaggagttcc ttctcaggaa acccagttta taagaagtac    2640
tgactgccag aaatagagca gaaatgagaa ccaggaggca attgtgagag gaatgggagac    2700 ttctgacctc tggggattgg ggtaccctcc cccttaattg ctgttggggt agcagagggc    2760
ttagaagccc atgttcctag actttagaa ttggaagaag acttagaagt aatctaggct    2820
gggggtcccc aaccccagg ctgtggcccg ttaggaacct gaccgcacag catgagggat    2880
aggccagcga gcactaccgc ctgagctccg cctcctgtca gatcagcagc ggcattagat    2940 tctcatagg gcacaaaccc tattgggaac cgcgcatgag agggatctag gttgcgtgct    3000
ccttaggaga atctaactaa tgcctgatga tctgaggtgg aacagtttca tccccaaacc    3060
atccctccaa cctcaccccg gtccatggaa aaattgtctt ttacaaaacc cgtccctggt    3120
gccaaaaagc ttggggaccc ctgatctagg ctacagttaa gtggtcaaac acccaggtcc    3180
tgaagttagg ctgcctggt ttaaatccca gctctactgc ttactagccc tgtgaccttg    3240
agcaagtcac ttagtttttc tgtgcctcag ttcactcatt tgtaataaat cctaatagta    3300
cccatcccag tgtcatgaac taagttcata tatgtaaagt acttgaaatg gtgcctagca    3360
agtacttaat aacagttagc tctgaaaatg tataaagcaa aattaaccaa tgttttagtg    3420
```

```
gtttgcagcc aactttttc tatgcgtgtg ctaacatatt attttataag agtgggaata    3480
tattgtacat gctgttatat aacttgcttt tcactaaac agtctatcct ctgtgtcagt    3540
tttgataaaa gcgttttcct cttgcttttc ctgcatatgt tcagaaccat catattggta   3600
gcaagtttca tgtcctgtag ttttcttaac caacccctg ctagtggaca tttaggttag    3660
tctcagtttt ttccttctgt aaataaagct gcactgagca agaagtgact gatgccaagt   3720
gactagatga ccttaggtat gacctctctg ggtcttggtt tcttggtcta aaaacaaaat   3780
gacaggattc gactgggtga ttaaaatctc ctctgatcta cataggaatt gttttcaaga   3840
catttctgca ttcctctagt gacagggtgc tcactacctc atgagtattt cagtggacaa   3900
ctgtaatggt caataaagta tccactttcc acctcctgc agctcctggc cctggcttta   3960
ttctctgggg ctccacacat tcagtttaca ctcagtggcc agtggctggg accattgtag   4020
aaaataagga aactccaatt ccttccttct tttcttcctc tttcatctct tcctccctct   4080
ctacatccct ctctctcttc cttccttcct cgacacttac catgtaccag accttctgcc   4140
aggcacatgg atgggagcac aggggaagtt ggctgcaggg ttagaactaa gtcccaagcc   4200
ccctaaagct catgccaggg gactggactg tccagtactg agggatgggg atgctgaggc   4260
tggtggcctt cctcaaatgc actgtagtgc cccaggcaga gtcctgggct gccctgtgag   4320
gaggtgacca gaggtagagc aacttcaccc taaggctgga tcaggatccc ctccaggttt   4380
ttactagagc caaacccaca tctcctttct cttctgccac ccccccttaa aatgcttaga   4440
aacacataga tttaaataca aattcaaatg taagtaattt caactgtgta actatgagga   4500
gtcagttcta cgtgggtcct atctgtatcc tccccagggc tcagctccat tctttgcttt   4560
cattcattct cattcaatac attgttgtta agagctcact gggtgccctc tctgtcatgt   4620
agtaaggttt taaaagaaa gcctcttctg agcttcagtt tccttattca taaaatagga   4680
gtattgatcc attccttgct tttcttacaa ggatatgctg aagatgactg aagtacagag   4740
taaagaagga ttatgtttgg gtgtcaaagg aatagaatgc cctctttcaa actgagcaca   4800
gcaggaacct gtaacaggaa cacagcaact tgttgaatga atgacaatat tggaaaacat   4860
acatttcctc ccctccccat catagtccct ctgcttccgt gttaactcca tagagaggcc   4920
agcacaacca gccttgcagc ctgagataag gcctttggcg ggtgtctccc ctatcgctcc   4980
ctcaagccct caagtaggtg ttggagagag gggtgatgcc tggtgctggt ggaaccctg   5040
cacagagacg gacacaggat gagctctaag tacccgcggt ctgtccggcg ctgcctgccc   5100
ctctgggccc taacactgga agcagctctc attctcctct tctatttttt tacccactat   5160
gacgcttcct tagaggatca aaagggctc gtggcatcct atcaaggtga gagttcattg   5220
gaaaagtggt cacaggagca aatagcaggg gcaggggcgg gggaggcctg tggttctcca   5280
ggggcacaga tgttcctttc tacaaaatcc caaggaaaaa gattccccca tcttcttccg   5340
tagattgcac cgaaattcag ccaacaatgt aagctttcct ttagaagcag cctgggcatg   5400
ccctcttctg tgaagcctgc cttgattttt cagcacagtg agaggcatcc tctttggtgt   5460
tcctcaaatt ccctctacca aatggtcttc ataattctct gcttctctgc ttcccccttct   5520
ctctcctcag tggcaaggaa ttttttttatt tttatagatt tagggatac aagtgcagct   5580
atcttatgca agcaatttca tgttgttggg ttttttggttt ttgtttcctt tttgtggcct   5640
ctcgctcatt tcttatttct ttttgaggca gggtctcact ctgttgccca ggctgaagtg   5700
cagtggcatg atcatggttc actgcagcct tgacctccta gtctcaagca atcttcccac   5760
ctcagcctcc caagaagctg ggaccacagg agggcaccac catgcctggc taattttttt   5820
```

```
ttttttttttt tttggtagag atgtgggtct ccctgtgttt cccagactgg tctcaaactc    5880
ctggacacaa gcgatcctcc agcctcagtc tcccaaagtg ctggaattac aggcgtgaag    5940
cactgtgccc agctctcttg ctcatatcta tactagtttt cttttggaag cttcagcctg    6000
ttgctacccc ccaccccac ccccaccgac cccagctttc ttctcactta ggggctggga     6060
agtctgcatg ctgtctataa atccagaacc agaaggtatg gctgaagggg agggtaggat    6120
gatggttatt ttatattcag ctaaaaatat tcccagactg tgatgagaca actgtaaata    6180
agacagatgt ccacaatggt gtgactttgc ttttttaaaa atattgaaat gagtttcagg    6240
catctcagtg ggctgatagg ttgttgataa tagacagggc ctccttgaag aatgtccctg    6300
agacaaagtt gaagcttgag cctggttgag tccttgcttg ttcctaggtt gatatgaacg    6360
gctagttaac tggaagcaaa gagaagtcat cctgggggcc atggcagtga caagtaggac    6420
ttagggaggg aagcccttat accatttaag gtgctggccc agagaggagc cttcagtgac    6480
agacaaacaa gagctggcac aattttaatt cacttcaatt tactctaatt catttcaatc    6540
caatacaatt caatgcattc cattcattca accatgtatg acatccaatg tgggatccag    6600
actcatgatg attagagctg atatttatga gcacttacta tgtaccaggc actattctac    6660
atgctttaca ttgaaccctc acaataaccc aatgaggtgg gtactattat gatcttcgtt    6720
tttcatatga ggaaactagg catatggatg ttgagtaatt tgcccacggt cgctcagcta    6780
gcaatagcac agcgtattta aatttagcca ccctggattt agtttcctta cacttaacca    6840
ttatgcatca tggccccatt ttacagtggg cttgagtctt tgtcatataa cccagtaggt    6900
tagcagccac tattccaacc ctgtagattg actctagggt ccatgttctt tacccctgca    6960
ccgtgctact aacgtaggta caaaatgtcc tcagaaactc actttatacg gaagctcaga    7020
ggagggtcca caacccaggc aggggagacg atggtgtcag ggagggagg tgactgccca     7080 gccaggtctt gaaggctcag taggaattac ctgtgggaca aaggagggtc atccaagtga    7140
gggcacagtg ggtgccatgg cgtgcacaca caatagagca gactgagcct gggcttaaca    7200
ttgcattgcc ctggagccta aaggggaaa caaagggccg ggcgacgtgg ctcacgcctg     7260
taatcccggc acattgggag gccaaggctg gagaatcacc tgaggttagg agttcgagac    7320
cagcctggcc aacatggcaa aaccgcatct ctactaaaat tataaaaact ggctgggtgt    7380
ggtggcacac gtctataatc cgagctactt gggaggccat tacactccag cctgggcgcc    7440
agagtgagac ttcatctcaa aaaccaaac aacaaaaaca acaacaagaa caacaaaaaa     7500
acaaagagga gagcagggac tgggtgtggt gactcatgcc tgtaatccca acactttgg     7560 gagaccaagg caggcagatc acctgaggtc aggagttcga ccagcctg gccaacatgg      7620 taaaaccctg tctctactaa aaatacaaaa attagccgga tgtggtggca cgtgcctgta    7680
gtcccagctg cttgggaagc tgagggagga gaattgcttg aacccaggag gcagaggttg    7740
ctgagctgag aacatgccac tgcactccac cctgggtgac agagtgggac tctgtctgaa    7800
aaaaataata gtaataaata aaaataaaga gggaagcagc gggtggcaga ctcactgggc    7860
tgcatacgaa gtttggcttc agtctgaggt ccgaatagta aacagcagcg agacaagttt    7920
gggtttgggt catggaggaa gccatgccag ggctggtgtt gggcacaggg aaggggcat     7980 ggcttgagac accagaccag cgtggaggct gtagtgtagt attgacctga ggacttcaac    8040
attctgatgg tgtacacacg attttttgag catgtaccat ggttatatat tacacttttaa   8100 gtattacttt aagtattact acattaatat attttgtatg ttacaataaa tacatacaaa    8160
```

```
ttaggaaaat tgaaagagat caaaatgaaa tatataatat tttcaaatta ctaatcataa    8220
tggtgtcaat ctccaggcag ggtccattgc tacagttgac gatagtggat gaaaattcac    8280
tcctcagagt cttcttgata atttgaaatt gtcttgattg acttgtcaga tctgattaga    8340
tcaacatgtt ttaaatctcg aatgtgactg acagcttgta cgaggagaag tttcactctg    8400
ccttttccct tttgttcact tgactgccat tatttctatg cttccaatct gtgttttttct   8460
gcacgagttg gttaagccat tacttcattt tgtgaaagtt tgttgagtta aacttaggta    8520
acttaatctg tcaatccact taattgaatt cagtcctggt aaactataat agattattca    8580
aacctgccaa ttctaaaaag acattttgag acaatcagga atctgaata  tagcatgaat    8640
atcttacgat atacaaggat tattgttaat tttgttaggt atgataaaag catggtgggt    8700
tgttttttgtt tttgtttttt aagtctccat ctgttagaga ggcacattga aatggcatga   8760
tatctggggt ttgcttttat gccagaaaaa agaaaaagta cagaaggatt atagaaacaa    8820
gattggtctc atgtgacaat catcagagtt tggagatggg cacgtagggt catcgtgctg    8880
ttctctctgt tttcgtatat gctttaaaag ttctgtaata gttaattaaa aaaaaaaaaa    8940
aacaccctgg ctgagcattt agggaggcca agtggggagg atcgcttaaa ccaaggagtt    9000
caagacgagc ctaggaaaca tagggagacc cccccccatc tctaaaaaaa aaaaaaaaaa    9060
aaaaaacttt aaaatttaac ccagtgtggt ggcacatgcc tatagtccca gctactcagt    9120
aggctgaggt gagaggcttg cttgagcctg ggagcttgag gctgcagtgg gacgggattg    9180
taccacttca ctccagcatg gcgacagag  caagaccctg tctcaaaaaa aataaaaata    9240
tttgaggtga agcgaggctg taataacaaa tttaaaaata taaataaaac ataaaggctg    9300
ggtgtagtgg ctcacgcctg taatcccagc actttgggag gccaaagcag gcagatcacg    9360
aggtctggag atggagacca tcctggctaa cacgatgaaa ccccatctct accaaaaata    9420
caaaaaatt agccgggtgt ggtggcgggt gcctgtagtc ccagctactt gggaggctga    9480
ggcaggagaa tggcgtgaac ccaggaggcg gagctttcag tgagctgaga ttacgccact    9540
gcactccagc ctgggcaaca gagcgagact ccgtctaaaa aaaatgaaa  ataaaaataa    9600
atgaaacata aaaccctgcc attagttgca atatgaagaa tatagagaaa tgcatatcaa    9660
atccttctca ttggaccaat attcccttag ggcaccttcc aaagctagga gactcaaggc    9720
tgtatgacat cctgagcaag tgaggggtgg cttctgggtg aatctgaata ttaaatattt    9780
gcagaattga aaacttcaca aagtaccttt agagatagaa tagcctagat ccatgtttct    9840
caaagtgtgg tccccagacc tgctgcctca gcatctcctg gaaatttagt agaaatgcag    9900
attctcaggc cctaggccag acctactgat cagaagctct gggcctgggg cccagcagtc    9960
tgtgttttca caagccctct tggtgattct tctgtgcatg aaagttcgag aattcctgga   10020
gctagactga ttcaaatctt gcctctgtat cttagagacc ttgggcagat tagtcaacct   10080
ctttctgcct ctgttttctac ttctgtcaga ggatgatagt acttgtttca ttaagttgtt  10140
gaaaggataa atgaattgac acacataaag agtattagct tttattatca aaagcttttt   10200
ttttgagaca gagttttgct cttattgccc aggggagtgc agtggtgcga tcttggctca   10260
ccgcaacctc cacctcccag gttcaagtaa ttctcctgcc tcagcctccc gagtagctgg   10320
gattacaggc atgcgccacc acgcccggct aattttgtat ttttagtaga gatggggttt   10380
ctccatgttg gtgaggctgg tctcgaactc ccaacctcag gtgatgcacc cgccttggcc   10440
tcccaaagtg ctgggattac aggcgtgagc caccgcgcct ggcccaaaag ctttaatttc   10500
ttaattttttt aaataaaata aataaaacta gaattgcttg ttttcttcca gctacccctgg 10560
```

```
tgattgtatt gagcattttc tggggtgtgt gttctttgct gtaatgacta ctggtctgga    10620
tgacctgtga tgagaccaga tgggcagggg cagtggagga gattctagag atatttagga    10680
gataagtcag ctgtacttga tgaaaagagt ggggagttaa ggctggctgc agatgtatga    10740
tttggcatag agaggtgcca gttcctgaga tgagagacag aaggggaggg acaggttgtg    10800
aggatgaatg aacaatgata tgttcattct gggcttggag ttaaggggcc tatgatatgc    10860
ttaggggaag cagagagtat caattaccta ttgctgcata acagccaccc caaacttagt    10920
ggcttaaaat agtaaccttt taatttactc atgatcatga ttctgtggtg caacaactgg    10980
gctgggttca gctgggcagt tcttctgtta gtttcaccca gggtcattca tgcatctgca    11040
gtttggggtg ggatggcctc agatgacctc attcacgtgt ttggcagttg gtgattcact    11100
gggggccatt actgtaacaa tcgcctacca ggcagagctt ccctaaggct tccaaactag    11160
gagactatcc tgggtcctgt gctgtggata ccactcagtc ccccatcccc accccatatt    11220
cctcaaaggc agagagaggg gctactagaa gacagaggag ttttcccagt gacatgtaaa    11280
cactccaaac cctggcacct tccacactgc agctttggtc tgccccttttg ggaaatctct    11340 gttttttcttc ccaggctgct ggaggggtga gagtcgccgg tagagtagag gctgtgggcg    11400
aggaggtggc ggcctcctga ggctgcagtg gtctttccag gcagcagtgg gagcacaggg    11460
tggaggtcaa ccctagagcc tgggagagtg aagctgggtg tgacttcaga gctgttggtg    11520
ctgaagtttc tgcaggccag aaggaggggc aagagtggga ggggcgcag atccagaatc    11580 acggaggcag ctgaccggag gaggcagctg cccaagggga tggactcaga aggccaaagt    11640
gctgttatcc aaacgaactc tttgcaagtg gtctctttgc aacaggcctg ggggagagca    11700
gtcttgccta aagtcacacc gctaatcagc ggccggcacg gggtaacagt tactaacact    11760
cactacgtac ccaatgctgg gcgaagtgac ttgcatgagc cagcgagctc aatgctcatg    11820
gcaatcctct gagcagctgg cattgtttca tctcaattttt acagctcagg aagctgggac    11880
acagaggaag agccaggctc tgaacactga caacctgatt gagagaccca cactgttcat    11940
caccgttacg ctatatatgc tgtatagaaa ggcaggatgg cataatggtt aaacctaggt    12000
aggtagggtt tgaatcctcc tgctaccatt tactagctct gtgacttgga ctagttatag    12060
cacctctctg tgcctccctt tccccatctc taaaatgggg ataataaatc gtacctccta    12120
cctgaggctg ttgtgggcta agtctgtaag gcacgtagaa cagtgcctgg aacgtggggt    12180
actgtctatc tgtgtgcctg ctgttacaac aatggtgagt attgccttat ctctcgctgc    12240
tgaactacca ggttagactt cttttctgcaa gtcatgagcc tttcataaac ttttcctgaa    12300
ggctttccgt agaatgtaca attcccctct gggtccaggc atgggcgccc gggtagcaca    12360
tccacttctt atcacccctg aacacccttag agcccatcag cttatcaaac cagcagctga    12420
tgtgagtgca gagcagactg tgagaggtgg aggctgatac cagtgaggat gctccaagct    12480
gggacccagc cctgaagcgg gagcccagat aatggatggt tggaaatggg cctggagccc    12540
aggagaagtg ggaggatgag ggggcagggg gaggagaagc ctgaaatcaa atgttatttc    12600
ctgaccagtt tggggtgcat gagctctgtc aacagctcat ggaaactgct gccctaattt    12660
catcttgttg gctgaggcac aattcctctc tcagggacag tgtagagcct tggggaggaa    12720
ggccctgagc gcgtatacct ggaatcaggg aatcgggatc aggggcagca gctgtgccca    12780
ataaagcccc cacccaggat cctctgactt cctcatctct tttttttttt ttttgagctg    12840
cagtctcact ctgtcatcca ggctggagta cagtggtgcg atctcggctc actgcaacct    12900
```

```
cagccttctg ggttcaagcg attctcctgc ctcagcctcc tgagtagctg ggattacagg    12960
catgcgccac catgccaggc taattttttgt attttttagta gagacggggt ttcaccatgt   13020
tggccaggct ggtctcaaac tcctgacttc aagtgatctg cccacctcag cctcccaaag    13080
tgctaggatt acagacataa gccactgtgc ctggcctttt tttttttttt ttttttgtaa    13140
acagggtctc cctctgtcac ccaggctgct ggagtgtagt ggtgtgaccg cagctcactg    13200
cagccttaac cttctaggca caagccatcc tcctacctca ccctcctgag tagctgggac    13260
tacaggcact cgccaccacg cccaagtaat tttgtatttt ttgtagagac aaggtcttgc    13320
tatgttgcct aggctggtct tgaactcctc agctcaagca atcctccctc cttggcctcc    13380
caaagtgctg ggattgtgct gggattacag gtgtgagcca ccatacctgg tctgacttcc    13440
taatctttag ggccccaact ctgcccttat ccaggcaact ctcctctccc catcttccac    13500
taacttcttt ggaatattcc agagctgtaa aagccttaga gagtatcaag tccaactcct    13560
atgtgttaca gacagggaaa ctgaggccta aagagggtaa tggacttgcc taagatcact    13620
tagtgaggtg agagaagaaa gagctagaga cagcctagcc tgtgcaagga catagttcca    13680
ggcattcaga gctgggctct gctgccggca tgtttggggc ctggtagtta gttcactgct    13740
gaactaccag gttagatttt cttctccaa gttgtggagc tttcataaac ttttcctgaa     13800
ggtcttcctt acaatgtaca attctcctct gggcccggtc atgagcgccc ctcacaggct    13860
ctctctggtc cccttctgta aaatgagagg aaaatggaag aattgctcta ctcatggaat    13920
cttcaataag tctgggccct atgcatatag cattgctaca aaatggcaga tgcactttaa    13980
caatcgtgtt taataaaagg ttggatttgc atatctgaag tggggcatgc agtctccaac    14040
tgaacacaag cctcactgct cccgcatgtg cactgcacct tcatatacat atttcctgct    14100
tggctcctga gggaatttga gtaatcccaa gaggaacccc tgtagaaaat gtcccctggc    14160
cacacacccc cattcctaag gatgcaagca ggagatagaa acattccctg cacctccctc    14220
cttgttgtca gaagaagtgc aaagagttga atccttccta atgcccactt ctcacccacg    14280
ccccaaatcc ccaggtccca tggaggtcct tgggggcctc ctatatcctg gtggtgtcag    14340
gttgatttgg aaatgtcagt gtcctccctt gtcctctctg gcagaccctg ggtatgtgta    14400
tgtttcaatg gaagtgaatt taaatgtact ttataaatca aagcttttt ctgagacttt     14460 ggagagttcc agtaatgaga gcttctcatt gttatcaagg ccaggctgg agaccagtgg     14520 caggtgagtt cctattgctg tgattgtcat gatgatgttg atgaacagtc actatttatt    14580
gagcgttctc catgtgccag tcactgtact aaacattatt tcctttggat ttcccagaaa    14640
cctctcaggt gggtctaatt acccttattc agctgataag gaaagtaagc aacttacaag    14700
accacagggc tatgaagtgg aaacacataa attgatattt cattttatt  atttatttat     14760 tttgagacag agtctcactg tgtcgcccag gctggagtgc agtggtgcgg tctcagctca    14820
ctgcaacctc tgcctcccgg gttcaagcga ttctcctgcc tgcctcccga gtagctggga    14880
ttacaggtgc ccaccaccac atccagctaa ttttttttgta attttagtag agacggggtt   14940
tcaccatgtt ggccaggcta gtctcgaact gctgacttca tgatctgccc acctcatcct    15000
cctaaattgg tatctttata tgtccaaaag agtcaactgg tggcaattta gtgaggttta    15060
atctaatagg aaatgataga gctgggatcg aacagagcca tgtgaactca aaacctatgc    15120
ttccccttcc accttttgta aaaacattgt ctaggctggg cacgatggct catgcctgta    15180
atcccagcac tttgggagac ggaggtgggt ggattacatg aggtcaggag ttcgagacca    15240
gcttggccaa aaattagcca ggcgtggtgg cgcgcgcctg tggttcccac tgaagcacag    15300
```

```
gaggctgaag cacaagaatc acttgaaccc gggaggtgga ggttgcagcg agccgagatc   15360
gcaccactgc actccaacct gggcaacaga gagactctgt ctcgaaaaaa aaaaattgtc   15420
tacatgctgg ttgcagaaaa tttaaacact aaaactaaaa aagtaaaaca cctcccaaac   15480
ttagagacaa tattaatgac ggaaaaaaaa ttcttcaaga tctctctctc tccagtcatt   15540
tattcatgtg cgaaaacagt tggtgattat tgataaaata gcttttagag tttggagcaa   15600
ttatgtgcat tacatatacc atttgattct ggcaacctaa tgaaggagta tgatcatttc   15660
ccctatttaa cagacaagaa caagaagagg gagggcagat ggtgtggtag tctaaggcac   15720
aggctccagc agattatcta ggtgtaaatc ttggctgtag gccaggccct gtggctcatg   15780
tctgtaatcc catcactttg ggaaccgag gtgggcagat cacttgaggt caggagttcg   15840
agaccagctt ggccaacata gcgaaacccc ttctctatta aaaatacaaa aattagccgg   15900
gcacggtggc aggcacctgt aatcccagct acttgggagg ctgaggcagg agaatcactt   15960
gaacccagga ggcagaggtt gcagtgagcc aagatcttgc cactgtactc cagcctgggt   16020
gacgagtgaa actctatctc gatattaaaa aaaaaaatct tagctctacc caccggggca   16080
agttacgtaa cgcctctgtg ccttggtttt catatctgta aaatggtgac agtaacagca   16140
cccacgtcaa agtgtggttg tgagaacgaa acaagatagt ctatgtaaag tgattaaaac   16200
agcgtaggca catggtaaac gcttaggaaa tgtaggctgt tataaagctc agagatgtta   16260
agtaactaga tcaagatcac acagttagag ggtgccagag tcctgatttg aacccaagtt   16320
tgtctcgttc tggagctcaa gctgctaacc ctttttcaaa actggaatta aaccaaagtg   16380
ctcaccctcc gctttgctgg gcccctccct gccctcaggt gcgtctcttc cactcacctg   16440
ccacagcagc ctctgctcag ggtctgagac cgggaaaggt gagggctacc caggtggccc   16500
tgatgttttc tgccagccag ctcaccaggt ccctcgcagc aggcggcaaa gggagggagg   16560
tttgctgtga agattatgtg gttcccaaca caagagcgc tgggcctatc tctgccctct   16620
cttttctgtg tgtcctggga caagtcactt ggcttctgtg gcttcatttt ctcatgtgcc   16680
cagccagggg gttggccctc atatgcaata acagcagcaa tgaccttt ac tgagtgtcca   16740 tgtgcgtcaa gcacgtgtgc tttacacttg ttcttattat taggtttaat aatagaataa   16800
ttgccacatt tactgagcac tcattatggg ccaggccctg ccctaagtgc ttaattagct   16860
ttagctcctc taatccttat cttatcccca cacggcatgt tatgttatcc ccattattca   16920
gttgagaaca ttgaggctca aagaggcaaa gtaacttgac caaatacttg taaacgatct   16980
tgcatgcccc ttccagctgc catttagtaa gactctaatt tcataccacc ctaaatctcg   17040
tctgcttccc cctcgtcctt ctcgccatct ccccaccgag cagttggcca agatctgacc   17100
gtgatgcgcc ccattggctt gggcttcctc acctcgagtt tccggagaca cagctggagc   17160
agtgtggcct tcaacctctt catgctggcg cttggtgtgc agtgggcaat cctgctggac   17220
ggcttcctga gccagttccc ttctgggaag gtggtcatca cactgttcag gtattgggat   17280
ggtggctgga tcacttctgg gtcatagagg gaatggaccc cgaaaggaca ggttccagaa   17340
gatctgggat attgccccct ctctgtctag caccagtgct gtgcaatatt taggacatcc   17400
ttatactaaa agattattca ttgtttaaaa ttcaaattaa ctgggcatcc tgtatttac   17460 tggacagccc tactccgtgt atcacaagga atccaggcct acattcctcc tgcatccttt   17520
ctttcctgtt attgtcgatt atgattttgt aaagttacat aatcaatata agtttatgga   17580
aaacgtaaga aggaaacacg ttagacagag agaaatagac atgccacacc tagagagaca   17640
```

```
ttctattttt ttttttttttt ttgagacgga gtttcacttt tgttgcccag gctggagtgc   17700
aatggcgcta tctcggcaca ccacaacctc agccttctgg gttcaagcga ttctcctgcc   17760
tcagccgcct gagtagctgg gattacaggc atgtgccacc gcgcctggct gattttgtat   17820
ttttagtaga datagggttt ctccgtgttg gtcaggctag tctcaaactc ctgacctcag   17880
gtgatccgcc cgcctcggcc tcccaaagtg ctgggattac agacatgagc caccgcgtcc   17940
agcctgagag acattctctt gaaagaaag gactttcagc cccctaatgc tgctagacaa   18000
taaatagcca tgccttttatt ttcattaaat tacctgtgct ttgtttacat gcatttgtgt   18060
gaaatgctaa gaaccatcac aactaatgta tggtgccaga agtcagaata gttgttacct   18120
gggcaggagg tggatattga ttaggaagga acacaaaata accgcatggg gtgcagaaaa   18180
tgttctctat gttcacctgg gtgatgatta cacatcaagc tatacacgtt ttaaagggc    18240 attggcactt aataggagga agtaggctaa atttttttcct gaaacattgt tttgttttgt   18300
tcaaacctct gaatccctgt gctgcccaga tgatggtaaa cgtcatccta ggcatcttag   18360
ggacctctca aggccattcc agcctcccct tctaagaccc tgctaaacct ctgggcactg   18420
ctgttaaaca tttctctatg agccaggaac tgtgctgagc actccacaaa tattattttg   18480
tttaactctt ccgggtaggg atctaacctg gtatacaggt aaggaagtgg aagctcagag   18540
agggcaaggc acttgcctag ggccacacag ctaagtggtg gagatggctc aacttttta   18600 ttataacctt ttccacatgc tccagagtgc tcagaacatg aaacacagtc tagccagctc   18660
ccgattggcc ctggagggaa aaaactttat atattttttct tttttaaaag gtttagaggc   18720
tgggcatggt ggttcacacc tgtaatccca gtacttttgg gaaccgaggt gggcagatca   18780
cttgagccca gaagtttaag accagcctga ctaacacagt gagatcctgt ctctgcagaa   18840 aatagaaaa tcagctaggc gtggtggtgt gcacccacag tcccagctac ttgggaggct   18900
gaggcaggag gatcacctga acccagtgag gttgaggctg agtgagccat gatcgtgcca   18960
cttcactcca gcctggacaa cagagtgaga cccctgtctca aaaaacagtt ttaggggccg   19020
ggcgcagtgg ttcatgcctg taatcccagc actttgggag gccaaggcgg ggggatcatg   19080
aggtcaggag atcgagacca tcctggctaa ctcggagaaa ccctgtctct actaaaaata   19140
caaaaaatta gccgggcgtg gtggtgggcg cctgtagtcc cagccactcg ggaggctgag   19200
gcaggagaat ggcgtgaacc cgggaggcgg agtttgcagt gaaccgagat ggtgccactg   19260
cactccagcc tgggtgacag agcgagactc cgtctcaaaa aaaaaaaaca aaaacagttt   19320
taggccaggc gcggtggttc atgcctgtaa tcctagtact ttaggaggcc tagcaggtgg   19380
attacctgag gtcaggagtc cgagaccaac ctgagcaaca tggtgaaatc ctgtctctac   19440
taaaaacaca aaaattagct gggtgtggcg gcaggcacct gtaatcccag ctacttggga   19500
ggctgaggca ggcgaatcac ttgaacccgg gaggcggagg ctatagtgag ccgagatcgc   19560
accattgcac tgtagcctgg gcgacagagt gaggctctgt ctcaaaaaca aaacaaaaca   19620
aaaacagtct atgagttaat tcccaccaga attcaataca cacacgcaca catgcacgca   19680
tacacacact gtgtccacct gggaagtgac aaagggcacc ctgggggatt tcaaatggtg   19740
gtggccctgg tttggtgttg ctgccttagc ttaaggtcac accagccttc agcctcctgc   19800
cccacagtct agggctgctc ccctcatctg atgtccacag ggacctgttt gttcttgact   19860
caatctagaa agacgagaag ggagagaagt cactcgcagc ctgagtgaac tcccctgccc   19920
cacccctgac tgcttggatc cccctagggg tgacccctgc tgaaactggc tccttcctga   19980
ccggttcccg tcagggctgt gctgatgggt ggtgcccagg cctgcccctg ggacgggt     20040
```

```
actctccctt ggcaacactc cagcttgtgc cacttgactt gggactgatt tggttctgtt    20100
ttgagtccct tcaggggagg ggcctatctt attcaacgtt gttgtttgtt ttcctcacat    20160
actgataact tagcaaatgg ctattggagc aaaaatgaaa ataaacggaa ctctgaagtg    20220
ggatgtttta aaattttatt tatttttta gagacagggt cttgctctgt tgcccagtct     20280
ggagtgcagt ggtacaatca tagctcattg cagcctgtgc ctcctgggct caagtgatcc    20340
tcccacctca gcctcctgag ttaaattttt ttacaggcgc ctgctaccat gccctgctaa    20400
tttttgtatt tttagtagac aaggggtttc accaggtggg tcaggttggt ctggaactcc    20460
cgacctcaag tgatccacct gcctaggcct cccaaagtac tgggattaca ggcgtgagcc    20520
actgtgtcca gcctaaaact gtttttgaga cagggtctca ctctgttgtc caggctggag    20580
tgaagtggca tgttcatggc tcactcagcc tcaacctcac tgggttcagg tgatcctcct    20640
gcctcagcct cccaagtagc tgggactgtg ggtgcacacc accacgccta gctgattttt    20700
ctattttctg cagagacagg acctcactgt gttgctcagg ctggtctcaa actcctgggc    20760
tcaagtgatc tgcccacctc ggctctgaaa agtactggaa ttacagcctc ctgagtagct    20820
gagaccacag gcacacacca ccacacctag cttttttttt ttttgctttt tgtagagatg    20880
gagtctcact atgttgccca ggctggtctc aaactccagg ccttaagcaa tcctcccacc    20940
tcagcctccc aaagtgcgaa gattacaggt gtgagccacc attcctggcc ttaaagtgt     21000 gatattttta atgtattttg aaatctgcag gactctccct agaagataat agcaataacc    21060 aactcctttta ttgtgcttga cgtatatcaa ctcactttgc ccttaccgtg gctccagagg   21120
cattgggtcc accttataaa tggaggcacc aaggcacaga gtgattaaat aaattgccca    21180
ggatcacaca gccagaaagt gtctgagtca agattccagc ccaggcagcc tagacctgag    21240
agcacgctcc taaccactgc acatcactgt cttagcacct cctcagcaca aactggccct    21300
tgaggaatga ataccgccg ccggcacaca cgctcctgag ttaagccttt gtcaatgaaa     21360
tgaacaccca cttaaaagga ataacctgtc caggcacgat ggaacattga gtaacccctt    21420
attctaaatt cctggtccct gtaagactcc ttccccatgc ccttgccctt ttctgacctt    21480 ccectaaagt ccttgaggct taagcgggca tagtctgcag caaacactgg ggaagctgag    21540
tccagacttc agagcacagg ctttggatct aggccagctg gatttgaacc tcacatttgt    21600
gatcagctgg catgactgtt tccaaaaagt ccatttaat cctctacgtg accctctgta     21660
aaatgggata ctgaatggtg agctagcacg attttacaga gagtgaattt tttttgtgtg    21720
tgtgtgaggc agtcttactc tgttgcccag gctggagtgc agtggtgcag tctcggccca    21780
ctgaaacctc tgcctcccgg gttcaagcga ctgccatgcc tcagcctcga gagtggctgg    21840
gattacaagc atgcaccacc atgcccgggt aattttgta ttttagttg agacagagtt      21900 tcaccatgtt ggccaggcca ctcttgaacc cctggcctca agtgatccac ctgccttggc    21960
ctcccaaagt gctgggagta caggcatgag ccactgcacc cagccttata gggttaaaat    22020
ttaaaagagg tgatgctgtt acaagcctgt tttacaaaat gctcttataa taaatcatta    22080
tcatcactgt tgctgtggtt gtagcatcat catcattaac tcccagaggg aggagggagt    22140
ctcagagcaa gctgctcagg ggagactgga tgtccatgga ttgtccagct cagtaccact    22200
tcctccagga agtcctccct gataagtcca gtcagcatca ccctctcctt ccaatgaacc    22260
ccactagcct tgtgatatca cagatattct tagttgacag gctcatggtg tagcctgtct    22320
agatcataag tacatttttt ttttttttgg atcataagta tcttcaagac caaaataatt    22380
```

```
ttctactcct gagcatgctc attggtcaaa ggaaggaagg aatcataata gcgttaataa    22440
ggctagcgtc ttttcagaag ttggttcttt gtgccagtct tggtgctaga cacaccgata    22500
ggaagaatac tccttcacat ccccaggaca ccaacatggg atacgtttga tcatcattct    22560
taatttgcag aaggagaaat aggctcagtg agatgaaata gccactccag tggcaaggct    22620
gggactggaa gccgggcttg tcctgattcc aaatccagtt tctttccact gccacggaga    22680
cggagagaag ggacagtggc cccagatggg gatggggtga ctggatgtgg gcaggcctgc    22740
gggggaagag tgccctctgt tgagcatccg aatgatggca gcagaaaaga agactgggca    22800
gaatcccagt tatcagatcc cctgagggaa cagtcacccc gatcaccctc agtcagatga    22860
gtgtgtgtag atcaatgcct catagatgaa ggcactgagg cacagagtgg ttaagtcatc    22920
tgccagacca catggctcag ggtgcagagg ccaccttaac gggagaagag atggtcactc    22980
cactctgcag catcagcgcc caggtgggta gaaatcttgt cttctattcc cacagaaagt    23040
aggtgcccaa cagtgtttgt tgaaagaatg aatgaatgaa tgaatgaatg aatgaatgag    23100
tgagaggcat ccttccttct cagtcgtcct ggctctccct ctctccccca gtattcggct    23160
ggccaccatg agtgctttgt cggtgctgat ctcagtggat gctgtcttgg ggaaggtcaa    23220
cttggcgcag ttggtggtga tggtgctggt ggaggtgaca gctttaggca acctgaggat    23280
ggtcatcagt aatatcttca acgtgagtca tggtgctggg aggagggacc tgggagaaaa    23340
gggccaaaag ctccatttgg tggggtttcc agggttttga aaaataaaga caacctgtaa    23400
tcccagctac ttgggaggtt gaggagggaa gatcacttga ggccaggagt ttgagaccag    23460
cctgggcatc atagcaagat cctcatctct aaaaagtaat tttttctaaa ttatccagtt    23520
gtggtggcat gcacctgtag tctcagttac tcaggaggct gaggtgtgag ttggaaggat    23580
tgtttgagcc caggagttag ggaccgagct gggcaacata gcaagacctc atctctaaat    23640
aaataggtag gtggatagac agatagatag atagacagac agacagacag acagacaggc    23700
tgggtacagt ggctcacacc tgtaatccca gcactttggg aggccaagga gggcagatca    23760
cctgaggtca ggagttcaag accagcctgg tcaacatggg ggaacctcat ctctactaaa    23820
aatacaaaat ttagctgggc atggtggcag gcgcctgtaa tcccagctac tcaggaggct    23880
gaggcaagag aatcgcttga acccgagagg tggaggttgc agtgaaccga gatcgcgcca    23940
ttgcactgca gcctggggga caagagcaag acttcatctc aaatttaaaa taaagaaaaa    24000 agaaagaaa agattgatag atagatagat atccaaatga gtttacaaaa atgtggtctg    24060
tgcaaatgtt taaacacaac aaaccaatgc ctttaactac tacagtataa tcctgtagga    24120
ttgtgctatt catgatataa ttatggttat ataaagtaa ttaattctca gagcctcacc    24180
agcagtgggt ccagcaagtt tgtacagcca gcatcttctt tcagtcagtg cgtgtcagta    24240
actgcatatg tcctctcatt gggagagcct gtcgaaagtc taaatttgaa ggcagctgtg    24300
aaggtaaggc caatccaaat ggctctccca gatcctctgc tgtaaccctg accctgagtg    24360
aggacatagc caaccttccc atctcatagg tgagaaagct gatgcctgga gagggaagg    24420 gactgcccaa gatcacatag caagatagtg gcagaaccca agcgagaacc cacagttcca    24480
gcctggctta aagaaagtg cactggactt ggagtcaaag gctggggttt gcatcccagc    24540
tctgccataa atccctgtgt gactctgggc aatttaacct cttagagctt tagtttcttc    24600
atctgtaata tgagggtagc agtactacca catagggttt tgagggagta attgaattaa    24660
tcacatgaga tgatgcatgt ttacaaaaaa aagcatgaag cccctttact gtgcctcagt    24720
gtcccaaagg actttggatt ttactctgag aaatacaggg agaactaggg agtgttgggc    24780
```

```
agaggagagc catgatctga cttatgtttt aagatactct ggcttctggg ttcagaaaag   24840
actgaagggg caagagagga agcaggtgga gaccagagcg gcagtgattg ccatcatcca   24900
gactcagact aggacaatag ctgtgagagt gatgggaagt ggttggatcc tgactgtatt   24960
ttaatagcag aattgacagg atttgctgat agactcacg tggggtggga gagggtcaag   25020
atgacttcaa ggttctcatc tggcacaact cagcggctgc tggtgccatt tactgagatg   25080
gggaatgttg gggtgggata gatctgggag ggaaaaccca gagttcagtg tcgaatgtgg   25140
tagcgttagg gttaaggttg ggggaggggg ggtagagatg tgtatgaaac atcccagtgg   25200
agacactgaa tggagatgta caagtctgaa gcttagtgga aaggttaggg ctagggatat   25260
aaatttggga gttgttacaa tacagatggt gtttaaagcc atgagaccca aggagatcac   25320
tcaggagtga ggataaagag agatgggaag aagtctgagg actgagtcct agaacaccct   25380
gcattttaga gggggacat gtgtaagagc cagcaaagga gacagaattg tgcttggaga   25440
ggcaggagga agcccaggag agcgtgaggt cctggaaggc aaggaaagag agggccccag   25500
gtgggctgaa tgctgctgag aggtcaagtc ggatgagggc tgggaagtag ccattggatt   25560
tggccaggag accttggcat gcatggttgt agaggaggat gaaggcaaca gcctggcttg   25620
actgattcaa gagcaggaga tgagaaagtg gagacagcat gcaggggcag ctctgccaag   25680
gactttgcta taaaggggaa cagagaaatg gaggagaagc aggagggcaa taatccgata   25740
gagaggaaaa atctgatgat acagaagaga gatgaactgc aagagtcaag cctttgagtt   25800
ggaaagcagg agtgggattt tgagcactga taccctttagg ccgatgcagg gacagttcat   25860
cttttttttt ttttttataca acattttatt taaaaaaatt attttcatag aatacatttt   25920
cacattagag attcccattg tgcggaaata acaatttatt acttatagtt ttatatttgt   25980
ggacagattg ttttagaaca agtagaatac atttgagaat taaatctcag tttacaatgg   26040
ataatatttt gatatgtctc tggggaaact tgccttaaa tggaacttct gtatcttcag   26100
aagcactcca agcgtttctt cctaggattt agaaatttat aatatgagat agcagcattt   26160
cctaatttta aaatttccct agtatatgta accatcagta ggtggtatct actgactaga   26220
gagggaagtt tttgaaaatt aaacactgtc taattttctg caaagttttt attcatgaat   26280
taagagtatt tcccttttgtc cattattccc aaggcaaata tggaaatttg atcatgtact   26340
aatcataata aagctggatt ctctttaaga gattgagaaa ttaaaaggca aaagctgata   26400
tatcatgttt agttatattg tgagtcttat aagaagctgg gaggcaaccc cattaactca   26460
ccagaataca gaactcagtc tcacaactta gatataattc ctctcaaacc ttttcctcaa   26520
agattaaatt ctgaaaataa tcttgtgatt aagagaagaa ggctgtccac caatgggctt   26580
atctgttatt tcttccttat tgtgagctta atggcatgac aaagcagagg caagaggca   26640 tacatcaatt cttcaaagta ggaagtcaaa aaggtcagag cttccacagc atggcaacag   26700
ctttgcagat gcccacatcg tgatagttga aatagcaaag cccagcaaag gttaaagctg   26760
aaaatgccaa aagccctgcc ttggcagctt tctgcgaggc atccccatga acataatcag   26820
taacaacttg tccaaggccc cagtgaccat gaagagtgag ggctgcagcc agggaatagt   26880
ccgtcgcaga gcaaggattc aaataagcag ccggaagcag acccgggagc aaaacactga   26940
caaccctctc gctagtccag tggagagatg cagccttgga gccagaatgg tggctcggtg   27000
acaagtgtat gtgctgcact ccacaccatt ctgggatagg tcggtcctga agaaatgctg   27060
agatatgagc aggtctgacc actggagttc gcagcaacag agctcggcct ccttgggcac   27120
```

```
cgcaaacggc actcagcctc cagggaaccg ccatctcgtt cctgaggcgg agagttcatc    27180
ttaacgagag aaatggcagg gactgtgaat aggccggcag atttggtggc gggtgccaca    27240
ggttcagtct cctgcaggga gaggagaaaa tgccttacta attccttgta ttttctcaga    27300
gaaacaagag gcaccgtcat cagcctcatg tgagggtggg aaggagggat ggggtttgcg    27360
gagagggaaa gtgtggtatg gtcatctgtg ggagtggaag agagtgagag ggctgcaggg    27420
gtgcagcggg actgcaggct ggcaccaggg tccctagggc ttgtagttgg tggaaagtgc    27480
atcagtgacc agggctgtgt gcagctgctc caggcaggtg tggaagaagc agagttgaac    27540
ttgcccagcc tggagtgctg cccagagtga gcccaaagcc caggggagac cagagatggg    27600 gctgttttgca aaggaggaag tataacagta gcccacaaaa tctgagctgg ttaagaaagg    27660
agagagagtg aaaatgggga gcccagcctg gcagcctggg tacacatctc agctcaaccc    27720
acactagctg aatccatttg ggcccccttcg ttgacctctc tgtgcctcag tttccctatc    27780
tatagaatgg ggataagaat aaggctactt cctagggctg ttgtgaggat tgaacaagtg    27840
accgaacact tgttcaattt tgaacactgt tctaaagcat ttaggacagt gcctggcatg    27900
gggtaagtgt tgcggcagtg ctgttatttt catcatcacc attgttctca ggctgcgttg    27960
attggagctg ctgaagggag gcaatttaag gaagtgagcc ggacagatag gaggtggtgg    28020
tggttatcag gtgcgatgct tgaaactgag gcttcggagg caacagttac tggtaatgac    28080
aaggtctaag gcttgacagt gggtggcaga agtgtaacgc agggaaagag acgagcggtc    28140
aaggagccga gagggaagga gttgggtgga ctaagatcat ttgtggaaga atgatggaga    28200
gaaaggctga agggcagggg ctgacatcat cagtgaccaa gaggcggccg ggaggctgag    28260
accacagcaa gaaagggaga gtgtgatggc atcttcttca agggagctgg ggatgtttgg    28320
ggtgaaaaaa agaacaatgg tctgggaggg aatatgggaa attttttttt tttttttttt    28380
tttttttttt gagatggagt ttcgctgttg tcatccaggc tggattgcaa tgttgcaatc    28440
ttggctcact gcaacttctg ccttccaggt tcaagtgatt ctcctgtctc agcttcccga    28500
gtagctgaga ttacaggcac acaccaccac gcctggctta cttttgtatt tttagtagag    28560
acggagtttt gccatgttgg ccaggctggt ctcaaactcc tgacctcagg tgatccaccc    28620
gccttggcct cccaaagtgc tgggattaga ggtgtgagcc accgcgccca gcctggaagt    28680
ttgtatttat taattttggg ttgtcttcat ctgtgtatgt gactttaacc cctaaatact    28740
tcagtgtaca tttctttttt tttttttctt tgagacagag tcttgctcca tcaatcaccc    28800
aggctggagt gcggtggtgt gatctcggct cactgcaacc tccgcctcct ggattcaagc    28860
aattcttgtg cctcacccctc ccgagtagct gggattaggg gcatgccacc atgcccagtt    28920 aattttttgta ttttttagtag agatggagtt tcaccatatt ggccaggctg gtcttgagct    28980
cctggcctca gttgatccac ctgtctcagc ctcccaaatt gctgagatta caggcgtggg    29040
ccaccataac cggcctcagt gtatatttct gatgcagttg ggttctgtat ccccctccaa    29100
tctcatctcg aattgtaatc cccacgtgtt gagggcatga cctcgtggga ggtgattgga    29160
tcacaggggt ggtttccccc atgctgttct tgtgacagtg agtgggtttt caggagagct    29220
gatggtttga aagtgtggca cttcctctct ctctttctct ctctctctca cctgacacca    29280
cgtaagatgt gccttgcttc cctttcacct tccaccatga ttgtaagttt cctgaggcct    29340
ccccggccat gccaaactgt gagtcaattc agcctctttt gtttataaat tacgcagtct    29400
caggaagtat cttttatagca gtgtgaaaac agactaacac aatttcctaa aacaagggga    29460
cattctctta cataacccttt tttcagttaa caaaaatgag aaattgacat tgatatatta    29520
```

```
tgattacctt attctcattt caccaatttt ctcaataata tcttttctag aaaaaaatat    29580 atatttttg tggtcgagga ttacatcttg catttagttc tcatgtctta ttaaattcca     29640
tcaatctgga gcagtttctt catctttctt tatctttcat gaccttgaca tgttttgaag    29700
tttcgagcca gttcttttgt agaatgtggg tttgtctgct gttcctcatg attagattgt    29760
gggtatgcat ttttggtagg aattctccaa gagccgtgtg tgcccttctt agtatatcat    29820
atcagaagac atgctatcaa tttgccccat tactgggtgt gttaactgtg atcattgggt    29880
taagatggta cctgccagga tcttccactg caaagttact attttcccct ttgtaattaa    29940
taaacatctt gtgaggagat aatttcctat agaaatcctg ttgatcatcc aactttcacc    30000
cactgatttt agtgttcatt gattcttccc tgaataaatt agtactataa taattgccaa    30060
tggtggtttt ctaattccat ctttccttca gtagttggca ttcttctgta aggaaaagct    30120
ttcgcttctc tgttcatcca ctcatctatg tacttattta tatcaccatg ggctcctgga    30180
ttccggttta cacacttcca ttttctgcct tttctctctg cttaatataa ggattaatga    30240
gaactccctg attcccagga agaaaatgtc agcagagctt tcttaggcgg aatgaagaga    30300
attcagtgta agaaccataa aggtgtatct gtgtagtatg gacagttta aaaacaaac     30360 aaacacaaag aacctccaag ggcaggaggt gctgccagac tcaggagggc actagaactg    30420
gctatgagaa gccactgaga tcccaggtag tctgtgctct ccatcttttg gctcttattc    30480
tctccgtaca tctaacatct ctgtacacca gctttctctt tagcgaaaaa cgtgtcccct    30540
ccacccaccc atccacctcc acttgttcct gcatttctat gtcccagatc ctgcagaaaa    30600
caactctttt ctctcagtta gtctcaattc tgtagtccag ggagagagaa tctgatcagt    30660
cccctgggtc attttttccac tctggtccaa gcagctacag ctggcatggg aaatagttca    30720
cacagtaaaa acatggctgt caagaagagg agtaaatttc agaggcagaa cactccctgt    30780
gagcccgaac ctcttcctgc tttgttgcag tcttcataac gattgcttta aaagactgca    30840
ttgatataac atcatctctc ttctctgcat ctttgacttg ctagcttaac tggtctagag    30900
gagggcttag cactgatttt gagtattcat tttcctcaaa acttcaattc agcctgggtt    30960
tcttcagcag gagggcccgg gggaaccaga gccagggacc agagtcattt cagtgcacca    31020
gctcaagaaa tgaatattcc aggccaagaa tccccaagtg ttcttcctga actccttcct    31080
ggtggagttc aaagagatga aaacacaag cccgcttttc agttcttatc aggaaactgc    31140
atagactttc ctcttatgt atgactgagg gcttttacc atcatttgtt cccttcacaa     31200
atatttattt ggtatttact atataccagg gactcttgtg gcagtggaaa atacaactct    31260
catggaacgt ctgttccaga aggaaagact gccaataaac aataaaatag gcaaaagata   31320
tagcatgtta gagagtggta agtaccacag ataaaaatga aatggagaaa agaaacacga    31380
aaagttgggg agagaggata actgtttgag agggtggcca ggggcagctt catcttatca    31440
agagggtgat tttttgagta cagacctgaa ggtaacgagt gcacaagcca tatgggtacc    31500
tgagaacagc ggcagaacaa tggcagggtg ctgggagggc tgtttaccag ccacgctgtt    31560
tagaattgtc agcacatggt gataaaaaaa aaaaaaaaa aaaaaaaaca ggctgggagc    31620
agtggctcat gcctgtaatc ccagcgcttt gggaggccaa gcggatgga tcacttgagg     31680 tcaggagttc gagaccaggc tggggaacat ggtgaaaccc cgtctctact aaaaatacaa    31740
aaattagccg ggcacggtgg tgggtgcctg taatcccagc tactgggag gctgaagcag     31800 gagaatcgct tgaacccaac gggtggaggt tgcagtgagc caagatggca ccagtgcact    31860
```

```
ctagcctggc gacagagtga gactccgtct caaaaataaa taaataaata aatacaaata   31920
aaaagcagac agactttta gttggcttta gaattcttag acaccctcta cagacaaggc   31980
accccgattg cttgcaccca gggtggacta ctccctccac cctgcccttg ttacaccctg   32040
gctgggggtc agcatttcag gcagctgaat gacccaaagt gggaacacgc tagtgggttt   32100
gaggatgagc aagtggagga gggcaatagg aggtgacgcc cgagaggtca ggtgagagtg   32160
gatcctgcag ggtcgtggca agaacctgga ccttgacttt gagtgacatg ggagccgctg   32220
gaggcttctg agcagaggag taacatgatc tgacttgcat tttatttat ttatttattt     32280 gacgcagtgt cactctgtcg ctgaagctgg agtgcagtgg cgacatctca gctcactata   32340
gcctccgcct cccaggttcc agtgaatctc ctgcatcagc ctcccaggta gataggatta   32400
caagcaagca tcaccacgcc tggctaattt ttgtatttt agtagagaca gggttttgcc     32460
atgttggcca ggctggtatc gaactcctga cctcaggtga tccacccacc tcagcctccc   32520
aaagtgctgg gattacaggc aaaattagaa tatatctaga atttcctgaa gaccttagtt   32580
tggtattata agaagtctgg ttgcttcatg ttgcaaaatt tatatcactc atcactcccg   32640
cagagttaaa attccgctga gaagtaggaa tcagtgaggt gcgtgtccat gtgggttttt   32700
gccacaccta agtgaacctt ggtcaaaagc atataagagc tactgatagg ccgggtgtgg   32760
tggctcatgc ctgtaatctc agcactttgg gagggaagga tctcttgagc ccaggagttc   32820
aagaccagcc tgagcaacat agcaagattc catctttaca caaaatttaa aaattggcca   32880
ggcatggttg tacattcctg taatcccagc tactcaggag gctgaggtgg gaggattgct   32940
tgagcctggg agttggagac tacagtgagc tgtggccaca ccactgcact ccagcttgag   33000
caatggagca agactctgtc tcaaaaaaaa aaaaaaagg ccaggcgcag tggctcatgc    33060
ctgtaatccc agcactttgg gaggccgagg cgggtggatc gcctgaggtc aggagtttga   33120
gaccagcctg gcaaacacgg tgaaacccca tctctactaa aaatacaaaa ttagcccagc   33180
gtagtggcgc atgcctgtaa tcccagctac tagggaagct gaggcaggag aatcgcgtga   33240
acctgggagg caaatgttcc agtgagccga gatcgtgcca ttgcactcca gcctgggcag   33300
agcctgctgg gttgggctgg gtaagctctg aacaccagtc tcatggcttc aagtcacacc   33360
tcctaagtga agctctgaac tttctccaag gactatcagg gcttgccccg ggcagaggat   33420
gccgacactc actgctctta ctgggtttta ttgcagacag actaccacat gaacatgatg   33480
cacatctacg tgttcgcagc ctattttggg ctgtctgtgg cctggtgcct gccaaagcct   33540
ctacccgagg gaacggagga taaagatcag acagcaacga tacccagttt gtctgccatg   33600
ctgggtaagg acaaggtggg gtgagtggtc tcctacttgg gctgagcaga atggctcaga   33660
aaaggctctg gctgaaaaaa tctccctcct ttaccaagtt cccctgggtg tctgaagccc   33720
ttccatcatg attcatttct ttgagtagtg tttgctaaat tcataccttt gaattaagca   33780
cttcacagag caggttcagg aggcctgggg tatgcagatt tcaaccctct tggcctttgt   33840
ttccttgtct gtaaaatgtg gttagctggt atcagcttga gagctcggag gggagacgtg   33900
acttccccat ctaactctaa gtgacaaggc tgagactctc cagccctagg attctcatcc   33960 aaaaccctc gaggctcaga cctttggagc aggagtgtga ttctggccaa ccaccctctc    34020
tggcccccag gcgccctctt cttgtggatg ttctggccaa gtttcaactc tgctctgctg   34080
agaagtccaa tcgaaaggaa gaatgccgtg ttcaacacct actatgctgt agcagtcagc   34140
gtggtgacag ccatctcagg gtcatccttg gctcacccc aagggaagat cagcaaggtg     34200
agcagggcgc tgcccttggg cagcacttgg gtctaacagg actagcacac atatttatgc   34260
```

-continued

```
ccctccccac cccagggcca gcgtgggttg ggagagggca tgccgggtgg tggagctgtg    34320
cctgcctcta cagtggagct ctaggtagaa tgctgggtgg tcacagtggg cctgggactc    34380
aggagactgt ccagtgatca aaggctttct gggggtagtg attaaatcca tccatgctaa    34440
catgaaacag acctcagttt gaaccccatt tctgctagtt gctaaagtca gtcaccatga    34500
gcgagagtca gcagcaacag actagactag aattagccag cctctctctt cccccaaca    34560 aatttcaaga atggaaccat cagaatcaga agtagagaag tatgtgacac tagccatgtg    34620
gctctggtca agccacttca acgttttgag tctcagtggc ctcatctgta aagtgggaat    34680
taagagatgg tgcatgtaaa gtgcttaacg gggagtaaat ggtaggcaaa cattagctgc    34740
tgctattagt aaagagagac gatggtgtgt gtgagtcttg tgggcagaga tgggtgagag    34800
gggagacaaa acaagttctc atgatgatgg ggaaggggc tccagctggt ggtgtcggag    34860
ggaagtctgg acagaccagt ggtggggctc gggtgggagg cactgggggg gctggagtgg    34920
aaagaatgtg gccacagatg acagcttcac agcagaattc agtgctaaga ggaagtgagt    34980
ggccatgagt tccatggtga cagaaagtct aagacaccca gcaaggcagg agtgggtgtc    35040
aactcaggga agcccagagg ctaatcctag gtgagagctg agggtgtcag ataagagcaa    35100
ggcaaggctc cggttctgga gcagtgaagg acatagcaga gctatgaccc aggaacaagg    35160
cccagcttat tgaaactggg cccagtcaca cagggtggca caggcaccaa gtagccaata    35220
ataataataa aaacaataac aatgatttgt gtctactggg catttattca tgttctatgc    35280
cagacactgg gctaagagct ttatatgtgg aaactcattt aatccttaca ataaccttat    35340
gaagaaggta catccaaaac cccattcttc taggccaggt gcagtggctc acacctgtaa    35400
tcccaatatt ttgggaggct gaggcaagag gattggttga ggccaggagt tcaagaccag    35460
cccaggcaac atagcaagac cctgtctcta aaaaataaaa caaaaaccca ttcttcccgc    35520
tgcccaggga cacaccacta atgagtgtga tgggtgccta ggatgctgag cacctggact    35580
tcccagctca ttccctaaat gctgcacaat cagggtaact gtgccctgag cctaagaggc    35640
agtagtgagc tggcccatca tgtccactga tgaaggacac gtagccccaa cacaggggag    35700
aagtggtttc aggatcagca aagcagggag gatgttacag ggttgccttg ttcccagcgt    35760
gctggtcact tgcagcaaga tggtgttctc tctctacctt gcttccttta cccacacgct    35820
atttctttgc agacttatgt gcacagtgcg gtgttggcag gaggcgtggc tgtgggtacc    35880
tcgtgtcacc tgatcccttc tccgtggctt gccatggtgc tgggtcttgt ggctgggctg    35940
atctccgtcg ggggagccaa gtacctgccg gtaagaaact agacaactaa cctcctctgc    36000
tttggctgaa ggccagcagg acgctgggac ctgatgggcc actgtgcagt gcacagctgc    36060
attaggcagg tgtcggcgca ttctcttatt ggcttcaacg cctagtgagg gatccatcct    36120
ggctcggtgg cgcatttgtt aagatgctcg ggagcaggtg gcagaaccca tttgagcttg    36180
cttgggcatt ggggagaatt tgttatcagg ctactgggt gtcacagaac tcaaggacag    36240
ggactggagt gttgtgggga gccccgaagc ccctgtttta cttctttctt tgcttttcct    36300
gaatatctgc tttattctta ctctatagac atgcttcctc ctctttcacc ccacattgtg    36360
gggtgtagtc ttttgcttca agaaagcagc ctggtggatg gaatctcttg gccccaatcc    36420
caaattctct ggagaagggg ctctttggtt taacttggat aatgttgtct tcagctgggg    36480
gtgggcacat cgtgcatatg tggctgctgc cgggaaccca cgtggatgat gtgagaggag    36540
cagcacccag aagagggagt gctgggctga tggtccaggt cgtgtccact tctgattgtt    36600
```

```
taattcttct tctaagtgga tggatctttc tccaatactc agcaaatcct gatcgttcca   36660
gaatacttca ttatagccaa ttggttataa tgtgcttctc taagagaaat atttagggac   36720
aacaaatctt catgggtttg aagacttgat ggaggaaaaa ggagtagatt ttcgaaggct   36780
ggatttggat gaacagggc tattcaggga gtgcattcca acctaaaatt aggaaaaact    36840
ggctgggcgc agtggctcac gcgctttggg aggccgaggc gggcagatgg cctgaggtca   36900
ggagttcaag accagcctgg ccaacatggt gaaaccatc tctactaaaa gtacaaaaat    36960
tagccaggca tggtggcggg cacctgtcat cttagcgact caggaggctg agacacgaga   37020
atcacttgaa cctgggagac agagcttgca gtgagctgaa atcgtgccat ggcactccag   37080
cctgggcgac agaacaagac tctgtcttaa aaaaaaaaa agtggtttat atacagagtg    37140
gaatattatt tagccataaa aagaatgaaa tcctgtcatt tgcagcaaca tggatggaac   37200
tggaggtaat taaaaaataa aattaaataa ggaaaaacgt atcaatactt cgattaacca   37260
aaaccagggc aaatctgatt ttcatctttg caagggaac aaatttcttt tatctcctct    37320
ggctttgaaa ccctgaaatg aaaggaggaa gggcagaaaa agaacacat agcaagttat    37380 catcagtctc agcgcccatc gcattccctg agcttgtttc cttgacttca tcactggcag   37440
gactattcaa aaatgattcg ctcattcatt catatattca ttcattcatc attccttcat   37500
tcaacacata cgttttaaca ctcatcttgc ttttcaagct atagtttagt gagcgaaatg   37560
gatacacaca atacagtgtg agaacagcaa gagggcacat ctgagctagc ctgggatggg   37620
tctggaaatg cttcctggag cagaggaaac ggttgacagc caagtgttga cagagaagta   37680
gtattagcca ggcagagaca tggggaatgt attccaggca gaaggcacag tgtgtatgaa   37740
agcttattgt taagaagagt gtgtggccca accaggaaac agacattcta aaggcatagg   37800
gtccacccag gagcatggtg gacccagatc cctgaaagat gggaggtgct caggcacact   37860
tcctgggcta gttgaggagt ctggatattt atttatttat ttatttattt atttatttat   37920
ttattgagac agagtctcat tctgtcaccc aggctggagt gcagtggtgc aatctcagct   37980
cactgcaacc tccacctcct gggttcaagt gattctccta cctcagcctc ctgagtagct   38040
gggattacag gtgcccacca ccatgcctgg ctaattttcg tgtgtgtatg tattttgttg   38100
ttgttgttgt tgttgttgtt gttgttgttg agacggtgtc tcgctctttt gcccaggctg   38160
gagtgcagtg cgccatctc agcttactgc aagctccgcc tcccgggttc acaccattct    38220
cctgcctcag cctcctgagt agctgggtct acaggcgccc accaccacgc ccagctaatt   38280
ttttgtgttt ttagtagaga cggggtttca ccatgttggc cctgctggtc ttgaactccc   38340
gacttcaggt gatccaccca tgtcggcctc ccaaagtgct gggattacag gcatgagcca   38400
ccgtgcccaa cctggatttt tattctgaag actaataggg attctaagga aggaaccagc   38460
ctgattgaat ttgcatatgt gtccacatct gctggctcac ggctgtgtgg gaggctgagt   38520 gatgggagg aaggattact gagtagggat ctgaaggtgt ggcctcatgc tttctttcta    38580
accagctgtg ttgtctttgg gatggtgctt aaatttgggc tagaccagtg ggtcttggtc   38640
accccccagg ggacatctta caatgtctgg aggcgttctt ggttgacaca gtggggtgag   38700
ggctgctact ggcagctcgt ggggagagac caggatgct gcttaacatc ctacagtaca    38760
cagggcagcc cccaccacaa ggaattatca gctgaaattg tgaacagtgt ctacactaga   38820
cccttgctac tcatagtgtg gtccgtagac cagcagcatt ggcatcacct gggaccttgt   38880
tagaaatgct gttagacccc acccacatc cactaaagcc agctcttcat ttcaacaaac    38940
tccccgatga tgtgagtgca cattcaagtc tgagaagggc ttctttgagg tgagccttag   39000
```

```
tgcccatccc cctttggtgg ccccggatac caagggtgtg tgaaaggggt gggtagggaa    39060
tatgggtctc acctgccaat ctgcttataa taacacttgt ccacagggt gttgtaaccg     39120 agtgctgggg attccccaca gctccatcat gggctacaac ttcagcttgc tgggtctgct    39180
tggagagatc atctacattg tgctgctggt gcttgatacc gtcggagccg gcaatggcat    39240
gtgggtcact gggcttaccc cccatcccct taacactccc ctccaactca ggaagaaatg    39300
tgtgcagagt ccttagctgg ggcgtgtgca ctcggggcca ggtgctcagt aggcttcggt    39360
gaatatttgt tggctgattt attcagaaat tctgtccagc ccctaccttg gatggattta    39420
tcacctctcc aggccacctc ttctttccaa atagggccac ctaggtatag accaaagaca    39480
cgaaatcttt tgtgatccca caaacacaga gcaggtcaaa taggcccaag ccaattgaga    39540
ctgtggttca ggtcgtgatg cagagctttg ctgtggacgt gctcccactg cgtactagct    39600
gggcatgtgg cttaaccttt ctcagcctca gtcgcccat tgtaaatgga gataatgata    39660
ctatctcccc tcacaggact gttgggatgc tactggattt aataagctaa tgcagggaca    39720
tgctaagcac aacccatccc tgaggcccag agaggggtgg gccttggctg aggtctcact    39780
gcgaggtggg aatgtgggcc tccagaccag aggtaggtcc tgtggcccct agacagtgga    39840
cagcaatggt cagtttgaca caccagagcc ctagccatta cttcctggat gttgtgtgaa    39900
tattttctgg acatggctta tataaaatga aaagtgaat tgggcacgat acagggatag    39960
atttttagag atgaactggt agcatgatga taatcatatt cactgataac atttactact    40020
gttattgact gctttaaaag tgttgggcat tgtgctagaa accattatat gcattatctc    40080
cttgaattct cacaaccgcc tactgaggta ttctcagact ctaagaaatg agatttaaga    40140
gaagttatct gcccaaggtc actcggctgg aacctggctg taaaaatggc tgaagcaggt    40200
gatgaggagc tgatgcgttt ggacgtgtct cagagaaatc atggaggcgc tgcggttcct    40260
accggttctt ggatgccttc tacagagaca accatagccc caaattatag ggatcacata    40320
tcagtgggtg agacatcctt gcttgggatg aggaggggat gagctgtgtg aagcaaggcg    40380
cctctgtgat gggttccagt gatgtgtctg ccactgtctt aataactgtg caattctaag    40440
cagaaccttt cctgtctctg ggcctgagag ttccctctg aaagatgagg acttgaccta    40500
gcaaggtcct actcacatgc ctgtagagaa caggcagggg aagttagaaa aaaaaaaag    40560 ccagtgaagg aagggagctc ttcagcttgc acccatcatc acagtgcagg acccaggct    40620 cagtgttgcc agatccaatg acttctcaag agctcaaaat ctagagtttt gcatgtgctc    40680
tcccaagtac tggcagaaaa ttcaagattg ttagtaacac tgtgtggcta aattctgctt    40740
gtgggctgcc tagattccca attctgtgat tctgtggttc tctggaagca ttggttctcc    40800
acagcacctg catcacttgg aaacttgtta gaaatgcaag ccctacctac ggccccaccc    40860
cagacctacc cagttagaaa tctggggtg ggacctatca gtccatgttt gaacaagccc    40920
cacaagtgtt ctcttgcaag ctcaagtttt agaaccactg acctatagcc aaaaagaaa    40980 aagccaatca gtggttttct ggtaaaggat taacttaaca aactggcttt ccaagaaaat    41040
aaagccttga ttggtagcac ttgcaatttc tatggtacaa acgcttcccg catgactgag    41100
ttcaagctgt caaggagaca tcactataca tggacttggg aagagatgag aacaatcagc    41160
ccactgagcc tatgggaact ggctccagca catccctgca agtcaactct catcagggtg    41220
agtgagttga ggaccaagaa gcagttatcc tcttgccttt gcaggaccca gcaaaggga    41280 agggcatagt gacagtgatg atctctcttc cggaagtctt tggtttgctg agagtaaaag    41340
```

```
gcgtgggctt caccagtggt gaagccagtc atgcagcctt agtcctggta ctgaaactct    41400
ctaaatctca gttttctatc tgtaaaatgg gaaaataaga cctatgtcac agggttgctg    41460
tgcagattta gcaacagaac atagccccgt tctttatgat gactgatgct gcatccgtat    41520
gaggacatct ctatgtaatg gaaagatgga gagaggatta agcgcaaagt cacaacactt    41580
aatgggaact gtggattagc tacttggtgg cattgggcaa gtcagttgac tttgcattaa    41640
ttccacaaac aatatttccc aatttcctat tcagatgagc atatgtgatt gagtcagatg    41700
ctgtgatcag aaccaggatg gagcatttcc cacaaactgt gggattttta agtaatggga    41760
aggcacactg aaatggcact gaatcatgca gttgcagata ctcttttca attctcagtc    41820 ctttgattac gtcagggaga aagaaagtc cccacttggc ctgagaatct ctgcacccctt    41880 ctagctcttg ttaaccactc ttttgaatag cagagaaaac ctcagactgc catatctggg    41940
agagatttta gcaacatttt gttttcattg tatctctttt tacagctacc tcccatttcc    42000
cttctatttc aagctagtaa ctcagttttc ttttaaattc aattatttaa atgtaaaaat    42060
aagtctattt ggagaaaaaa aattttaata gcatctctgg aatgccagta tggctaaatt    42120
catgaatgtt gtcctcaaat gctgaaatct gggaagcatc tggccaagct ttgtggacag    42180
gcctgcctag tttgaatccc aagagccacc cagtccaagc cacaaaacat tggaattctt    42240
ggttcacttc cctaacctga acttgccctc tgtgaaatag ggacactaat agctcactca    42300
cagggctgct gtgaggacat gtgttgagct gagggtctcg ccaggggaga ccctgtgcag    42360
ggagactgtt atcatggtga tggatttctg cttcattcat ttcttttcc agacagcatc    42420 atatagaatg agttgtgggg tggcagtcag caggtttggg tttatcctct attctgccac    42480
ttattactta aaaaaacccc aaaaaaccca acttatatag tataagctat atccagaaaa    42540
gtgcaaatat catacaagta ccatttgatg aatcttctga tatccccaca taaccaacac    42600
ccagaacctc ttcttgtctc attccaggat aaccactaac ctgacttcta acagcatcag    42660
tcagttttgt ctgttttgt acattatata tgtgatggtt tgaatgtgtc ccccaaattt    42720
catgtgctgg aaacttaatc cttcaattca tatgttgatg gttttttggag aagggcctt    42780 tgggaagtaa ttaggattag ataaggtcat ggggtgaggt atgatggcac tggtgactta    42840
taagaagaga aagagaaatc tgagctggca tgctcttgcc ctctcactgt gtgatgactt    42900
ctccatgtca tgatgcagca agaaggccct caccagatgg tggcaccatg cttttggact    42960
tcccagcctc tagaactgtg agctaaatca atttattttc tttataatca cccagtttga    43020 tatttttgtca tagcaacaga atatggacaa agaaagaaaa ttaatgcaag aagtagagtt    43080
tttactgtaa cagattcctg aaaatgtgga agtggctttg gaactgggtg atgggaatag    43140
gttggaagag ttttgaggag caggctagaa aaagcctgta ttgtcaagaa tggagcatta    43200
tgccaggcac ggtgtctcag gcttataatc ccagcacttt gggaggccaa agcaggtgga    43260
tcacctgagg tcaggagttc gagaccagcc tagctaacat ggtgaaacgc tgtttctacc    43320
aaaaatacaa aaaattagct gggcgtggtg gcgcacacct gtaatctcag ctactcagga    43380
ggctgaagca ggagaatcac ttgaacccag gaggcagagg ttgcagtgag ctgagatcgt    43440
gctattgcac tccagcttgg gcaacaagag caaaactcca tctcaaaaaa aaaaaaaag    43500 aaagaaaaag aatggagcat taagacagt tctgcagttc tggtgagggc ttaaaggaag    43560
accccagaac tagggaaagt ctggaacttc ttaatggtta ctgaagtcgt tgagatcaga    43620
gtgctgatag aaatatggct ggtaaaggcc attctgatga ggtctcagat agaactgaag    43680
aaccacgtgt tggaaactgg agcaaaggtc atccttttta taaagaagca aagatcttag    43740
```

```
ctgaactttt tctgtgccag agtcatttat ggaaggcaga aaatctgtag gtcagccatg   43800
ttgtagggaa tgaaagaaca ttttcagctg agaacactga gagtgtgaca caactaccga   43860
ctgataagaa aactagtaca cataaattag ccaggcgtgg tggtgggcgc ctgtattccc   43920
agctacctgg gaggctgagg caggagaatg gcatgaaccc gggaggcaga gcttgcagtg   43980
agccaagatc gcgccactgc actccagcct gggcgacaga gcaaaactcc gtctcaaaaa   44040
gaaaaaaaaa aggaagaaag aaaattagta cacatagaac aaagccagag gctgttcatc   44100
aggacaaggg agaaaaactc caaagccatt tcagagatct tcaagactgc cctcccatt    44160 actggcccag agctctaaga gggcagaatg gtttggaatg accagctgct gcccagggct   44220
gccttgggtc tctgctcccc acatttctgg tgcagcattc ctcagccatc ccagctgtgg   44280
ttcaggtggc cacaggtgtg atgtggaagg taaaagtcat aaaccttggc agcatacaca   44340
tggcactaat tttgcaggtg tgcagaatgc aaaagctgag ggggcatgcc ttcttccacc   44400
tacatttcaa agggtgctgt gaacagccac cccagagagc ccctagtaga gcagggtcta   44460
gtggagctac aagggtgggg ccaccgccaa gaccccagaa tggtagagct atcatagtgc   44520
aatgccagct tgggagaact gcaggcatga gactccaacc tgtgcgaagt gcaacatggg   44580
cagaacccag caaaccaca ggggcagagc tccccgaagc ttcgggggtc caaattccat    44640
agtgtgtcca ggaggtggca cacagagtaa aagatcattc tgaaggttta aggtttaatg   44700
ttgttttcta tgttgggttt tgtactttcc tggaaccagt tacccttttt cccttgcctc   44760 ttttccttt tagaatggga atgtctgtcc tatgcctgtt ccactgttgt attttggaag    44820
tcataacttt gttttgactt tacaggctta cagccagagg gaatctccca tagaatgaat   44880
tgtaccttaa gtctcaccca catctgattt agatgagacc atggactttg gaattttgag   44940
ttggtgctgg aacaagttaa gactttgggg gttgtctaag tgtggtgttt catgcctgta   45000
atcccagtga tttgggaggt tgaggtggga ggattgcttg agcccaggag ctcaagacca   45060
gcctgggcaa catagtgaga cctgtctcta caaaaaataa aaataaaaaa attagccagg   45120
tattgtggca tatacctgta attctagcta ctcaggaggc tgaggtgaga ggatcacttg   45180
agcccaggag tttgaggctg cagtgagcta tggtcgtgcc actgcattcc agccagggca   45240
acagagtgag actctgtctc tacaaataaa attaaataaa cttagctgga tatggtggca   45300 cacatcgtgta gtcctagcta ctcaggaggc tgagacagga ggattacttg agccaaggag   45360
tttgaggctg cagtgagcta tgatcatgcc actgcattcc agcctggatg atagagcaaa   45420
atcccatctc taaaaaaaaa aaaaaaaaaa aaaaaaaaaa aaaaaacttt agtgctattg   45480
gaatgaattt tgcatgtaag aaggacatgc attttggggg ctgggcagg atgctgtggt    45540 ttgaatgcat ccctcaaatt tcatgtgttg gaaacttaat ctccaaattc atatgttgat   45600
gaaattggag gtgaagcctt tgggaggtaa ctaggattag ataaagtcat cagggtgggg   45660
cccctatgat gagactggtg gcttacaaga ggaaagagaga actgagctga catgctcttg   45720
ccctcttgcc atgtgatacc ctctgccatg taatggcagg cacagcaaga aggtcctcaa   45780
cagatgccag cagcatgttc ttggacttcc cagcctccag aaccatgagc tatatatact   45840
tattttacaa attacccatt ctgtggtatt ctgttatagc aatagaaaat gaactgagat   45900
aatatacatg gaatcataca gtaagtctgt gcttttgtat gcttctttta ctcaacattg   45960
tagttgtgag attcatccag gttgttaagc attgctgtac ccttttttcca ctgggatata  46020 gtgttctgtc atgcttgggt cttaatttat aaaggtgact gagtggcatt ttcttccagt   46080
```

```
attattggaa ggaaagtttt gttgttcaca gttccctgt aaacaagagg cagaacacgt   46140
catgcagggc cacacaaaac tgtatcatcc agggaccagg cagcagaaag agaggggaa    46200 ctgggactat gcctttatga aaagagtgg tgggagagta actgggtgag gcatccact    46260 aatgggcagg aagtgaaaac acatatgtta gaatttgtag ctgagggtt tataatatga   46320 gtttcctatg cctgagaaag ctgacttgca agaaaatgag ataaacaact ttggccatta  46380
gtgtggccct gtcataaatg aatgccagat aggcaaatag agaatctaag aaaagatagt  46440
tggaacaagt gttccattgt gtgaatgcag cagaatttat ttatccatta ttgaggagga  46500
tttgggtagt ttccagtttg gagctattat gaatattcta gtattgctcc tatgaacatt  46560
ctagcacttt tattttgga gcacacgaat gcacttctgt tgattatatg cctagaagtg   46620
aaattgttga attatacagt attcacacag tcagctttag tggctactgc taaacaattt  46680
tctctagtag tttgcgccaa tctaatcacc agtagtgtat agaagctcct tttactccac  46740 atttttgccaa cacttggtgt tttccttctt tttgattagt catttagcaa tcaaacctat 46800
tgtttacatt ttgatatctc caataactaa ctaaatggag cactttttaat atgcttttttg 46860 gacagttgaa tatctttcct tgtgaaatgt ctattcaagt tagtttgccc attttctatt 46920
gtggtgttct gtcttttttct tattgattttg taggaattcc ttacgtatcc tggatatgaa 46980
tcccactttg tgcgttacct ttttccttct ttctttcttt ttgaaacaga gtctccttct  47040
gtcacccagg ctggaatgca gtggcgctat ctcagcccac tacaacctct gcctcccagc   47100
ttcaagcaat tctcatactt catcctcctg agtagcttag attacaggcg catgccacca   47160
tgcccagcta acttctgtat agacaaaata attttggta gagacagggt tttgccatgt   47220
tggacaggct gatcttggac tcctggcctc aactttggcc caccttggcc tcccaaagtg   47280
ccaggattac aggtgtgagc caccatgccc agcccacctt ttactttctt aatggtgtct   47340
tttgaacaag agaggttctt aattttaata tagcccaatt tatcattgtt ccctttatgt   47400
ttagttcttt tatgtccttt ttaagaattt ttgcagccag cgcggtggct cacacctgta   47460
atcccagcac tttgggaggc tgaggctggc ggatcacaag gtcaagagat cgagatcatc   47520
ctggccaaca tggtgaagcc ctgtgcctac taaaaataca aaaaattagc tgggcgttgt  47580
ggctcttgcc tgtagtctca gctactcggg aggctgagat cacgccactg cactccagcc   47640
tggtgacaca gcaagactcc atctcaaaaa aaaattttttt ttgcaaggtc atgcatatgt  47700
ccccctgatt tttttcctaa aaatcactta ttattagatc aatgaattga gtaattgact  47760
acatttttca gtcattcaac aaatatttcc ctgaggtttt gataacctga actgtgtttg  47820
gagctgggga ggaagcaaac tattgaagat atacaaagat ggcaaagatg agggcctgga  47880
gcttgccaca cggaaggggg gatggctgcc tgaatggttg ggcaggtagt tgttgacatc  47940
tgcactccct acatgagcag cagggtggca actctttta tctttttaat ttattttttct  48000 tttctttctt tctttttttt tttttgagat ggagtctcgc tgtgttgccc aggctggagt  48060
gcagtggcgt gatctcagct cactgcaaac tccacctccc aggttcacgc cgttctcctg  48120
cctcagcctc ctgagtagct gggactacag gcgcctgcca ccactcccgg ctaatgtttt  48180
gtatttttag tagagaaggg gtttcactgt gttagccagg atggtctcca tctcctgacc  48240
tcatgatctg cccgcctcgg cctcccaaag tgtggggatt acaggtgtga gccaccacac  48300
ccggccttaa tttattttttc tagtctgcag gtaattctttt ttaattctct ccactctcct  48360
atgatcttat gaggtaggga ctgtcattat ttctcccact ttataatgaa caatcagtaa  48420
agacagggaa gataaccaaa tgacatacaa ggtggggtcc accccatgag gctgcaggct  48480
```

```
tggagctttg ctttgtctta aaaatgagaa catgagctgc ccacctgttg agacaagaaa    48540
caggaaaggc ttaaaaaact ggcttgttat gtacaactat ccgtgggct gcagtgaacg      48600 ggctggcagt gcccaggtgc aggctgaacc ctgggacaat cacattcagc atccaagggc    48660
ccccgtaata gcttaatgtt tgaattgaac ccctgggggtt gccttgaagg agagaggtcg   48720
tggaagtatg ttcaaggggt agggatgggc aggggagatg ggtctgaaag ccaagctcta    48780
ccccacccac cttgccccaa gagaaataga accttcatct ttaattgcct aacgagaaaa    48840
ctggggctgg ccagatgtgg tggctcatgt ctgtaatccc agcactttgg gaggccgagg    48900
cgggcagatc acttgaggtc aggagttcga gatcaccctg gtcaacatgg tgaaaccccg    48960
tctctattaa taatacaaaa attatccagg tatggtggcg catgcctgta gtcccagcta    49020
cttgaggcac aagaatcgct tgaacctggg ggacagaggt tgcagtgagc cgaccactgc    49080
actccagtct ggacgacaga gtgagactcc atctcacaaa caaaaacaga aaaaaaaaa     49140 aaaaaagag agagagagaa aactggaggc tctgagaggt tgaggacttt gcccagggtc     49200
ttgcagctag taagtgacag agctgggact tgagcttggg ttttctgact cctggtctgg   49260
ttcattatcc atgaggtgct gggaactaaa ataagccaca atcttggaat ctccgtcgcc   49320
tccctccctc ccacatgtct gcgtggcttt ttgggaaaat gccaggggaa tgtaccagcc   49380
agggagagga cccttgtttt cctcatggcc cttcctggca atggcactac tgacaccgac   49440
agtccttttt gtccctgatg acctctgctg cctgatgccc aagtgaccac ctctgctttg   49500
tcatttctag gattggcttc caggtcctcc tcagcattgg ggaactcagc ttggccatcg   49560
tgatagctct cacgtctggt ctcctgacag gtcagtgtga ggccaccttt cttccaccat   49620
tgccaggaca cagcacccac gtccagagcg caccctgccg tgtggctgga tgtctatgtg   49680
ccccatctcc ttccctgagg atcacataat ttcagaattg gaaaggttct tagaggtcac   49740
ctgctgctaa tgtggactgt gaggccaggg cagggaaggg acatccctga ggttataagt   49800
agggtgagtg gcaacgttgc agacttttga acccagggct ggtgatcaca ctcagttttg   49860
cacagaagcc cgagaaaatc cttcacccca aaagcctacc ttttatttct gaggacaccc   49920
ataatactat tttattcaac agatatttat tcaatatcca ctatgagcca ggcactgggg   49980
acacagcagt gagcaaaaca aattccctga ccccatggaa ttgaccttct agtgggggaa   50040
ggtattagca ataaatagac aaataagtgt ctactacgcc agatgggaag aagtggctgt   50100
gaagacagag caaactagag aaacatagag tcaatgtggg atgggtgtt cttttagggg    50160 ggtggtcagg gaaagcttat ctgagtagtt agcttttaag cagagacccc aatgaagagg   50220
agggagatat gcgatgcatt tagttagggg aagaacattc catgaaaata ggatagcaag   50280
tgcaaaggcc ctgagacagc agcatgcttt gtgtgttgag ggaacagtaa ggagaccagt   50340
gtggttggtg tgaatggagt gagaaggagc agcagggtt gagggcagaa tggtagtgag    50400
gagcaggccc ttataaaaga tgggaagcca ctggagatct ttcaacaaag ggaaaagta    50460 tgtttctgtt cttgcaataa aatagaacag caaaaaatct aggggagttg ctaattagcc   50520
agttttactt atatgccagg tgaaaatatg tggctaggtg cagtggctca tacctgtaat   50580
tgcagcagtt gggagaccg aagtgggcag atcatctgag atcaggattc aagaccagca     50640
tggccaacat ggtgaaaccc catctctact aaaaattaaa aaataagcca ggcgtggtgt   50700
tggatcccag ctactggga ggctgaggca gtagaattgc ttgaacccgg gaggcagagg     50760
ttgcagtgag ccgagactct gtctaaaaaa aaagaaaaaa agaaaatca cattcaggcc    50820
```

| | |
|---|---|
| aggtgcagtg gctcacgcct gtaatcccag cactttggga ggctgagaca ggtagatcac | 50880 |
| ttgaggtcag gagttcgaga ccagcctgac caacatggca aaaccctgtc tctaccagaa | 50940 |
| atacaaaaat tagccaggcg tggtggcgtg tgcctgtagt cccagctact ggggaggctg | 51000 |
| aagtagggga atggcttgac cccaggaggt ggaggttata gtgagtcgag gttgcaccac | 51060 |
| tgccctccag cctaggtgac agagtgagac tgtctcaaaa aaaaagaaa gaaaatatac | 51120 |
| attccatcca gaactgttca cctttattct acaagcaaac atcttttatt ggttagacac | 51180 |
| ccatatatgt gtccctaagc aggaggtgaa tgccaaataa gagacaaatg gcgtaagaca | 51240 |
| ctatgagttg tgtgacgttg ggcatgtcac tttactccct ctgagccttg gttagcttct | 51300 |
| ctgtaaaatg aaaggattat ggtaactaag ctggcttcct tccagctttta acaaactgta | 51360 |
| tggaggtact ttttggagtt acctgggtaa tttttgagtg tgagattggc tagaattgct | 51420 |
| ttaatatacc atgtctggcc ttagcttttt gcagagtctt tgtgaagaag cagaggcgga | 51480 |
| gtagcgttaa ttccgtaagt taacgttcag ttcgtggcag ctgcaatcc aaccctggga | 51540 |
| aaggctgccg gatttagcaa aaatgcaagg tgtctgtttt taaatttgaa atgaattggg | 51600 |
| tatcctgcat tttatttggc aaccctgtcc tgggactcac actattcact gttatcactg | 51660 |
| gtatgttcaa agtggtgctg acttgccctc tgtcttgcaa agtaccagga ggtcttttct | 51720 |
| tattcttcac tggagtcaaa aaagagaata gaggaaaaga caatcatatt gttcctttaa | 51780 |
| gagttaagac caacaagttt tcttcttac atgttgtttt tgacatgagc aaactggtga | 51840 |
| ttaaaaacaa cttgggtggc tcatacttgt aatcccagca ccttgggaag ctgaggtggg | 51900 |
| agaatagctt gaggccagga gttcaagcca gggcaacata gtgagacccc atctctacaa | 51960 |
| aagatacaaa aattagccag gcgtggtggt acacctgtag tcccagctgc tctggaggct | 52020 |
| gagatgggag gatcagttga gcttgggagg cagaagttgc agtgagctga gatcatgcca | 52080 |
| ctgcactcca gcctggacaa cagagcaaga ccctgtctca aaaaaggaaa caaaacaact | 52140 |
| tggacaatgg aaggggggaa aagttcctca agcagccaaa attgcaccaa atggactccc | 52200 |
| agaagacaag catttaattt gttaattgag ccctctatgg gcctgtctgt atttatttaa | 52260 |
| gaaacaatcc tatcaagcat agttattggg tttctcagcc caggtagatt agaaatagca | 52320 |
| gattagaggt gggctaggtt tctagaggta aagtacacca gcagaagtta aagtgaaag | 52380 |
| caaagagcct aacagaggaa gagaaattct tttttttttc ttttttttaga cgcagttttg | 52440 |
| ctcttgttgc ccaggctgga gtgcaatggc gctatctcgg ctcactacaa cctcagcctc | 52500 |
| ctgggttcaa gtgattctcc tgcctcagcc tcccgagtag ctgggattac aggcatgcac | 52560 |
| caccacaccc ggctaatttt gtatttttag tagagacagg gtttctccat gttggtcatg | 52620 |
| ctggtctcga actcctgacc tcaggtgatc cgcccacctt ggcctcccaa agtgctggga | 52680 |
| ttacagggat aagccactgc gaccggccga caaattctta aaactggaca caagaacaca | 52740 |
| aaacgcttgg gctgctgaga gattagaaca acaaccctcc acagctacac accttttcca | 52800 |
| cgttatatgg cacgttataa gtgggtgttc ctagtgatgg ttctgatttt ttttaaaaaa | 52860 |
| agtctaaata tgtttaatgt tgtctcagaa gacaaaatat attttagaca gatattcctc | 52920 |
| agtgatgagt aagcctcagc tatctggaaa attcatgcag gcgccagaga tcgttactga | 52980 |
| gtaattcaag ctaactgcgt catgctggtt gtaccctgca tgccaatatc agctaaaagc | 53040 |
| agcaccacga aagggaaata cgaatctcac taagcactcg cccattcttg ttaacgacac | 53100 |
| tggaactgat catccttaat aatacacaga taaatctatc aggagcattt ccttgcttcc | 53160 |
| tgtgaaagga agcactcatt ccatgtgtcc tgtgaaattc atccaacttc aggaagctgg | 53220 |

```
aggaatacat atggccaagc tatctgggca gagagtagac agggaatgga ggttgggcac   53280
agtggctcac acctgtaatc gcagccattt agaaggcaaa ggcgggcaga tcacttgagc   53340
tcaggtgttc aagaccagcc tgggcaacat ggctaagtcc tgtctctgca aaaaatacca   53400
aaaactgagc tggatatggt agcacacacc tgtggtccca gctacttggg aggctgaggt   53460
gggagggttg cttgaccccg ggagtttgag gctgcaatga gctgtgattg tgccactgca   53520
ctccagcctg gataacagaa tgagactctg tcccaaaaat aaaaaataaa atcaaagaca   53580
cttaaaaaga tggggaaaag gaaggacagg cacttaagca agttataagc tactttccta   53640
actacacaag tggaatctta agctgaggtt cccaggagtt gactggagcc agagaagaca   53700
gacctatagg agcacccaat tggagtcacc ctccatagta gcccatatgt cttacatgga   53760
tcagctttcg tggggcccett ttactccatc tggggaaggg cgtcagatct gtggctctca   53820
tgtactgctc agtacactgc cattcccagt tcttttttc aaaaaaaaaa aaaaaatgtc   53880
tacagaatcg gccaggtgtg gtggctcatg cctgtaatac tagcactttg gaaggctgag   53940
gtgggtggat cacctgaggt cgggagttcg agaccagcct ggccaacatg gtgaaactcc   54000
atctctacta aaaaaaaaaa aaaaaaaaaa attagctgga tgtggtggca ggcgcctata   54060
atctcagcta cttgggaggc tgaggcagga taatcgcttg aacctgggag gcagaggctg   54120
cagtgagccg agatcacgcc attgtactcc agcctgggcg atagagtgag actctgtctc   54180
aaaataaata aaataaaata aaataaaata aaataaaata ggctacagaa ttaagctggt   54240
ccaggaatga cagggcttcc atttatttgt cttcaattg tgggagaaaa aggatttctg   54300
ttgagatact gtcgttttga cacacaatat ttcgattaat cttgagatta aaaatcctgt   54360
gctccaaatc ttttaacatt aaattatgca tttaaacagg tttgctccta aatcttaaaa   54420
tatgaaaagc acctcatgag gctaaatatt ttgatgacca agttttctgg aagtaagat   54480 ttttcaccta ttaacgtgat agattttgag tgcatgaact taaaaacata cctgagtata   54540
tatgttgact tgctgtttat gagtaaaaca aaaacaaaaa tggagtaagg agcattgcag   54600
gaggaactag aggagaaaca aatccatgat atgcatgtgt gtggggagg gtggcgggga   54660 ggtggtaaag gtcaccattt ccctgatacc tcaaattcat tcagagtcag ggatgagaca   54720
gctttcactg gccacacttc ccctccccct atctgcagtc ctcagcgtag ccaaatagtc   54780
tgacatgcgg gtgacagaac cccacaatgc aaaagctgga agaaacctca agccttggag   54840
tccaacccct tttttgacag atgctaagag tggagacatg acttatcaag atcttacaac   54900
tggctgggca cggtggctca cgcctgtgat cccagcactt tgggaggctg aggtggggcg   54960
atcacctgag gccaggagtt cgagaccagc ctggccaacg tgtcgaaacc ccatctctac   55020
taaaaataca aaagttagct gggtgtggtg gcacatgcct gtaatcccag ttactcagga   55080
ggctgaggca ggagaatcac ttgaacctgg gaagcgaagt ttgcagtgat ctgagatcat   55140
gccactgcac tccagcctgg gtgacagagc gagactttgc ctcaaaaaca aaacaaaaca   55200
attgtacata tttaaagtgt tgtaaccaag tgagttacag agaaacacca cactttgagc   55260
ctaattcagg agtcctttat tagccggcga cctagagacg actagtgctc aaaattctct   55320
cggccccaaa gaaggggcta gattttcttt tataccttgg tttagaaagg ggagcgggaa   55380
ttgagctgaa gcaatcttac agaagtaaaa caggcaaaaa agttaaaaag acaaatggtt   55440
acaggaaaac aaacagttcc aggtgcagga gcttaaagc catcacaagg tgacaggtgc   55500
gggggctctg ggtgctatct gccggacaca aacgcagggg cactagagta ctatcacccg   55560
```

```
ggcaaattcc tgggaactgc ggacacagct tgccacagta ccttatcagc taattgcact   55620
ctttgatgtg ctgggagtca gcttgcacaa gttaagtcct tgaggaaggg ggtgggtaag   55680
gagcccttaa cgtcttgcaa atgaaggagc cgaatggaat ccctccggct ttcttagcta   55740
agagagagtc aatcaagtta atacaagtta gggtatcaca aaagtatata atttgataca   55800
ttttaacgta tttatacact gaagagacca tcaccaccat caagacaagg agcacaccca   55860
tcacttccac acacttcctc ctgctccttt gaaattcctc cctccctacc cacctggtcc   55920
cacccaaagg caaccactga actactttct gtcactaagg tttgcatttt ctgtaatttt   55980
tttgtttgag acagggtctc actccgccac ccacaccgta atgcagtggc accatcatgg   56040
ctcactgtag cctcaacctc cccaggctca ggagatcctc ccccctcagc ctcctgagta   56100
gctaggacca caggtgtagg ccaccatggc aggctaattt ttgtattttt ttgtagagat   56160
ggggtttcac cgtattacct aggctggtct cgaactcatg ggttcaagca atcctcctgc   56220
cttggcctct caaagtgctg ggattatagg catgagccac tgtgcccagc cctctgtaat   56280
gttacacaaa gggaatcatg cagcacgtac tgcccttggt ctggcttctt ttgctcagca   56340
tgattattct gagaatcatc cgtgttgttg cgtgtaactg acttcatcag cttctctctg   56400
cagctgtcag ctcttggctt ctcccaacag ccaatctctc tttatcccct gcaagtgttc   56460
ttgcctattt agcagaatca aggtactcta tcgaaaagac tcggaaaatt ggtttaatct   56520
attcattcat tcctcaggta tttatcgaat aactattcta taccaagtac tatgctaatc   56580
aaccaaggac agcacaaaca ggagaaatct ccagctcagt cacttgagtt gcaataaata   56640
tttgctggat aggtcaggtg cagtggctca cacttgtaat cccagcactt tggggattac   56700
tgagacggga ggatctcttg agcccaggag gccaaggctg cagagaacca tgatcatgcc   56760
actgcactcc agcctgggtg acagagtgag atcctgtctc tgaaaaaaaa tatttgctgg   56820
ataaattaag gaaatctgac gaacccatc agtagccatt gcagcaacag gtaaactaga   56880
acgagtgtga atttggaatg aggaaacccg atgttggcca tcattctgta atgtcatgta   56940
ttatgtaatg tattatatat taatgtatgt attatgtagg caagttcctt gacctctctc   57000
actggtaaca taagagtagt aatctttgtg ctacttcact gggttatttt aaagatcaag   57060
tgaggtaata atgtctgtaa caacattctg taaaatgcaa accgccacat gaatgtgaaa   57120
gtttattact agggatttag ccaaccacaa gggaatgtgt gagcataaga gctatcatat   57180
tgcaagccta cagtttctga ttttgtgcta ggtgcttttc cacattacct gattttatcc   57240
tcacaacagc cctgcataaa agtaagtatg tcgcccaggt gcggtggctc atgcctataa   57300
tcccagcact ttgggagccc gaggtgggca aatcacttga gatcaggagt ttgaaaccag   57360
cctggtcaac gtggtgcaac cctgtctcta ctaaaaatac aaaaaaaaat tagacaggcg   57420
tggtggtgga tgcctgtaat cccagctact tgggaagctg aggcaggaga atggcttgag   57480
cccgggagat ggagattgca gtgagatgag attgcgccac tgcactccag cctgggtgac   57540
agagcaaggc tatgtctcaa aagagaaaaa aaaagtaagt atctcagtct tgaagatgat   57600
gaaatggagg cctagagaga ttaagtaact tgcccaaaat gacagaacta atgcatagaa   57660
aagaagaaat gtgatgtctt ttggctccaa agacacccca catatgcgtt ggttacagtt   57720
actagagaaa agttattcca cccccacccc accccagaa atcttctgac ttgttttctc   57780
gcagttgagt aggaccattt attcggcagt gtaccattct cagcttgcag ttgaaagcca   57840
aatatccatt aaagaggcaa ggatgcaaac ttgctaagct gataaatcca ggggtgattt   57900
tttttttttt tgcaaaccat ccaacaagac attttaaata ctcattgaat ttcatagaac   57960
```

```
tgactgccag gattggaaag acattaaagc cagctcagcc actgcctcgc tggttggcca    58020
gaccacgcct ggcacttctg ggagggagca ctcaccaccc cccaagggca cccatctcat    58080
cctccgaagg tttatgaaaa tgcactcatc atttgctaat tcattccact acgtgtatta    58140
cctaatttgt gacacgatgt gaagtaccag agagataatt ctaaataaaa tatagttatg    58200
ggtctcaagg agccagatat gctaatctcc tatcctcctg cagtttacag tggtcctcac    58260
cagatactta tttacaaaaa ttcagtttat tatttatttt tttgagacag agtcttgctc    58320
tatagctcag gctagagtgt aatggtgtga tctcggctca cttcaacctc tgcctcccag    58380
gttcaagtga ttctcctgcc tcaacctccc aagtagctgg gactacaggc acctgccacc    58440
acggctaatt tttggagttt tagtagagac agggtttcac cacgttggcc aggctggcct    58500
cgaactcctg acctcaggtg atctgcccac atcagcctcc caaaatgttg ggattacagg    58560
cgtgagccac catgcccggc caaaacttca gtttataaca caatctttca cgtgtcttct    58620
gctttcatta aaagaataga cagttcccct ctttatttca gtttaataaa ccatggattt    58680
tatttcatgc tttgcaaaac acaagggctc actgacatgc acttcttaaa ctaattctgg    58740
ctggtcgcct gtaattccag cactttggga ggctgaggcc gacagatcac ttcaagtcag    58800
gagttcaaga ccagcctggc caatatggtg aaaccacgtc tctaccaaaa atataaaaaa    58860
ttagccaggt gtggtggtgc gtgactataa tcccagctac tcaggggcct gaggcagaaa    58920
aatcacttga acccgggagg cggaggttac agtgagctga gatcgcgcca ctgcactcca    58980
gcctgggcga cagagtgaga ctctgtctca aaaataaaat aaatacaaat aatgtaaaat    59040
acgaaacaag caatcctggc agtagctgct ggaatgagag gagggagagg tcatagggag    59100
gtcggggaca atggagcatg gagttgtgtt ggatttggct aagcagcagg aagtgcaagg    59160
cattccaagc aagaggaggg gggcaggtgg ggagcatctg caagaacaga agcagcatga    59220
gcaacctggc tcggcagtgt gtgaaaaggc tgaaaggtgg ctagagccac ttcaatttca    59280
tccttcaggc aaatgggaaa ttcccaaagg tttgagtggg gaagcaatgc ctacaatgaa    59340
agtttgagag tgaagcagag tgatcgaatt aagcatgtag gccgagttct gaaataactg    59400
caatgtgctg aagatcatcc attggcttct gaatgagtat ttgcagttta ttttttaaaa    59460 tgatttatt gccaagaaag ataaacacta ctgttttggt acaaaaacat aacaaaatgt    59520
gttgagtccc tcttgctgtt ttacgcgaag ttttaaaaat ctactcttgt cacagtggta    59580
tcacccctac ttctgatttc aaataaatgt tctagagaca cagtaagggc ccaacaaacg    59640
cttgttcaac aacacaagga gagccagctt ttaaagtagg aaaacaggcc gggcgccgtg    59700
gctcacacct gtaatcccaa cactttggga ggctgaggtg gcagatcac ttgaggtcag    59760 gagttcaaga acagcttggc caacatggtg aaaccctgtc tctactaaaa acacaaacat    59820
tagccaggcg tggtggtgca caccagtagt cccagctatt caggaggctg aggcaggaaa    59880
atggcttgaa ctgggaggc agtggttgca gtgagccgag atcgtgccac tgcactccag    59940
cctgggggac agaggagac tccatctcaa aataaaacaa aacaaaacca aatcatacaa    60000
aaacattagc tgggtgtggt ggtgcatacc tgtaatccca gctacttggg aagctgaggc    60060
agaattactt gaacccctgg ggggaggttg cagtgagctg agatcttgcc actacactcc    60120
agcctgggca acagagtgag gagactctgt ctcaaaaaat atatatatta aaaaaagaa    60180 aaaaaaagt aaactaggaa aacacatcag cagcctgcca acagactccc ctagcctcgg    60240
tgagggccag tgttctggga ggcagatctg aattctagtc ctagttcacc cactggcagg    60300
```

```
ctggtgccct tgggcaggtc gcttctctgg ggctcagttt cttcctctat aaaatgagat    60360
caaatcccat gttctaagag tttgtgctct ggagtcagac agatctgggt tctaccactg    60420
ccagctctgt gatcttgtag cttcagtctc gtcatctgac atggagataa cagtaactgt    60480
ctcactgtgt tgttagggtt taaaggagat aatgtatgtg aaatgttagc aaacaagtgt    60540
tagctaccct gatttccggt ttcagagttc tgtggtccca gtttatgcca catgcagtga    60600
cgttgtatgg taggctgtgg tgtggcacca cttcagaact cagcgcatgc acagcttgca    60660
gaagagaagg ccagaggaga cctaagaagg ctcttcgaac acttgaaaga ccggcatgta    60720
ggccgggcgc agtgactcac gcctgtaatc ccagcagttt tggaggtcga ggcgggtgga    60780
tcacctgagt ttgggagttt gataccagcc tgaccaacaa ggtgaaaccc cgtctctact    60840
aaaaaataca aacattagct gggcatggtg gcgggtgcct gtaatcccag ctactccggt    60900
ggttgaggca gaattgcttg aacccgggag gcagaggttg cagtgagctg agattgcatc    60960
actgcactcc agcctgagac aagagcgaaa ctccatctca aacaaaacaa acaaccaacc    61020
aaacaaaacc aaaaaaaaaa ctggcatgta gaagaaaaat acttttttctc tacacttctc    61080 caaagaattt aactaggccc aggggaggtg cagtataaat ttctaacaat ctcaactgtc    61140
tgccaaatgg aatgagctac ttcatatggc agtagtgagt cctctgtctt tggaggcatt    61200
caaataaaag ccagatggcc atttatcaac aatccatgta aaacgttaga tgaaataaaa    61260
cctatatatc caagatctct tccaattcag atttttatgaa agaatttcta aggtctttgt    61320
aatgagacat ttaggctgtt tcaagagatc aagccaaaat cagtatgtgg gttcatctgc    61380
aataaaaatg tttgttttgc ttttacagtt tcctcatttg gctgttggat tttaagcaaa    61440
agcatccaag aaaaacaagg cctgttcaaa acaagacaa cttcctctca ctgttgcctg    61500
catttgtacg tgagaaacgc tcatgacagc aaagtctcca atgttcgcgc aggcactgga    61560
gtcagagaaa atggagttga atcctttctc tgccactctt tgaggagaat ctcaccattt    61620
attatgcact gtagaataca acaataaaat acagccatgt accacataac aacatcttgg    61680
taaacaacag actgcatata tgatggtggt catccagtaa gctaaggtta atttattatt    61740
attccttgtt ttttttttt tttttttttt tttgagatgt agtcttactc tgtcacccag    61800
gctagagtgc aatggcacca tcttggctca ctgcaacctc tacctcctgg gttcaagcaa    61860
atctcctgcc tcagcctcca aagtagctgg gattacaggc acccaccaca tctggctaat    61920
tttttgtatt tttagtaaag atgggggtttc accatgttgg ccaggctgat ctcaaactcc    61980
tgacctcaag tgatctgccc gcctcggcct cccaaagtgc tggaaccaca ggcctgagcc    62040
actgtgccca gccttgtttg ctttttttaac agataacagt gtgctcatag aaactgctttt    62100 gacatgactg caatcatgtg cttcatagaa acttaattag attataccac tagagtcttc    62160 agattttttat acttttttttt tttgaaacgg agtctcactc tgtcaccagg ctggagtgca    62220
gtgccgcaat ctcggctcac tgcaacctcc gcctcccagg ttcaagcaat tctcctgcct    62280
cagcctcccg agtagctgga attacaagtg cgcactacca cacccagcta attttttgcat    62340 ttttacttga cagggtttca ccatgttggc taggatagtt tcaccaggat ctcttggcct    62400
catgatcagc ctgcctcggc ctcccaaagt gctgggatta caggtgtgag ccaccgtgcc    62460
cagcctatac ttcccttttt gaataccatt tggtgttttg aagaattaac agctttgtga    62520
acgtggcagt gcttgtgatt caggcttcca ttgagaccaa ggggagaacc tggttgcagg    62580
acaaacagac ggacagcgtg tggcagtgtt taaatgctct tctgaaggct gatacgacag    62640
ctctctgtgc actgattgca tatgcatccc aagattatat tattgttttc tactgctatg    62700
```

```
tgtcacactt tgccaaacag gatgtggaaa atgaataagc ggttttctta ggcacttctt    62760
aacagacaat tggtcaaaat gaactccatt gcttaagaaa cacataaaca ccatttagtc    62820
actgaacata gctatatgta tggttgttac tatgggaaat cttgttttgc caattttctt    62880
tgaaaattct ggcagaccaa ggttctttt gtttacataa tacttgaaaa ataaaaatga    62940
acaagctaac aaactaccaa gttttcactt acataaatgt agttgcatac agaaaatgtg    63000
actgtgaatt aattttcta ggactttaa actataagca ctatttgcac aaaagagaac    63060
caatctatca attacaaact cacataattt tacagatttt tttttccta cacagcacat    63120 aaaacagaag gaatttgaag ccaccctcca aacacagggg aaggaggctg tgtgtatatc    63180
ctcattgtct ttcacattct aaggtggttc cactcagtga ctgaaatcct taagcgttgt    63240
attagtctgc ttgggctacc ataacagcag cttaaactgt tgtttagcca ctcagactta    63300
aacaacagaa atttatttcc ttatagttct ggaggctgga agttcaaggt gccggcaagg    63360
ttggtttctg gtgagacctc tctccctgtc ttgcagatgg ctgcctcctc cctgtgtcct    63420
catagagcct gtcttctgct tttacacttc tggtgtcatc ttcctttttt tttttttttt    63480
tttttttttt ttgagacaga gtctcgctct atcgcccagg ctggagtgca gtggcccgat    63540
ggatctcggc tcactgcaac ctctgcctcc caggttcaag caattctcct gcctcagcct    63600
cccaagtagc tgggactaca ggtgcccacc atcatgcctg gctaattttt gtattttag    63660 tagagacagg gtttcaccat attggccagg ctggtctcga actcctgacc ttgtcatctg    63720
cctgcctcgg cctcccaaag tgctaggatt acaggcgtga gccaccgcac ccggcctctt    63780
cctcttctta taaggacacc agtcctatta gattagggct ccaccctcat aacctcattt    63840
gaccttaact attatttctt taaagcacct atttccaaat atagtcactt tagggggttag    63900 ggcttcaaaa gatgaatctg agggagctca attcagtaaa tagcagtagt cattaatgga    63960
caatgtatac aaagataatt tcgtgattac tgtccttatg cataaacgtc tcagtgttc    64020 cactgcgttt atccagattt agtatcacaa agactttgct ctgagaaaaa tgtgattttt    64080 ttttttttt tttttgaga cagagtcttg ctctgtcacc caggatggag tgcagtggtg    64140
caatctcggc tcactgaaac ctccgcctcc caggttcacg ccattctcct gcctcaatct    64200
cccgagtagc tgggactaca ggcgtccgcc aagatgccca gctaattttt tttttttttt    64260
ttttttttga cggagtct cgctctgtta cccaggctgg agtgcagtgg cgcgatctcg    64320
gctcactgca agctccgcct cccgggttca cgccattctc ctgcctcagc ctccggagta    64380
gctgggacta caggcgcccg ccactacgcc cggctaactt ttttgtattt ttagtagaga    64440
cggggtttca ccatgttagc caggatggtc tcaatctcct gacctcgtga tccacctgcc    64500
tcagcctccc aaagtgctgg gattacaggc atgagccacc gcgcccagca gatttttttt    64560
tttttttttg agatggagtc ttgctctgtt gcccaacctg gagtgcagtg ttatgatttt    64620
ggctcactgc aacctctacc atgttcaagc gattctccca cctctgcctc ccgtgtagct    64680
gggatcacag gcacacgcca ccacacctag ctactttttg tatttttagt agaaatgggg    64740
tttcaccatg ttggccagga tggtcccgaa ctcctgacct caagtgatcc tcctgcctcg    64800
gccttccaaa gtgctgggat tacaggtgtg agccactgtg cctggccaaa aatgtgattt    64860
cttatttccc acattgccaa ttccatttca attaactata atagctatgt ctattgagca    64920
ctcaagcgta ttctagaaac tgttcctgat tctggg                              64956
```

<210> SEQ ID NO 23

<211> LENGTH: 65624
<212> TYPE: DNA
<213> ORGANISM: Homo sapiens

<400> SEQUENCE: 23

```
acccttggcg tggacacatt tccagggagg gaccggagga cctcctacct cattggtcac      60
tgccagtgac tgagcttgac tcaggtagga gggcatggca ggtattctca gggagtctgg     120
tgtttacaga aaagtcatga ttacacgtga aagctgtggg ctccctggct tgattcacca     180
cacctgcagg aagcctggct gctcagacca gcacgccgtg gacatagcac cacttgctca     240
gcttcatttc cgtaactcag gctgccaggc ctgctgacaa attttcacgt ttgtaataac     300
cctgtgagga gaccagagta catcttactt gactcataag gaaattgaga ctgggtgatt     360
tagtaacttg ggaggcagaa ttgcaaagtg attagcaaca caagccatgg tgtcagatgg     420
atctgggtta ggtcccacct ctgccgttta ttagctgtgt ggctttgggt actcacgcca     480
cctctctgag cagcagtttc ctcttttgta agcgtaatga tgcctacact cacaggcttg     540
agaggaagat ccgatgaaat agcatatgca aaatgattgg ttccgtgctt ggcattccag     600
aaatggtagc tgttattcag ccaacaaata tttattgagc acctactatg gacttccctg     660
gtgctgagga tacaacagca accacagcag tcaaaagtcc ctgtctttat gttgctcaga     720
ttctcatagg ggaaagcaga taatgaacaa atacacggcc agacgcagtg gctcacgcct     780
gtaatcccag tactttgcga ggccaaggtg ggcaagtcac ctgaggtcag gagttcgaga     840
ccagcctagc caacatggtg aaaccctgtc actactaaaa atacaaaaat tagcgcagtg     900
tggtggctca tgcctgtagt cccagctact gggaggctg aggaaggaga atcgcttgaa     960
cctaaaaggc agaagttgca atgagccaag atcgtgccac tgcattccag cctgggtgac    1020
agagtactcc atctaaaaaa aaaacctaaa tacacaagta aaaatataga cttcgtcaga    1080
tgctagtaag tgctgtgaag gaaactaaaa ggggaacaca aggaaccctt gtcaagggga    1140
gcagaaaggg gagttgatgc tgtccttta aatagggcaa tcagaggcca ggcacagtgg    1200
ctcacactta taatcccagc actttgggag ttcgaggcag gtggatcact tgaggtcagg    1260
agttcaagac cagccaggcc aatgtggtga accctgtct ctactaaaac tacaaaaact    1320
agccaggtgt ggtatcgcgt gcctataatc ccagctactc gggaggctga ggcgggagaa    1380
tcgcttgaac ctgggaggcg gaggttgcag tgagccgaga ttgtgccatt gcagtccagc    1440
ctgggcaaca agagcaaaac ttcatctaaa aaaaaacac agcaaaaaag gcagtcagg     1500
gaaaacttcc ctgagaaggg gatggtggag tacagatcca ggggaggtgag gtggggagca    1560
agccagtaca gttgttcctt gactttcgat gaggttatgt cctgataaag ccatggtaag    1620
taggaaatat tgtaagtcaa aaatgcattt aatacaccta acctacgaaa catcatagct    1680
tagtgtcacc taccttaaac atgcttagaa cgcttacatt agcctacggt tgggcaaaat    1740
catctaacac aaaagcctat ttatgataaa gtattgaata tctcatgtaa tgtactgagt    1800
actgtacgga aagtgaaaga cggagtggtg ggatgggaac tctaagcacg gcttccactg    1860
catgtgtgtt gctttcgcgc catcataaag ttgaaaagcg ttaagtcaaa ccaccgtacg    1920
tcggaggcca tctgtatctg gtaggaggag tgtttcagac agagaaaca gcaggtgcaa    1980
tagagtgctt tttcccagc attttattat gaaaaatttc aaacatctac caaaaaagt     2040
tgaaagactt gtacggtgaa aagccataca tctcacagct agaatcaaca attaacatt     2100
tactgtattt ggttttgac ttatctatcc tagatccctt gtgctttctg tagcaggtga    2160
cctgccttga agatttaaag acagaatatc gggaaatgta gtcagaaaat ggggcctttt    2220
```

```
ataagagtca gaggggaaga gcaaaaactc tgctttcgag aaatctgtcg ggagaggcca    2280
actgcaggga tacctcccct ttttaatgaa agcattctg ttctgcgagg agcgggatcc     2340
tcttgtcaag cagtcagtcc ctgctgcttc cttactgggg caggatcagg acgcacaggg    2400
atttggagtg ccttggaacc aaccaccacc cacgctgttt gccagctggt aaacatgcct    2460
gtcaggtcta ggggttggca ttgcctggaa atctttagtg ttcatcttgc tgacatctgg    2520
tgccctcggg taggtaggtg cagttggctg cctggtttac agagcttgta ctgggcccag    2580
gttagcaggg gtcacatccc tttatcccac tgtgcagggg agttccttct caggaaaccc    2640
agtttataag aagtactgac tgccagaaat agagcagaga tcagaaccag gaggcaattg    2700
tgagaggaat ggagacttct gacctctggg gattggggta ccctcccct taattgctgt     2760 tggggtagca gagggcttag aagcccatgt tcctagactt ttagaattgg aagaagactt    2820
agaagtaatc taggctgggg gtccccaacc cccaggctgt ggcccgttag aacctgacc    2880 gcacagcatg aggggtaggc cagcgagcac taccgcctga gctccgcctc ctgtcagatc    2940
agcagcggca ttagattctc acaggggcac aaaccctatt gggaaccgcg catgagaggg    3000
atctaggttg cgtgctcctt aggagaatct aactaatgcc tgatgatctg aggtggaaca    3060
gtttcatccc cacaccatcc ctccaacctc accccggtcc atggaaaaat tgtcttctac    3120
aaaacccgtc cctggtgcca aataggttgg ggaccctga tctaggctac agttaagtgg     3180
tcaaacaccc aggtcctgaa gttaggctgc ctgggtttaa atcccagctc tactgcttac    3240
tagccctgtg accttgagca agtcacttag ttttctgtg cctcagttta ctcatttgta     3300
ataaaagctt aatagtaccc atcccagtgt catgaactaa gttcatatat gtaaagtgct    3360
tagaatggtg cctagcaagt acttagtaac agttagctct gaaatgtat aaagcaaaat     3420 taaccaatgt tttagtggtt tgcagccaac ttttttctat gcgtgtgcta acatattatt    3480
ttataagagt gggaatatat tgtacatgct gttatataac ttgctttttc actaaacagt    3540
ctatcctctg tgtcagtttt gataaaagcg ttttcctctt gcttttcctg catatgttca    3600
gaaccatcat attggtagca gtttcatgt cctgcagttt tcttaaccaa cccctgcta     3660 gcggacattt aggttagtct cagttttttc cttctgtaaa taaagctgca ctgagcaaga    3720
agtgaccgat gccaagtgac tagatgacct taggtatgac ctctctgggt cttggtttct    3780
tggtctaaaa acaaaatgac aggattcgac tgggtgatta aaatctcctc tgatctacat    3840
aggaattgtt ttcaagacat ttctgcattc ctctagtgac agggtgctca ctacctcatg    3900
agtatttcag tggacaactg taatggtcaa taaagtatcc actttccacc ttccacttcc    3960
ctgtagctcc tggccctggc tttattctct ggggctccac acattcagtt tacactcagt    4020
ggccagtggc tggggccatt gtagaaaatg aggaaactcc aattccttcc ttcttttctt    4080
cctctttcat cccttcctcc ctccctacat ccctctctct cttccttcct tccttgacac    4140
ttaccatgta ccagaccttc tgccaggcac atggatggga gcacagttcc gggaagttgg    4200
ctgcagggtt agaactaagt cccaagcccc gtaaagctca tgccagggga ctggactgtc    4260
cagtactgag ggatgggat gctgaggctg gtggccttcc tcagatgcac tgtagtgccc     4320
caggcagagt cctgggctgc cctgtgagga ggtgaccaga ggtagagcaa cttcacccta    4380
aggctggatc aggatcccct ccaggttttt actagagcca aacccacatc tcctttctct    4440
tctgccaccc cccttaaaa tgcttagaaa cacatagatt taaatacaag ttcaaatgta     4500
agtaatttca actgtgtaac tatgaggagt caattctacg tgggtcctat ctgtatcctc    4560
```

```
cccagggctc agctccattc tttgctttca ttcattctca ttcaatacat tgttgttaag    4620
agctcactgg gtgccctctc tgtcatgtag taaggtttta aaaagaaagc ctcttctgag    4680
cttcagtttc cttatttata aaataggagt attgatccgt tccttgcttt tcttacaagg    4740
atatgctgaa gatgactgaa gtacagagta aagaaggatt atgtttgggt gtcaaaggaa    4800
tagaatgccc tctttcaaac tgagcacagc aggaacctgt aacaggaaca cagcaacttg    4860
ttgaatgaat gacaatattg gaaaacatac atttcctccc ctccccatca tagtccctct    4920
gcttccgtgt taactccata gacaggccag cacagccagc cttgcagcct gagataaggc    4980
ctttggcggg tgtctcccct atcgctccct caagccctca gtaggtgtt ggagagaggg     5040
gtgatgcctg gtgctggtgg aaccctgca cagagacgga cacaggatga gctctaagta     5100
cccgcggtct gtccggcgct gcctgcccct ctgggccta acactggaag cagctctcat     5160
tctcctcttc tattttttta cccactatga cgcttcctta gaggatcaaa aggggctcgt    5220
ggcatcctat caaggtgaga gttcattgga acagtggtca caggagcaaa tagcaggggc    5280
aggggcgggg gaggcctatg gttctccagg ggcacagatg ttcctttcta caaaatcccg    5340
aggaaaagat tcccccatct tcttccgtag attgcaccga aattcagtca acaatgtaag    5400
cttttccttta gaagcagcct gggcatgccc tcttctgtga agcctgcctt gattttcag    5460
cacagtgaga ggcatcctct ttggtgttcc tcaaattccc tctaccaaat ggtcttcata    5520
attctctgct tctctgcttc cccttctctc tccttagtgg caaggatttt ttttattttt    5580
atagatttag gggatacaag tgcagctagc ttatgcaagc aatttcatgt tgttgggttt    5640
tcgggttttg tttcctttt gtggcctctc gctcatttct tatttctttt tgagacaggg    5700
tctcactctg ttgcccaggc tgaagtgcag tggcatgatc atggttcact gcagccttga    5760
cctcctagtc tcaagcaatc ttcccacctc agcctcccaa gaagctggga ccacaggagg    5820
gcaccaccat gcctggctaa attttttttt tttttggta gagatgtggg tctccctgtg    5880
tttcccagac tggtctcaaa ctcctggaca caagcgatcc tccagcctca gtctcccaaa    5940
gtgctggaat tacaggcgtg aagcactgtg cccagctctc ttgctcatat ctatactagt    6000
tttcttttgg aagcttcagc ctgttgctac ccccaccccc acccccacc gaccccagct     6060
ttcttctcac ttagggggctg ggaagtctgc atgctgtcta taaatccaga accagaaggt   6120
atggctgaag ggagggtag gatgatggtt atttatatt cagctaaaaa tattcccaga     6180
ctgtgatgag acaactgtaa ataagacaga tgtccacaat ggtgtgactt tgcttttta    6240
aaaatattga aatgagtttc aggcatctca gtgggctgat aggttgttga taatggacag    6300
ggcctccttg aagaatgtcc ctgagacaaa gttgaagctt gagcctggtt gagtgcttgc    6360
ttgttcctag gttgatatga acggctagtt aactggaagc aaagagaagt catcctgggg   6420
gccatggcag tgacaagtag gacttaggga gggaagccct tataccattt aaggtgctgg    6480
cccagagagg agccttcagt gacagacaaa caagagctgg cacaatttta attcatttca    6540
atttactttta attcatttca atccaataca attcaatgca ttccattcat tcaaccatgt   6600
atgacatcca atgtgggatc cagacacatg atgattagaa ctgatattta tgagcactta    6660
ctatgtacca ggcactattc tacatgcttt acattgaacc ctcacaataa cccaatgagg    6720
tgggtactat tatgatcttc gttttcata tgaggaaact aggcatatgg atgttgagta    6780
atttgcccaa ggtcgctcag ctagcaatag cacagcgtat ttaaatttag ccaccctgga    6840
tttagtttcc ttcacttaa ccattatgca tcatggcccc attttacagt ggcgttgagt     6900
catttgtcat ataacccagt aggtgtagca gccactattc caaccctgta gattgactct    6960
```

```
agggtccatg ttctttaccc ctgcaccgtg ctactaacgt aggtacaaaa tgtcctcaga    7020
aactcacttt atatggaagc tcagaggagg gtccacaacc caggcagggg agacgatggt    7080 gtcagggag  gcttctggag ggaggtgcct gcccagccag ctcttgaagg ctcagtagga    7140
attacctgtg ggacaaaggc gggtcatcca agtgagggca cagtgggtgc cattgcgtgt    7200
gcacacacta gagcagactg agcttgggct taacattgca ttgccctgta gcctaaaaag    7260
agaagcaagg ggctgggcga ggtagctgac acctgtaatc ccagcacttt gggaggccaa    7320
ggctggagaa tcacctgagg ttaggagttc aagaccagcc tggccaacat ggcaaaaccc    7380
catctctact aaaattataa aaactagccg ggtgtggtgg cacacgtctg taatcccagc    7440
tacttgggag gccattacac tccagcctgg gcgacagagc aagacttcat ctcaaaaaac    7500
caaacaaaaa caacaacaac aacaaaaaac aagaggaga  gcagggactg ggtgtggtgg    7560
ctcatgcctg taatcccaaa cactttggga ggccaaggcg ggcagatcac ctgaggtcag    7620
gagttcgaga ccagcctggc ccatatggtg aaaccctgtc tctactaaaa atacaaaaat    7680
tagccggatg tggtggcacg tgcctgtagt cccagctgct gggaagctg  agggaggaga    7740 attgcttgaa cccaggaggt agaggtagct gagctgagaa tacgccactg cactccagcc    7800
tgggtgacag agtgggactc tgtctgaaaa aaataatagt aataaataaa ataaacagg     7860 gaagcagtgg gtggtagact cactgggctg catacggagt ttggcttcag tctgaggtcc    7920
gaatagtaaa caggagcgcg acaagtttgg gtttgggtca tggcggatgc catgccaggg    7980
ctggtgttgg gcacagggga aggggcatgg cttgagacac aagaccagcg tggaggctgt    8040
agtgtagtat tgacccgagg gcttcaacct tctgatggtg tacacaccat tttttgagca    8100
tgtaccatgg ttatatgtta cactttaagt attactacat taatatattt tgtatgttat    8160
aataaataca tacaaattag gaaaattgaa agagatcaga atgaaatata taatattttc    8220
aaattactaa tcataatggt gtcaatctcc aggcagggtc cattgctaca gttgacgata    8280
gtggatgaaa attcactcct cagagtcttc ttgataattt gaaattgtct tgattgactt    8340
gtcagatctg attagatcga catttttaa  atctcgaatg tgactgacag cttgtacaag    8400
gagaagtttc actctgcctt tccttttgt  tcacttgact gccattattt ctctgcttcc    8460
aatctgtgtt tttctgcacg agttggttaa gccattactt cattttgtga agtttgttg     8520 agttaaactt aggtaactta atctgtcaat ccacttaatt gaattcagtc ctggtaaact    8580
ataatagatt attcaaacct gccaattcta aaagacatt  ttgagacaat caggaaatct    8640
gaatatagca tgaatatctt acgatataca aggattatt  ttaattttgt taggtatgat    8700
aaaagcatgg tgggtttttt ttttgttttt gtttttaag  gctctatctg ttagagaggc    8760
acattgaaat ggcatgatat ctgggtttg  ctttcatacc agaaaaaga  aaagtagag     8820 aaggattata gaaacaagat tggtctcatg tgacaatcat cagagtttgg agatgggcac    8880
gtagggtcat cgtgctgttc tctctgtttt catatatgct ttgaaagttc tgtaatagtt    8940
aattaaaaaa aaaaaaaaca ccctggctga gcacttaggg aggccaagtg gggaggattg    9000
cttaaaccaa gaagttcaag accagcctag gaaacatagg gagacccccc ccgccatct     9060 ctaaaaaaaa aaaaaaaaa  ctgtaaaatt taacccagtg tggtggcaca tgcctgtagt    9120
cccagctact cagtaggctg aggtgagagg cttgcttgag cctgggagct tgaggctgca    9180
gtgggacggg attgtaccac ttcactccag catgggcgac agagcaagac cctgtctcaa    9240
aaaaaaatga aaatatttga ggtgaagcga gactgtaata acaaatttaa aaatataaat    9300
```

-continued

```
aaaacataaa ggctgggtgc ggtggctcac gcctgtaatc ccagcacttt gggaggccaa      9360
ggcaggcaga tcacgaggtc tggagatgga gaccatcctg gctaacatga tgaaacccca      9420
tctctactaa aaatacaaaa aattagctgg gtatggtggc gggtgcctgt agtcccagct      9480
acttgggagg ctgaggcagg agaatggcgt gaacccagga ggcggagctt tcagtgagct      9540
gagattacac cactgcactc cagcctgggc aacagggcga gactccatct caaaaaaaaa      9600
atgaaaataa aaataaataa aacataaaac cctgccatta gttgcaacat gaagaatata      9660
gagaaatgcg tatcaaatcc ttctcattgg accaatattc ccttagggca ccttccaaag      9720
ctaggagact caaggctgta tgacatcctg agcaagtgag gggtggcttc tgggtgaatc      9780
tgaatattaa atatttgcag aattgaaaac ttcacaaagt acctttagag atagaatagc      9840
ctagatccat gtttctcaaa gtgtggtccc cagacctgct gcctcagcat ctcctggaaa      9900
tttagtagaa atgcagattc tcaggcccta ggccagacct actgatcaga agctctgggc      9960
ctggggccca gcaatctgtg ttttcacaag ccctctgggt gattcttctg tgcgtgaaag     10020
ttcgagaatt cctggagcta gactgattca aatcttgcct ctgtatctta gagaccttgg     10080
gcagattagt caacctcttt ctgcctctgt ttctacttct gtcagaggat gatagtactt     10140
gtttcattaa gttgttgaaa ggataaatga attgacacac ataaagagta ttagctttta     10200
ttatcaaaag cttttttttt ttgagacaga gttttgctct tattgcccag gggagtgcag     10260
tggtgcgatc ttggctcacc gcaacctccg cctcccaggt tcaagtaatt ctcctgcctc     10320
agcctcccga gtagctggga ttacaggcat gcgccaccac gcccggctaa ttttgtattt     10380
ttagtagaga cggggtttct ccatgttggt caggctggtc tcgaactccc aacctcaggt     10440
gatccacccg cctcggcctc ccaaagtgct gggattacag gcgtgagcca ccatgcctgg     10500
cccaaaagct ttaatttctt aattttttaa ataaataaa taaaactaga attgcttgtt     10560
ttcttccagc taccctggtg attgtattga gcattttctg gggtgtgtgt tctttgctgt     10620
aatgactact ggtctggatg acctgtgatg agaccagatg ggcaggggca gtggaggaga     10680
ttctagagat atttaggaga taaagtcagc tgtacttgat gaaaagagtg gggagttaag     10740
actggctgca gatgtatgat ttggcataga gaggtgccag ttcctgaggt gagagacaga     10800
aggggaggga caggttgtga ggatgaatga acaatgatat gttcattctg ggcttggagt     10860
taagggcct atgatatgct taggggaagc agagagtatc aattacctat tgctgcataa     10920
cagccacccc aaacttagtg gcttaaaata gcaacctttt aatttactca tgatcatgat     10980
tctgtggtgc aacaactggg ctgggttcag ctgggcagtt cttctgttag tttcacccag     11040
ggtcattcat gcatctgcag tttggggtgg gatggcctca gatgacctca ttcacatgtt     11100
tggcaattgg tgattcactg ggggccatta ctgtaacaat cgcctaccag gcagagcttc     11160
cctaaggcta ccaaactggg agactatcct gggtcctgtg ctgtggatac cactcagtcc     11220
cccatcccca ccccatactc ctcaaaggca gagagagggg ctactagaag acagaggagt     11280
tttcccagtg acatgtaaac actccaaacc ctggcacctt ccacactgca gctttggtct     11340
gcccctttgg gaaatctctg ttttcttcc caggctgctg gaggggtgag agtcgccggt      11400
agagtagagg ctgtgggcga ggaggtggcg gcctcctgag gctgcagtgg tctttccagg     11460
cagcagtggg agcacagggt ggaggtcaac cctagagcct gggggagtga agctggttct     11520
gccttcagag ctcttggtgc tgaagttcc t gcaggccaga gggaggggca agagtgggag     11580
ggggtgcaga tccagaatca cagaggcagc tgaccggagg aggcagctgc caagggggat     11640
ggactcagaa ggccaaagtg ctgttatcca aacgaactct ttgcaagtgg tctctttgca     11700
```

```
acaggcctgg gggagagcag tcttgcctaa agtcacaccg ctaatcagcg gccggcacgg   11760
ggtaacagtt actaacactc actacgtacc caatgctggg caaagtgact tgcatgagcc   11820
agcgagctca atgctcatgg caatcctctg agcagctggc attgtttcat ctcaatttta   11880
cagctcagga agctgggaca cagaggaaga gccaggctct gaacactgac aacctgattg   11940
agagacccac actgttcatc accgttacgc tatatatgct gtatagaaag gcaggatggc   12000
ataatggtta aacctaggta ggtagggttt gaatcctcct gctaccattt actagctctg   12060
tgacttggac tagttatagc acctctctgt gcctcccttt ccccctctct aaaatgggga   12120
taataaatcg tacctcctac ctgaggctgt tgtgggctaa gtctgtaagg cacgtagaac   12180
agtgcctgga acgtgsggta ctgtctatct gtgtgcctgc tgttacaaca atggtgagta   12240
ttgccttatc tctcgctgct gaactaccag gttagacttc tttctgcaag tcatgaggct   12300
ttcataaact tttcctgaag gctttccgta gaatgtacaa ttccctctg ggcccaggca   12360 tgggcgcccg ggtaggacat ccacttctta tcacccctga acaccttaga gcccatcagc   12420
ttatcaaacc agcagctgat gtgagtgcag agcagactgt gagaggtgga ggctgatacc   12480
agtgaggatg ctccaagctg ggacccagcc ctgaagcggg agcccagata atggacgggt   12540
ggaaatgggc ctggagccca agagaggtgg gaggatgagg gggcagggg aggagaagcc   12600 tgaaatcaaa tgttatttcc tgaccagttt ggggtgcatg agctctgtca acagctcatg   12660
gaaactgctg ccctaatttc atcttgttgg ctgaggcaca attcctctct cagggacagt   12720
gtagagcctt ggggaggaag gccctgagcg catatacctg gaatcaggga atcgggatca   12780
ggggcagcag ctgtgcccga taaagccccc acccaggatc ctctgacttc ctcatctctc   12840
tttttttttg agccggagtc tcactctgtc atccaggctg gagtacagtg gtgcgatctc   12900
ggctcactgc aacctcagcc ttctgggttc aagcgattct cctgcctcag cctcctgagt   12960
agctgggatt acaggcatgc gccaccatgc caggctaatt ttgtattttt agtagagacg   13020
ggatttcacc atgttggcca ggctggtctc aaactcctga cttcaagtga tctgcccacc   13080
tcagcctccc aaagtgctag gattacaggc ataagccact gtgcccggcc tttttttttt   13140
tttttttttt tttttttaaa aaagggtct ccctctgtcg cctaggctgc tggagtatag   13200
tgatgtgatc gtggctcact gcagccttaa ccttctaggc acaagccatc ctcccacctc   13260
accctcctga gtagctggga ctacaggcac ttgccaccac gcccaagtaa ttttgtattt   13320
tttgtagaga caaggtcttg ctatgttgcc taggctggtc ttgaactcct cagctcaagc   13380
aatcctcctt ccttggcctc ccaaagtgct gggattacag gtgtgagcca ccacacctgg   13440
tctgacttcc taatctttag ggccccaact ctgcccttat ccaggcaact ctcctctccc   13500
catcttccac taacttcttt ggaatattcc agagctgtaa aagccttaga gagtatcaag   13560
tccaactcct atgtgttaca gacagggaaa ctgaggccta agagggtaa tggacttgcc   13620 taagatcgct tagtgaggtg agagaagaaa gagctagaga cagcctagcc tgtgcaagga   13680
catagttcca ggcattcaga gctgcgctct gctgccggca tgtttggggc ctggtagtta   13740
gttcactgct gaactaccag gttagatttt cttctccaa gttgtggggc tttcataaac   13800
ttttcctgaa ggtcttcctt acaatgtaca attctcctct gggcccggtc atgagcgccc   13860
ctcacaggct ctctctggtc cccttctgta aaatgagagg aaaatggaag aattgctcta   13920
ctcatggaat cttcaataag tctggaccct atgcatatag cattgctaca aaatggcaga   13980
tgcactttaa caatcgtgtt taataaaagg ttggatttgc atatctgaag tggggcatgc   14040
```

```
agtctccaac tgaacacaag cctcactgct cccacatgtg cactgcacct tcatatacat    14100
atttcctgct tggctcctga gggaatttga gtaatcccaa gaggaacccc tgtagaaaat    14160
gtcccctggt cacacacccc cattcctaag gatgcaagca ggagatagaa acattccctg    14220
cacctccctc cttgctgtca gaagaagtgc aaagagttga atccttccta atgcccactt    14280
ctcacccacg ccccaaatcc ccaggtcccg tggaggtcct tgggggtctc ctatatcctg    14340
gtggtgtcag gttgatttgg aaatgtcagt gtcctccctt gtcctctctg gcagaccctg    14400
ggtgtgtgta cgtttcaatg gaagtgaatt taaatgtact ttataaatca aagacttttt    14460
ctgagacttt ggagagttcc agtaatgaga gcttctcatt gttatcaaag ccagggctgg    14520
agaccagtgg caggtgagtt cctattgctg tgattgtcat gatgatgttg atgaacagcc    14580
actatttatt gagtgttctc catgtgctag gcactgtact aaacattatt tccttcggat    14640
gtcccagaaa cctctcaggt ggctctaatt acccttattc tgttgataag gaaagtaagc    14700
aacttagaag accacagggc tatgaagttg aaacacgtaa attgatattt tattttattt    14760
atttatttat ttatttattt tgagacagag tctcactgtg tcgcccaggc tggagtgcag    14820
tggtgcggtc tcagctcact gcaacctccg cctcctgggt tcaagcgatt ctcctgcctc    14880
agcctcccga gtagctggga ttacaggtgc ccgccaccac atccagctaa tttttttgta    14940
attttagtag agacggggtt tcaccatgtt ggccaggcta gtctcgaact gctgacctca    15000
tgatctgccc acctcatcct cctaaattgg tattttata tgtccaaaag agtcaactgg    15060
tggcaattta gtgaggttta atctaatagg aaatgataga gctgggatcg aacagagcta    15120
tgtgaactca aaacctatgc ttcccctttcc accttttcga aaaacattgt ctaggctggg    15180
cacggtggct catgcctgta atcccagcac tttgggagac ggaggtgggt ggattacatg    15240
aggtcaggag ttcgagacca gcttggccaa aaattagcca ggcgtggtgg tgcgcgcctg    15300
tggttcccac tgaagcacag gaggctgaag cacaagaatc acttgaaccc gggaggcaga    15360
ggttgcagca accgagatcg caccactgc actccaacct gggtaacaga gagactctgt    15420
ctcgaaaaaa aaaaaattgt ctacatgctg gttgcagaaa atttaaacac taaaactaaa    15480
aaagtaaaac atctcccaaa gttagagaca atattcatga tgggaaaaaa aaaattcttc    15540
aagatttctc tctctccagt catttattca tgtgcgaaaa cagttggtga ttattgataa    15600
gaagagggag ggcagatggt gtggtagtcc aaggcacagg ctccagcaga ttatctaggt    15660
ttaaatcttg gctgtaggcc aggccctgtg gctcatgtct gtaatcccat cactttggga    15720
aaccgaggtg ggcagatcac ttgaggtcag gagtttgaga ccagcttggc caacatagtg    15780 aaacccccttc tctattaaaa atacaaaaat tagccgggca cggtggtggg gacctgtaat    15840
cccagctact tgggaggctg atgcaggaga atcacttgaa cccaggaggc agaggttgca    15900
gtgagccaag atctcgccac tgtactccag cctgggtgac aagagtgaaa ctctatctca    15960
aaattaaaaa aaaaaatct tagctctacc caccggggca agttacataa cgcctctgtg    16020
ccttggtttt catatctgta aaatggtgac agtaacagca cccatgtcaa agtgtggttg    16080
tgagaacgaa acaagatagt ctatgtaaag tgattaaaac agcgtaggca catggtaaac    16140
gcttaggaaa tgtaggctgt tataaagctc agagatgtta agtaactaga tcaagaccac    16200
acagttagag agtgccacag tcttgatttg aacccaaatt tgtctcgttc tggagctcaa    16260
gctgctaacc cttttttcaaa actggaatta aaccaaagtg ctcaccctcc gctttgctgg    16320
gcccctccct gccctcaggt gcatctcttc cactcacctg ccacagcagc ctctgctcag    16380
ggtctgagac tgggaaaggt gagggctacc caggtggccc tgatgttttc tgccagccag    16440
```

```
ctcaccaggt ccctcgcagc aggcggcaaa gggagggagg tttgctgtga agattatgtg    16500
gttcccaaca acaagagcac tgggcctatc tctgccctct cttttctgtg tgtcctggga    16560
caagtcactt ggcttctgtg gctttatttt ctcatgtgcc cagccagggg gttggccctc    16620
atatgcaata acagcagcaa tgacctttac tgagtgtcca tgtgcatcaa gcacgtgtac    16680
tttacacttg ttcttattat taggtttaat aatagaataa ttgccacatt tactgagcac    16740
tcattatggg ccaggccctg ccctaagtgc ttaattagct ttagctcctc taatccttac    16800
cttatcccca cacggcatgt tatgttatcc ccattattca gttgagaaca ttgaggctca    16860
aagaggcaaa gtaacttgac caaatacttg taaacgatct tgcatgcccc ttccagctgc    16920
catttagtaa gactctaatt tcataccacc ctaaatctcg tctgcttccc cctcctcctt    16980
ctcaccatct ccccaccgag cagtcggcca agatctgacc gtgatggcgg cccttggctt    17040
gggcttcctc acctcaaatt tccggagaca cagctggagc agtgtggcct tcaacctctt    17100
catgctggcg cttggtgtgc agtgggcaat cctgctggac ggcttcctga gccagttccc    17160
tcctgggaag gtggtcatca cactgttcag gtattgggat ggtggctgga tcacttctgg    17220
gtcatagagg gaatggaccc cgaaaggaca ggttccagaa gatctgggat attgccccct    17280
ctctgtctag caccagtgct gtgcaatatt taggacatcc ttatgctaaa agattattca    17340
ttgtttaaaa ttcaaattta actgggcatc ctgtatttta ctggacagcc ctactctgtg    17400
tatcacaagg aatccaggcc tacattcctc ctgcatcctt tctttcctgt tattgtcgat    17460
tatgattttg taaagttaca taatcagtat aagtttatgg aaaacgtaag aaggaaacac    17520
gttagacaga gagaaataga catgccacac ctagagagac attctatttt ttttttttct    17580
tttttgagac ggagtttcgc ttttgttgcc caggctggag tgcaatggcg ctatctcggc    17640
acaccacaac ctcagccttc tgggttcaag cgattctcct gcctcagcct cctgagtagc    17700
tgggattata ggcatgtgcc accacacctg gctgattttg tatttttagt agagataggg    17760
tttctctgtg ttggtcaggc tagtctcaaa ctcctgacct caggtgaccg gcctgcctcg    17820
gcctcccaaa gtgctgggat tacaggcatg agccaccgcg tccagcctga gagacattct    17880
cttgaaaaga aaggactttc agccccctaa agctactaga caagaaatag ccatgccttt    17940 atttttcatta aattacctgt gctttgttta gatgcctttg tgtgaaatgc taagaaccat    18000
cacaactaat gtatggtgcc agaagtcaga atagtggtta cctgggcagg aggtggatat    18060
tgattaggaa ggaacacaaa atagccccat ggggtgcaga aaatgttctc tgtgttcacc    18120
tgggtgatga ttacacatca agctatacac attttaaaag ggcattggca cttaatagaa    18180
ggaactaggc taaattttt cctgaaacat tgttttgttt tgttcaaacc tctgaatctc    18240
tcagctcccc agatgatggt aaacgtcatc ctaggcatct tagggacctc tcaaggcctc    18300
tcaaggccat tccagcctcc ccttctaaga ccctgctaaa cctctgggca ctgctgttaa    18360
acatttctct atgagccagg aactgtgctg agcactccac aaatattatt ttgtttaact    18420
cttccaggta gggatctaac ctggtataca ggtaaggaag tggaagctca gagagggcaa    18480
ggcacttgcc tagggccaca cagctaagtg gtggagatgg ctctaacttt ttttataac    18540 cttttccaca tgctccagag tggtcagaac atgaaacaca gtctagccag ctcctgactg    18600
gccctagagg aaaaaaactg tatgtatttt tctttttaa aaggtttaga ggctgggcat    18660
ggtggttcac gcctgtaatc ccagtacttt gggagctga ggtgggcaga tcacttgagc    18720
ccaggagttt gagaccagcc tgagcaacgc agtgagaccc tgtctctgca gaaaatagaa    18780
```

```
aaatcagcta ggcgtggtgg tgtgcaccca cagtcccagc tacttgggag gctgaggcag    18840
gaggatcacc tgaacccagt gaggctgagg ctgagtgagc catgatcgtg ccactttact    18900
ccagcctgga caacagagtg agaccctgtc tcaaaaaaca gttttagggg ccgggcgcgg    18960
tggctcatgc ctgtaatccc agcactttgg gaggtggggg tggcagatc atgaggtcag     19020 gagatggaga ccatcctggc taactcggag aaaccctgtc tcgactaaac atacaaaaaa    19080
ttagctgggc gtggtggcgg gcgcctgtag tcccagccac tcgggaggct gaggcaggag    19140
aatggcgtga accttggagg cggagtttgc agtgagccga gatcgtgcca ctgcactcta    19200
gcctgggcga cagagcgaga ctctgtctca aaaaaaaaa aaccaaaaac aacagtttta     19260
ggccaggcgc ggtggttcat gcctgtaatc ctagtacttt aggaggccta gacagatgga    19320
ttacctgagg tcaggagttc gagaccgacc tgagcaacat ggtgaaatcc tgtctctact    19380
aaaaacacaa aaattagctg gcattgtgg caggcacctg taatcccagc tacttgggag     19440
gctgaggcag gcgaatcact tgaacccggg aggcggaggc tatagtgagc cgagatcgcg    19500
ccattgcact gtagcctggg cgacagagtg aggctccgtc tcaaaaacaa acaaaacaa     19560 aaaccatctt agagttaatt cccaccggga ttcaatacac acacacacac acacacacac    19620
acgcacgcac gcacgcacgc ccgcatacac acactgcatc cacctggaaa gtgacaaagg    19680
gcaccctggg gggaattcaa atggtggtgg ccctggtttg gtgttgctgc cttagcttaa    19740
ggtcacacca gccttcagcc tcctgcccca cagtctaggg ctgctccctt catctgatgt    19800
ccacagggac ctgttcattc ttgactcaat ccaggaagat gagaagggag agaagtcact    19860
cgcagcctga gtgaactccc ttgctccacc cctgactgct tggatccccc tagggggtgac 19920 ccctgctgaa actggctcct tcctgaccgg ttcccgtcag ggctgtgctg atgggtggtg    19980
cccaggcctg cccctgggga cggggtactc tcccttggca acactccagc ttgtgccact    20040
tgacttggga ctgatttggt tctgtttga gtcccttcag gggaggggcc tatcttattc     20100
aacgttgttg tttgttttcc tcacatactg ataacttagc aaatggctat ggaacaaaa     20160 atgaaaataa atggaaccct gaagtgggat gttttaaatt tttatttatt atttttttag    20220
agacagggtc ttgctctgtt gcccagtctg gagtgcagtg gtacaatcat agctcactgc    20280
agcctctgcc tcctgggctc aagtgatcct cccacctcag cctcctgagt taaattttt     20340 tacagacgcc tgctaccatg cccggctaat ttttgtgttt ttagtagaga cggggtttca    20400
ccaggtgggt caggttggtc tcgaactcct gacctcaagt gatccacccg cctaggcctc    20460
ccaaagtact gggattacag gcgtgagcca ctgtgcccgg cctaaaactg tgtttgagac    20520
agggtctcac tctgttgtcc aggctggagt gaagtggcat gttcatggct cactcagcct    20580
cagcctcact gggttcaggt gatcctcctg cctcagcctc ctaagtagct gggactatgg    20640
gtgcacacca ccacgcctag ctgattttc tgtcttctgc agagacagga cctcactgtg     20700
ttgctcaggc tggtctcaaa ctcctgggct caagtgatct gcccacctcg gctccgaaaa    20760
gtactggaat tacagcctcc tgagtagctg agaccacagg cacacaccac cacgcctagc    20820
tttttttttt tttttttgc tttttgtaga gatggagtct cactatgttg cccaggctgg    20880
tctcaaactc caggccttaa gcaatcctcc cacctcagcc tcccaaagtg ctaagattac    20940
aggtgtgagc caccattcct ggccttaaaa gtgtgatatt tttaatgtat tttgaaatct    21000
gcaggactct ccctagaaga taatagcaat aaccaactcc tttattgtgc ttgacgtata    21060
tcaactcact ttgcccttac cgtggctcca gaggcattgg gtccaccta taaatggagg     21120 caccaaggca cagagtgatt aaataagttg cccaggatca cacagccaga aagtgtctga    21180
```

```
gtcaagattc cagcccaggc agcctagacc tgagagcacg ctcctaacca ctgcacatca  21240
ctgtcttagc acctcctcag cacaaactgg cccttgagga atgaaatacc gccgccggca  21300
cacacgctcc tgagttaagc ctttgtcaat gaaatgaaca cccacttaaa aggaataacc  21360
tgtccaggca cgatggaaca ttgaataacc ccttattcta aattcctggt ccctgtaaga  21420
ctccttcccc atgcccttgc ccttttatga ccttccccta aagtccttga ggcttaagcg  21480
ggcatagtct gcagcaaaca ctggggaagc tgagtccaga cttcagagca caggctttgg  21540
atctaggcca gctggatttg aacctcacat ttgtgatcag ctggcatgac tgtttccaaa  21600
aagtccattt taatcctcta cgtgaccctc tgtaaaatgg ggatactgaa cggtgagcta  21660
gcacgatttt acagagagtg aatttttttt ttttttttt tttgtgagac agagtcttac  21720
tctgtcgccc aggctggagt gcagtggtgc aatctcggct gactgcaacc tctgcctccc  21780
gggttcaagc gactgccatg cctcagcctc gagagtggct gggattacaa gcatgcacca  21840
ccatgcccgg gtaattttg tattttagt tgagacagag tttcaccatg ttggccaggc  21900
cactcttgaa ccctggcct caagtgatcc acctgccttg gcctcccaaa gtgctgggag  21960
tacaggcatg agccactgcg cccagcctta tagggttaaa atttaaaaga ggtgatgctg  22020
ttacaagcct gttttacaaa atgctcttat aataaatcat tatcatcact gttgctgtgg  22080
ttgtagcatc atcatcatta actcccagag ggaggaggga gtctcagagc aagctgctca  22140
ggggagactg gatgtccatg gattgtccag ctcagtacca cttcctccag gaagtcctcc  22200
ctgataagtc cagtcagcat caccctctcc ttccaatgaa ccccactagc cttgtgatat  22260
cacagatatt cttagttgac aggctcatgg tgtatgtagc ctgtctagat cataagtaca  22320
tttttttttt ttttggatca taagaacctt caagaccaaa ataatttct cctcctgagc  22380 atgctcattg gtcaagggaa ggaaggaatc gtaatagtgt taataaggct agtgtctttt  22440
caggagttgg ttcttttgtgc cagtcttggt gctagacaca ccgataggaa gaatactcct  22500
tcacatcccc aggacaccaa catgggatac gtttgatcat cattcttaat ttgcagaagg  22560
agaaatagga tcagtgagat gaaatagcca ctccagtggc aaggctggga ctggaagccg  22620
ggcttgtcct gattccaaat ccagtttctt tccactgcca cggagaggga gagaagggac  22680
agtggcccca gatgaggatg gggtgactgg atgtgggcag gcctgcgggg gaagagtgcc  22740
ctctgttgag catccgaatg atggcagcag aaaagaagac tggcagaat cccagttatc  22800 agatcccctg agggaacagt caccccgatc accctcagtc agatgagtgt gtgtagatca  22860
atgcctcata gatgaaggca ctgaggcaca gagtggttaa gtcatctgcc agaccacatg  22920
gctcagggtg cagaggccac cttaacggga gaagagatgg tcactccact ctgcagcatc  22980
agcgcccagg tgggtagaaa tcttgtcttc tattccaca gaaagtaagg tgcccaacag  23040
tgtttgttga atgaatgaat gaatgaatga atgagtgaga ggcatccttc cttctcagtc  23100
atcctggctc tccttctcac ccccagtatt cggctggcca ccatgagtgc tatgtcggtc  23160
ctgatctcag cgggtgctgt cttggggaag gtcaacttgg cgcagttggt ggtgatggtg  23220
ctggtggagg tgacagcttt aggcaccctg aggatggtca tcagtaatat cttcaacgtg  23280
agtcatggtc ctgggaggag ggacctggga gaaaagggcc aaaagctcca tttggtgggg  23340
cttccggggt tttgaaaaat aaagacaacc tgtaatccca gctacttggg aggttgagga  23400
gggaagatca cttgaggcca ggagtttgag acccgcctgg gcatcatagc aagatcctca  23460
tctctaaaaa gtaatttttt ctaaattatc cagttgtggt ggcatgcacc tgtagtgtca  23520
```

```
gttactcagg aggctgaggt gtgagttgga aggattgctt gagcccagga gttagagatg    23580
aacctgggca atatagcaag acctcatctc taaataaata ggtaggtgga tagatagata    23640
gatagataga tagatagata gatagacaga cagacagaca gacagacaga cagacaggct    23700
gggtacagtg gctcacacct gtaatcccag cactttggga ggccaaggag ggcagatcac    23760
ctgaggtcag gagttcaaga ccagcctggt caacatgggg gaacctcatc tctactaaaa    23820
atacaaaatt tagctgcgca tggtggcagg tgcctgtaat cccagctact caggaggctg    23880
aggcaagaga atcgcttgaa cccggagggt ggaggttgca gtgaactgag atcgcgccat    23940
tgcactgcag cctgggggac aagagcaaga cttcatctcc aataaaaaaa aaagaaaaaa    24000
gaaagaaaaa gattgataga tagatagata cccaaatgag gttacaaaag tgtggtctgt    24060
gcaaatgttt aaacacaaca aaccagtgcc tttaactact acagtataat cctgtaggat    24120
tgtgctattc atgatgtaat tatggttgta taaaagtaat taattctcag agcctcacca    24180
gcagtgggtc cagcaagttt gtacagccag catcttcttt cagtcagtgc gtgtcagtaa    24240
ctgcacatgt cctctcattg ggagagcctg tcgaaagtct aagtttgaag gcagctgtga    24300
aggtaaggcc aatccaaatg gctctcccag ctcctctgct gtaaccctga ccctgagtga    24360
ggacatagcc aaccttccca tctcataggt gagaaggctg atgcctggag aggggaaggg    24420
actgcccaag atcacatagc aagatagtgg cagaacccaa gcgagaaccc acagttccag    24480
cctggcttag aagaaagtgc actggacttg gagtcaaagg ctggggtgtg catcccagct    24540
ctgccataaa tccctgtgtg actctgggca atttaacctc ttagagcttt agtttcttcg    24600
tctgtaatat gagggtagca gtactaccac atagggtttt gagggagtaa ttgaattaat    24660
cacatgaaat gatgcacgtt tacaaaaaaa agcatgaagc ccctttactg tgcctcagta    24720
tcccaaagga ctttggattt actctgagaa atacagggag aactaggag tgttgggcag    24780 aggagagcta tgatctgact tatgttttaa gatactctgg cttctgggtt cagaaaagac    24840
tgaaggggca agagaggaag caggtggaga ccagagcagc agtgatggcc atcatccaga    24900
ctcagactag gacaatagct gtgagggtgg tgggaagtga ttggatcctg actatatttt    24960
aatagcagaa ttgacaggat ttgctgatag actgcacgtg gggtgggaga gggtcaagat    25020
gacttcaagg ttctcatctg gcacaactca gcagctgctg gtgccattta ctgagatggg    25080
gaacattggg gtgggataga tctgggaggg aaaacccaga gttcagtgtc gaatgtggta    25140
gcgttagggt taaggttggg gcgggtagag atgtgtatga acatcccag tggagacact    25200 gaatggagat gtacaagtct gaagcttagt ggaaaggtta gggctaggga tataaatttg    25260
ggagttgtta caatacagat ggtgtttaaa gccatgagac ccaaggagat cactcaggag    25320
tgaggataaa gagagatggg aagaagtctg aggactgagt cctagaacac cctgcatttt    25380
agagggggga catgtgtaag agccagcaaa ggagacagaa ttgtgcttgg agaggcagga    25440
ggaagcccag gagagcgtga ggtcctgaa ggcaaggaaa gagagggccc caggtgggct    25500
gaatgctgct gagaggtcaa gtcggatgag ggctgggaag tagccattgg atttgacaag    25560
gagaccttgg catgcatggt tgtagaggag gatgaaggca aaagcctggc ttgactgatt    25620
caagagcagg agatgagaaa gtggagacag catgcagggg cagccctgcc aaggactttg    25680
ctctaaaggg gaacagagaa atggaggaga agcaggaggg caataatccg atagagagga    25740
aaaatctgat gatacagaag agagatgaac tgcaagagtc aagcctttga gttggaaagc    25800
aggagtggga ttttgagcac tgatacccttt aggccgatgc agggacagtt catctttttt    25860
aaaattatta ttattataca acatttttatt taaaaatttta ttttcacaga atacattttc    25920
```

```
acattagaga ttcccattgt gcgaaaataa caatttatta cttatagttt tatatttgtg    25980
gacagattgt tttagaacaa gtagaataca tttgagaatt aaatctcagt ttacaatggg    26040
taatattttg atacgtctat ggggaaactt gcccttaaat ggaacttctg tatcttcaga    26100
agcactccaa gcgtttcttc ctaggattta gaaatttata atatgagata tcagcatttc    26160
ctaattttaa aatttcccta gtatatgtaa ccatcggtag gtggtatcta ccgactagag    26220
agggaagttt ttgaaaatta aacactgtct aattttctgc aaagttttta ttcatgaatt    26280
aagagtattt cccttagtcc attattccca aggcaaatat ggaagtttga tcatatgcta    26340
atcatactaa agctggattc tctttaagag attgagaaat taaaaggcaa aagctgatat    26400
atcatgttta gttatactgt gagtcttata agaagctggg aggcaacccc attaactcac    26460
cagaatacag aactcagtct cacaacttaa atataattcc tctcaaacct tttcctcaaa    26520
gttaaattct gaaataatc ttgtgattaa gagaagaagg ctgtccacca atggacttat    26580
ctgttatttc ttccttattg tgagcttaat ggcatgacaa agcagaggca aagaggcata    26640
catcaattct tcaaagtagg aagtcaaaaa ggtcagagct tccacagcat ggcaacagct    26700
ttgcagatgc ccacatcgtg atagttgaaa tagcaaagcc cagcaaaggt taaagctgaa    26760
aatgccaaaa gccctgcctt ggcagctttc tgcgaggcat ccccatgaac atagtcagta    26820
acaacttgtc caaggcccca gtgaccatga agagtgaggg ctgcagccag ggaatagtcc    26880
gtcgcagagc aaggattcaa ataagcagcc ggaagcagac ccgggagcaa aacactgaca    26940
accctctcgc tagtccagtg gagagatgca gccttggagc cagaatggtg gctcggtgac    27000
aagtgtatgt gctgcactcc acaccattct gggataggtc ggtcctgaag aaatgctgag    27060
atatgagcag gtctgaccac tggagttcgc agcaacagag ctcggcctcc ttgggcaccg    27120
caaacggcac tcagcctcca gagaaccgcc atctcgttcc tgaggcggag agttcatctt    27180
aacgagagaa atggcaggga ctgtgaatag gccggcagat ttggtggcgg gtgccacagg    27240
ttcagtctcc tgcagggaga ggagaaaatg ccttactaat tccttgtatt ttctcagaga    27300
aacaagaggc accgtcatca gcctcatgtg agggtgggaa ggaggatgg ggtttgcgga    27360 gagggaaagt gtggtatggt catctgtggg agtggaagag agtgagaggg ctgcagggt    27420 gcagcgggac tgcaggctgg caccagggtc cctagggctt gtagttggtg aaaagtgcat    27480
cagtgaccag ggctgtgtgc agctgctcca ggcaggtgtg gaagaagcag agttgaactt    27540
gcccagcctg gagtgctgcc cagagtgagc ccaaagccca agggagacca gagatggggc    27600
tgtttgcaaa ggaggaagta taacagtagc ccacaaaatc tgagctggtt aagaaaggag    27660
agagagtgaa aatggggagc ccagcctggc agcctgggta cacatctcag ctcaacccac    27720
actagctgaa tccatttggg ccccttcgtt gacctctctg tgcctcagtt tccctatcta    27780
tagaatgggg ataagaataa ggctacttcc tagggctgtt gtgaggattg aacaagtgac    27840
cgaacacttg ttcaattttg aatactgttc taaagcattt aggacagtgc ctggcatggg    27900
gtaagtgttg cggcagtgct gttatttca tcatcaccat tgttctcagg ctgcgttgat    27960
tggagctgct gaagggaggc aatttaagga agtgagccgg acagatagga ggtggtggtg    28020
gttatcaggt gcgatgcttg aaactgaggc ttcgaggca acagttactg gtaatgacaa    28080
ggtctaaggc ttgacagtgg gtggcagaag tgtaacgcag ggaaagagac gagcggtcaa    28140
ggagccgaga gggaaggagt tgggtggact aagatcattt gtggaagaat gatgagaga    28200 aaggctgaag ggcaggaact gacatcatca gtgaccaagg ggcggccagg aggctgagac    28260
```

```
cgcagcaaga aagggagagt gtgatggcat cttcttcaag ggagctgggg atgtttgggg    28320
tggaaaaaag aacaatggtc tgggagggaa tatgggaagt tttttttttt tttttcagat    28380
ggagtttcgc tgttgtcacc caggctggat ggcaatgttg caatctcggc tcactgcaac    28440
ctctgccttc caggttcaag tgattctcct gtctcagctt cccgagtagc tgagattaca    28500
ggcacacacc accacgcctg gcttactttt gtattttag tagagacgga gttttgccat    28560
gttggccagg ctggtctcaa actcctgacc tcaggtgatc cacccgcctt ggcctcccaa    28620
agtgctggga ttagaggtgt gagccaccgc gcccagcctg gaagtttgta tttattaatt    28680
tttggttgtc ttcatctgtg tatgtgactt taacccctaa atacttcagt gtacatttct    28740
tttttttttt tttttttttt tgagacagag tcttgctcca tcacccaggc tggagtgcag    28800
tggtgtgatc tcggctcact gcaacctccg cctcctggat tcaagcaatt cttgtgcctc    28860
accctcccga gtagctggga ttaggggcat gccaccatgc ccagttaatt tttgtatttt    28920
tagtagagat ggagtttcac catattggcc aggctggtct tgagctcctg gcctcagttg    28980
atccacctgt ctcagcctcc caaattgctg agattacagg cgtgggccac cataaccggc    29040
ctcagtgtat atttctgatg cagttgggtt ctgtatcccc ctccaatctc atctcgaatt    29100
gtaatctcca cgtgttgagg gcaggacctt gtgggaggtg atgggatcac aggggtggtt    29160
tcccccatgc tgttcttgtg acagtgagtg ggttttcagg agagctgatg gtttgaaagt    29220
gtggcacttc ctctctctct ttctctctct ctctcacctg ccaccacgta agatgtgcct    29280
tgcttccctt tcaccttcca ccatgattgt aagtttcctg aggcctctcc ggccatgcca    29340
aactgtgagt caattcagcc tcttttgttt ataaattacg cagtctcagg aagtatcttt    29400
atagcagtgt gaaaacagac taacacaatt tcctaaaaca aggggacatt ctcttacata    29460
accattgttc agttaacaaa aatgagaaat tgacattgat atattatgat taccttattc    29520
tcatttcacc aatttttca ataatatcct ttctagaaaa aaatacatat ttttgtggt    29580 cgaggattac atcttgcatt tagttctcat gtccttattaa attccatcaa tctgaacag    29640 tttcttcatc tttctttatc tttcatgacc ttgacatgtt ttgaagtttc gagccagttc    29700
ttttgtagaa tgtgggtttg tctgctgttc ctcatgatta gattgtgggt atgcattttt    29760
ggtaggaatt ctccaagagc cgtgtgtgcc cttcttagta tatcatatca gaagacatgc    29820
tatcaatttg ccccattact gggtgtgtta actgtgatca ttgggttaag atggtacctg    29880
ccaggatctt ccactgcaaa gttactattt tccccttgt aattaataaa catcttgtga    29940
ggagataatt tcctatagaa atcctgttga tcatccaact ttcacccact gattttagtg    30000
ttcattgatt cttccctgaa taaattagta ctataataat tgccaatggt ggttttctaa    30060
ttccatcttt ccttcaatag ttggcattct cctgtaagga aaagctttcg cttctctgtt    30120
catccactca tctatgtatt tgtttatatt accatggact cctggattcc ggtttacaca    30180
cttccatttt ctgcctttc tctctgctta atataaggat taatgagaac tccctgattc    30240
ccaggaagaa aatgtcacca gagctttctt aggtggaatg aagagaattc agtgtaagaa    30300
ccataaaggt gtatctgtgt agtatggaca gttttaaaaa acaaacaaac aaaaagaacc    30360
tccaagggca ggaagtgctg ccagactcag gagggcacta gaactgacta tgagaagcca    30420
ctgagatccc aggtagtctg tgctctccat cttttggctc tgattctctc tgtacatcta    30480
acatctctgt acaccagctt tctctttagc gaaaaacgtg tcccctccac ccacccatcc    30540
acctccactt gttcctgcat ttctatgtcc cagatcctgc agaaaacaac tcttttctct    30600
cagttagtct caattctgta gtccagggag agagaatctg atcagtcccc tgggtcattt    30660
```

```
ttccactctg gtccaagcag ctacagctgg catgggaaat agttcacaca gtaaaaacat    30720
ggctgtcaag aagaggagta aatttcagag gcagaacact ccctgtgagc ccgaacctct    30780
tcctgctttg ttgcagtctt cataacgatt gctttaaaag actgcattga tataacatca    30840
tctctcttct ctgcatcttt gacttgctag cttaactggt ctagaggagg gcttagcact    30900
gattttcagt attcattttc ctcaaaactt caattcagcc tgggtttctt cagcaggagg    30960
gctcggggga accagagcca gggaccagag tcatttcagt gcaccagctc aagaaatgaa    31020
tattccaggc caagaatccc caagtgttct ttctgaagtc cttcctggtg gagctcaaag    31080
agatgaaaaa cgcaagcccg cttttcagtt cttatcagga aactgcatag actttcctct    31140
ttatgtatga ctgagggctt tttaccatca tttgttcact tcacagatat ttatttggta    31200
tttactatat accaggcact cttgtggcag tggaaaatac aactctcgtg gaacatctgt    31260
tccagaagga aagactgcca ataagcaata aaataggcaa aagatatagc atgttagaga    31320
gtggtaagta ccacagagaa aaataaaatg gagaaaagaa acacgaaaag ttggggagag    31380
aggacaactg tttgagggg tggccagggg cagcttcatc tcatcaaggg ggtgattttt    31440
tttgagtaca gacctgaagg taacgagtgc acaagccaca tgggtacctg agaacagcgg    31500
cagaacaatg gcagggtgct gggagggcta tttaccaccc atgctgttta gaattgtcag    31560
cacatggtga taaaaaaaaa aataggctgg gtgcggtggc tcatgcctgt aatcccagcg    31620
ctttgggagg ccaaggcgga tggatcactt gaggtcagga gttcgagacc aggctgggga    31680
acatggtgaa accccgtctc tactaaaaat acaaaaatta gccgggcaca gtggtgggcg    31740
cctgtaatcc cagctacatg ggaggctgaa gcaggagaat cgcttgaacc cagtgggtga    31800
agtttgcagt gagccaagat ggcaccactg cactccagcc tggcgacaga gcgagactcc    31860
gtctcaaaaa taaataaata aataaataaa aataaaaagc agacagactt tttagttggc    31920
tttagaattg ttagacaccc tctgcagaca aggcacccg attgcttgca cccagggtgg    31980
actactccct ccatcctgcc cttgttacac cctggctggg ggtcagcatt tcaggcagct    32040
gaatgaccca aagtgggaac acgctagtgg gtttgaggat gagcaagtgg aggagtgcaa    32100
taggaggtga cgcccgagag gtcaggtgag agtggatcct gcagggtcgt ggcaagaacc    32160
tggaccttga cttgagtga catgggagcc gctggaggct tctgagcaga ggagtaacat    32220
gatctgactt gcattttatt ttatttattt atttgacgca gtctcactct gtcgccgaag    32280
ctggagtgca gtggcgccat ctcagctcac tacagcctct gcctcccagg ttccagtgaa    32340
tctcctgcct cagcctccca ggtagatggg attacaagca agcatcacca cgcctggcta    32400 attttttgtat ttttagtaga cagggtttt gccatgttg gccaggctgg tatcgaactc    32460
ctgacctcag gtgatccacc cacctcagcc tcccaaagtg ctgagattac aggcttgagc    32520
caccacgccc ggcctgactt gcattttaac agggtcactc tgtctgctgt gtggagaaca    32580
gtccgcagga agacaagggt ggaaatgggg agaccagtta ggaggttact gtaacaattt    32640
ggggtagcgg tgatggtggc ttaaaccaag atggggtcag tgggaaatgg tgctaaaaat    32700
cctgccaatt ctgggtattt ttagaaagca cagctgacag cttttctccag tagcccacta    32760 aataagttat gaagcattac taaaatgtga tagtcatgat gcaaaattag aatatatcta    32820
gaatctcccg aagaccttag tttggtatta caagaagtct ggttgcttca tgttgcaaaa    32880
tttatatcac tcatcactcc tgcagagtta aaattccgct gagaagtagg aatcagtgaa    32940
gtgcgtgtcc atgtgggttt ttgccacacc taagtgaacc ttggtcaaaa gcatataaga    33000
```

```
gctactgata ggccgggcgt ggtggctcat gcctgtaatc tcagcacttt gggaggggaag    33060 gatctcttga gcccaggagt tcgagaccag cctgagcaac atagtgagat tccatcttta    33120
cacaaaattt aaaaattggc caggcatggt tgtgcactcc tgtaatccca gctacttagg    33180
aggctgaggt gggaggattg cttgagcctg ggagttggag actacagtga gctgtggcca    33240
caccactgca ctccagcttg agcaatggag caagactctg tctcaaaaaa aaaaaaaaaa    33300
aaaaaaaaaa gaggccgggc acagtggctc atgcctgtaa tcccagcact ttgggaggcc    33360
gaggcgggtg gatcgcctga ggtcaggagt ttgagaccag cctggcaaac acggtgaaac    33420
cccatctcta ctaaaaatac aaaattagcc cagcgtagtg gcgcatgcct gtaatcccag    33480
ctactaggga agctgaggca ggagaatcgc gtgaacctgg gaggcaaatg ttccagtgag    33540
ccgagatcgt gccattgcac tccagcctgg gcaaagcctg ctgggttggg ctgggtaagc    33600
tctgaacacc agtctcgtgg cttcaagtca cacctcctaa gtgaagctct gaactttctc    33660
caaggaccat cagggctttc ccctgggcag aggatgccga cactcactgc tcttactggg    33720
ttttattgca gacagactac cacatgaacc tgaggcactt ctacgtgttc gcagcctatt    33780
ttgggctgac tgtggcctgg tgcctgccaa agcctctacc caagggaacg gaggataatg    33840
atcagagagc aacgataccc agtttgtctg ccatgctggg taaggacaag gtggggtgag    33900
tggtctcata cttgggctga gcagaatggc tcagaaaagg ctctggctga aaaaatctcc    33960
ctcctttacc aacttcccct gggtgtctga agcccttcca tcatgattca cttctttgag    34020
tagtgtttgc taaattcata cctttgaatt aagcacttcc ttttagggac ctctcttcat    34080
taatatccac tagaaaggag agactcatta tgtgtgagtt tcaataagtt tatccaatcc    34140
ctttgttttc aactgaaagg agggaaacgg acaagtgaag aaggtagggc ccaggagtga    34200
aggaacaagg gtgggaatag taataatgtt gtactttgaa aatctactgg gaaaatgatg    34260
aacttagact gctgggagag gctaatagaa aatcgggcag tgagcttgat agtaggcaaa    34320
ggactatcag gccacggggt caagttaaag cagcacattc attaaaaaaa aaaaaataag    34380
cgtttgggcc aggcgtggtg gctcaagcct gtaatcccag cactttggga ggccaaggtg    34440
ggtggatcac ctgaggtcag gagttcgaga ccagcctggc caacagggcg aaaccccatc    34500
tctactaaaa atacaaacaa atcagctggg catggtggtg cacgcctgta atcccagcta    34560
cttgggaggc tgaggcagga gaatcttttg aatccaggtg gtggaggttg cagtgagcca    34620
agatcgcgcc actgcactcc agcctgggca acagagcaag agtccatctc aattaaaaag    34680
aaaaaaaaat taaataagc atttgaccat cacagagcag gttcaggagg cctgggggtat    34740 gcagatttca accctcttgg cctttgtttc cttgtctgta aaatgtggtt agctggtatc    34800
agcttgagag ctcggagggg agacgtgact tccccatcta actctaagtg acaaggctga    34860
gactctccag ccctaggatt ctcatccaaa accctcgag gctcagacct ttggagcagg    34920
agtgtgattc tggccaacca ccctctctgg ccccccaggcg ccctcttctt gtggatgttc    34980
tggccaagtg tcaactctgc tctgctgaga agtccaatcc aaaggaagaa tgccatgttc    35040
aacacctact atgctctagc agtcagtgtg gtgacagcca tctcagggtc atccttggct    35100 caccccaaa ggaagatcag catggtgagc agggcgctgc ccttgggcag cacttgggtc    35160
taacaggact agcacacata tttatgcccc tccccacccc agggccagcg tgggttggga    35220
gagggcatgc cggtggtgg agctgtgcct gcctctacag tggagctcta ggaagaatgc    35280
tgggtggtca caggggcct gggactcagg agactgtcca gtgatcaaag gctttctggg    35340
gggagtgatt aaatccatcc atgctaacat gaaacagacc tgagtttgaa cccgtttct    35400
```

```
gctagttgct caagtcagtc accatgagcg agagtcagca gcaacagact agactagaat   35460
tagccagcct ctctcttccc cccaacaaat ttcaagaatg gaaccatcag aatcagaagt   35520
agagaagtat gtgacactag ccatgtggct ctggtcaagc cacttcaacg ttttgagtct   35580
cagtggcctc atctgtaaag tgagaattaa gagatggtgc atgtaaagtg cttaacgggg   35640
agtaaatggt aggcaaacat tagctgctgc tattagtaca gagagacaat ggtgtgtgtg   35700
agtcttgtgg gcagagatgg gtgagagggg agacaaaaca agttctcatg atgatggggg   35760 caggggggtcc agctggtggt gtcggaggga agtctggaca gaccagtggt ggggctcggg   35820
tgggaggcac tgggggggct ggagtggaaa gaatgtggcc acagatgaca gcttcacagc   35880
agaattcagt gctaagagga agtgagtggc catgagttcc atggtgacag aaagtctaag   35940
acacctagca aggcaggagt gggtgtcagc tcagggaagc tcagaggcta aacctaggtg   36000
agagctgagg gtgtcagata agagcaaggc aaggctccgg ttctggagta gtgaaggaca   36060
tagcagagct ataacccagg aacaaggccc agcttattgg aactgggacc agtcacacag   36120
ggtggcacag gcaccaagta gccaataata ataataaaaa caataacaat gatttatgtc   36180
tattgggcat ttattcatgt tctatgccag acactggact aagagcttta tatgtggaaa   36240
ctcatttaat ccttacaata accttatgaa gaaggtacat ccaaaacccc attcttctag   36300
gccaggtgca gtggctcaca cctgtaatcc caatattttg gaaagctgag gcaagaggat   36360
tggttgaggc caggagttca agaccagccc aggcaacata gcaagaccct gtctctaaaa   36420
aataaaacaa aaacccattc ttcccgctgt ccagggacac accactaatg agtgtgatgg   36480
gtgcctagga tgctgagcac ctggacttcc cagctcattc cctaaatgct gcacaatcag   36540
ggtaactgtg ccctgagcct aagaggcagt agtgagctgg cccaccgtgt ccactgatga   36600
aggacacgta gccccaacac aggggagagg tggtttcagg atcagcaaag cagggaggat   36660
gttacagggt tgccttgttc ccagcgtgct ggtcacttgc agcaagatgg tgttctctct   36720
ctaccttgct tcctttaccc acacgctatt tctttgcaga cttatgtgca cagtgcggtg   36780
ttggcaggag gcgtggctgt gggtacctcg tgtcacctga tcccttctcc gtggcttgcc   36840
atggtgctgg gtcttgtggc tgggctgatc tccatcgggg gagccaagtg cctgccggta   36900
agaaactaga caactaatgc tctctgcttt ggctgaaggc cagcaggacg ctgggacctg   36960
atgggccact gtgcagtgca cagctgcatt aggcaggtgt tggtgcattc tcttattggc   37020
ttcaacgcct agcgagggat ccatcctggc tcggtggcac atttgttaag atgctgggga   37080
gcaggtggca gaacccattt gagcttgctt gggcactggg gagaatttgt taccaggcta   37140
caggggtgtc acagaactca aggacaggga ctggagtgtt gtggggagcc cagaagcccc   37200
tgttttactt ctttctttgc ttttcctgaa tatctgcttt attcttactc tatagacctg   37260
cttcctcctc tttcaccccca cattgtgggg tgtagtcttt tgcttcaaga aagcagcctg   37320
gtggatggaa tctcttggcc ccaatcccaa attctctgga gaaggggctc tttggtttaa   37380
cttggataat gttgtcttca gctgggggtg ggcacatcgt gcatatgtgg ctgctgccgg   37440
ggaaccacgt ggatgatgtg agaggagcag cacccagaag agggagtgct gggctgatgg   37500
tccaggtcgt gtccacttct gattgtttaa ttcttcttct aagtggatgg atctttctcc   37560
aatactcagc aaatcctgat cgttccagaa tacttcatta tagccaattg gttataatgt   37620
gcttctctaa gagaaatatt tagggacaac aaatcttcat gggtttgaag acttgatgga   37680
ggaaaaagga gtagattttc gaaggctgga tttggatgaa caggggctat tcagggagtg   37740
```

```
cattccaacc taaaattagg aaaaactggc tgggcgcagt ggctcacgcg ctttgggagg    37800
ccgaggcggg cagatggcct gaggtcagga gttcaagacc agcctggcca acatggtgaa    37860
accatctcta ctaaaagtac aaaaattagc caggcgtggt ggcgggcacc tgtcatctta    37920
gctactcagg aggctgagat gcgagaatca cttgaacctg ggagacagag cttgcagtga    37980
gccgaaattg cgccactgca ctccagcctg ggcgacagaa caagactctg tcttaaaaaa    38040
aaaaaagtgt tttatataca gagtggaata ttatttagcc ataaaaagaa tgaaatcctg    38100
tcatttgcag caacatggat ggaactggag gtcattaaaa aataaaataa aataaataag    38160
gaaaaacgta tcaatacttc gattgaccaa aaccagggca aatctgattt tcatctttgc    38220
aaggggaaca aatttctttt atctcctctg gctttgaaac cctgaaatga aaggaggaag    38280
ggcagaaaaa agaacacata gcaagttacc atcaggctca gcgcccatcg cattccctga    38340
gcttgtttcc ttgacttcat cactggcagg actattcaaa aatgattccc tcattcattc    38400
atatattcat tcattcatca ttccttcatt caacacatac gttttaacac tcatcttgct    38460
tttcaagcta tagtttagtg agcgaaatgg atacacagaa tacagtgtga gaacagctac    38520
agggcacatc tgagctagcc tgggatgggt ccggaaatgc ttcctggagc agaggaaacg    38580
gttgacagcc aagtgttgac agagaagtag tattagccag gcagagacat ggggaatgta    38640
ttccaggcag aaggcacagt gtgtatgaaa gcttattggt aagaagagtg tgtggcccaa    38700
ccaggaaaca gacattctga aggcataggg tccacccagg agcatggtga acccagatcc    38760
ctgaaagatg ggaggtgctc aggcacactt cctgggctag ttgaggggtc tggattttta    38820
tttacttatt ttttattta ttgagacaga gtctcgttct gtcacccagg ctggagtgca    38880
gtggtgcaat ctcagctcac tgcaacctcc acctcctggg ttcaagtgat tctcctacct    38940
cagcctcctg agtagctggg attacaggtg cccaccacca tgcctggcta atttgtgtgt    39000
gtgtgtgtgt gtgtgtgtgt gtgtgtgtgt tttgttgttg ttgttgttgt tgagacggtg    39060
tctcgctctt ttgcccaggc tggagtgcag tggcgccatc ttggcttact gcaagctctg    39120
cctcccgggt tcacaccatt ctcctgcctc agcctcctga gtagctggga ctacaggcgc    39180
cctccaccac gcccagctaa ttttttgtgt ttttagtaga cggggtttt cgccatgttg    39240 gccatgctgg tcttgaactc ttgacttcag gtgatccacc cacgttggcc tcccaaagtg    39300
ctgggattac aggcatgagc caccgtgccc gacctggatt tttattctga agactaatgg    39360
ggatcctaag gaaggaacca gcctgactga atttgcatat gtgtccacat ctgctggctc    39420
atggctgtgt gggaggctga gtgatgggga ggaaggatta ctgagtaggg atctagaggt    39480
gtggcctcat gctttctttc taaccagctg tgttgtcttt gggatggtgc ttaaatttgg    39540
gctagaccag tgggtcttgg tcacccccca ggggacatct gacaatgtct ggaggcgttc    39600
ttggttgaca cagtggggtg agggctgcta ctggcagctc gtggggagag accaggaatg    39660
atgcttaaca tcctacagtg cacagggcag cccccatcac aaggaattat cagctgaaat    39720
tgtgaatagt gcctacacta gacccttgct actcatagtg tggtccgtag atgagcagca    39780
ttggcatcac ctgggacctt gttagaaatg ctcttagacc ccaccccaca tccactaaag    39840
ccagctcttc atttcaacaa actccccatt gatgtgagta cacattcaag tctgagaagg    39900
gcttctttga ggtgagcctt agtgcccatc cccatttggt ggcgccggat accaagggtg    39960
tgtgaaaggg gtgggtaggg aatatgggtc tcacctgcca atctgcttat aataacactt    40020
gtccacaggt gtgttgtaac cgagtgctgg ggattcacca catctccgtc atgcactcca    40080
tcttcagctt gctgggtctg cttggagaga tcacctacat tgtgctgctg gtgcttcata    40140
```

```
ctgtctggaa cggcaatggc atgtgggtca ctgggcttac cccccatccc cttaacactc    40200
ccctccaact caggaagaaa tgtgtgcaga gtccttagct ggggcgtgtg cactcggggc    40260
caggtgctca gtaggcttcg gtgaatattt gttggctgat ttattcagaa attatgtcca    40320
gcccctacct tggatggatt tatcacctct ccaggccacc tcttctttcc aaataggacc    40380
acctaggtat agaccaaaga cacgaaatct tctgtgaccc cacaaacaca gagcaggtca    40440
aataggccca agccaattga gactgtggtt caggtcgtga tgcagagctt tgctgtggac    40500
gtgctcccac tgcgtactag ctgggcatgc ggcttaacct ttctcagcct cagtcgcccc    40560
cttgtaaatg gagataagga tactatctcc cctcacaggg ctgttgggat gctactggat    40620
ttaataagct aatgcaggga catgctaagc acaacccatc cctgaggccc agagaagggt    40680
gggcctcggc tgaggtctca ctgtgaggtg ggaatgtggg cctccagacc agaggtaggt    40740
cctgtggccc ctagacagtg gacagcaatg gtcagtttga cacaccagag ccctagccat    40800
tacttcctgg atgttgtgtg aatattttct ggacatggct tatataaaat gaaaaagtga    40860
attgggcacg atatagggat agattttttag agatgaactg atagcatgat gataatcata    40920
ttcactgata acatttacta ctgttattga ctgctttaaa agtgttgggc attgtgctag    40980
aaaccattat atgcattatc tccttgaatt ctcacaaccg cctactgagg tattctcaga    41040
ctctaagaaa tgagatttaa gagaagttat ctgcccaagg tcaccggct ggaacctggc     41100 tgtaaaaatg gctgaagcag gtgatgagga gctgatgtgt ttggacgtgt ctcagagaaa    41160
tcatggaggc gctggggttc cttccggttc ttggatgcct tctacagaga caaccatagc    41220
cccaaattat agggatcaca tatcagtggg tgagacatcc ttgcttggga tgaggagggg    41280
atgagctgtg tgaagcaagg tgcctctgta atgggttcca gtgatgtgtc tgccactgtc    41340
ttaataactg tgcaattcta agcagaacct ttcctgtctc tgggcctgag agttcccctc    41400
tgtaagatga ggacttgacc tagcaaggtc ctactcagat gcctgtagag aacaggcagg    41460
ggaagttaga aaaaaaaaaa gccagtgaag gaagggagct cttcagcttg cacccaccat    41520
cacagtgcag ggacccaggc tcagtgttgc cagatccaat gacttctcaa gagctcaaaa    41580
tctagagttt tgcatgtgct ctcccaagta ctggcagaaa attcaagatt gttagtaaca    41640
ctgtgtggct aaattctgct tgtgggctgc ctagattccc aattctgtga ttctgtggtt    41700
ctctggaagc attggttctc cacagcacct gcatcacttg gaaacttgtt agaaatgcaa    41760
gccctaccta cggccccacc ccagacctac ccagttagaa atctgggggt gggacctatc    41820
agtccatgtt tgaacaagcc ccacaagtgt tctcttgcaa gctcaagttt tagaaccact    41880
gacctatagc caaaaagaa aaagccaatc agtggtttgc tggtagagga ttaacttaac    41940
aactggcttt ccatgaaaat aaagccttga ttggtagcac ttgcaatttc tatggtacaa    42000
acgcttccca catgactgag ttcaagctat caaggagacg tcactgcaca tggacttggg    42060
aagagatgag aacaatcagc ccactgagcc tatgggaact ggctccagca catccctgca    42120
agtcaactct catcagggtg agtgagttga ggaccaagaa gcagttatcc tcttgccttt    42180
gcaggaccca ggcaaaggga agggcatagt gacagtgatg atctctcttc cggaagtctt    42240
tggtttgctg agagtaaaag gcgtgggctt caccagtggt gaagccagtc atgcagcctt    42300
agtcctggta ctcaaactcc ctaaatctca gttttctatc tgtaaaatgg gaaataagt    42360 cctatgtcac agggttgctg tgcagattta gcaatagaac atagcccgt tctttatgat     42420 gactgatgct gcatcagtat ggggacatct ctatgtaatg gaaagatgga gagaggatta    42480
```

```
agtgcaaagt cacagcactt aatgggaact gtggattagc tacttggtgg cattgggcaa   42540
gtcagttgac tttgcattaa ttccacaaac aatatttccc aatttcctat tcagatgagc   42600
atatgtgact gagtcagatg ctgtgatcag agccaggatg gagcatttcc cacaaactgt   42660 gggatttta agtgatggga aggcacactg aaatggcatt gaatcatgca gttgcagata   42720 ctcttttca attctcagtc ctttgattac atcagggaga aaagaaagtc cccacttggg   42780
ctgagaatct ctgcaccctt ctagctcttg ttaaccactc ttttgaatag cagagaaaac   42840
ctcagactgc catatctggg agagatttta gcaacatttt gttttcattg tatctctttt   42900
tacagctacc tcccattcc cttctatttc aagctagtaa cacagttttc ttttaaattc    42960
atttatttaa atgtaaaaat aagtctattt ggagaaaaaa aattttaat agcatctctg    43020 gaatgccagt atggctaaat tcatgaatgt tgtcctcaaa tgctgaaatc tgggaagcat   43080
ctggccaagc tttgtggaca ggccttccta gtttgaatcc caagagccac tcattccgag   43140
ccacaaaaca ttggaattct tggttcactt ccctaacctg aacttgtcct ctgtgaaata   43200
gggacattaa tagctcactc acagggctgc tgtgaggaca tgtgttgagc tgagggtctg   43260
gccaggggag accctgtgca gggagactgt tatcatggtg atggatttct gcttcattca   43320 tttcttttc cagacagcat catatagaat gagttgtggg gtggcagtca gcaggtttgg   43380
gtttatcctc tattctgcca cttattactt aaaaaaaaaa acccaactta tatagtataa   43440
gctatatcca gaaaagtgca aatatcatac aagtaccatt tgatgaatct tctgatatcc   43500
ccacataacc aacacccaga acctcttctt gtctcattcc aggataacca ctaacctgac   43560
ttctaacagc atcagtcagt tttgtctgtt tttgtacatt atatatgtga tggtttgaat   43620
gtgtccccca aatttcatgt gctagaaact taatccttca attcatatgt tgatgctatt   43680
tggaggaagg gcctttggga agtaattagg attagataag gtcatggggt gaggtatgat   43740
ggcactggtg acttataaga agagaaagag aaatctgagc tggcatgctc ttgccctctc   43800
accgtgtgat gacttctcca tgtcatgatg cagcaagaag gccctcacca gatggtggca   43860
ccatgctttt ggacttccca gcctctagaa ctgtgagcta aatcaattta ttttctttat   43920
aatcacccag tttgatattt tgtcatagca acagaatatg gacaaagaaa gaaaattaat   43980
gcaagaagta gagttttta tgtaacagat tcctgaaaat gtggaagtgg ctttggaact   44040
gggtgatggg aataggttgg aagagttttg aggagcaggc tagaaaaagc ctgtattgtc   44100
aagaatggag cattaggcca ggcacggtgg ctcagactta taatcccagc actttgggag   44160
gccaaagcag gtggatcacc tgaggtcagg agttcgagac cagcctggct aacatggtga   44220
aacgctgttt ctaccaaaaa tacaaaaaat tagctgggca ctctggcgca cacctgtaat   44280
cccagctact caggaggctg aagcaggaga atcacttgaa cccaggaggc agaggttgca   44340
gtgagctgag atcgtgctat tgcactccag cttgggcaac aagagcaaaa ctccaactca   44400
aaaaaaaaaa aaaagaaaa agaaaaagaa tggagcatta aagacagttc tacagttctg   44460
gtgagggctt aaaagaagac cccagaacta gggaaagtct ggaacttctt aatggttact   44520
gaagtcgttg agatcagaat gctgatagaa atgtggctgg tgaaggccat tctgatgagg   44580
tctcagatgg aactgaagaa ccacgtgttg gaaactggag caaaggtcat cctttttata   44640
aagaagcaaa gatcttagct gaactttgtc tgtgccagag tcatttatgg aaagcagaaa   44700
atccgtaggt cacccatgtt gtagagaatg aaagaacatt ttcagctgag aaaactgaga   44760
gtgtgaccaa gctaccgatt gataagaaaa ctagtacaca taaattagcc aggcgtggtg   44820
gtgggcgcct gtagtcccag ctacatggga ggctgaggca ggagaatggc atgaacccgg   44880
```

```
gaggcagagc ttgcagtgag ccgagatcgc gccactgcac tccagcctgg gcgacaaagc    44940
gagactccat ctcaaaaaaa aaaaaaaaaa aaaggaagaa agaaaattag tacacataga    45000
acaaagccag aggctgttca tcaggacaag ggagaaaaac tccaaagcca tttcagagat    45060
cttcaagact gccctccca ttactggccc agagctctaa gagggcagaa tggtttgaa     45120 tgaccagctg ctgcccaggg ctgccttggg tctctgctcc ccacatttct ggtgcagcat    45180
tcctcagcca tccagctgt ggttcaagtg ccacaggtg tgatgtggaa ggtaaaagtc      45240
ataaaccttg gcagcataca catggcacta attttgcagg tgtgcagaat gcaaaagctg    45300 aggggggcatg ccttctccca cctacatttc aaagggtgct gtgaacggcc accccagaga   45360 gccctagta gagcaaggtc tagtggagct acaagggtgg ggccaccgcc aagaccccag     45420
aatggtagag ctatcatagt gcaatgccag cttgggagaa ctgcaggcat gagactccaa    45480
cctgtgcgaa gtgcaacatg ggcagaaccc agcaaaacca caggggcaga gctccccgaa   45540
gcttcggggt tccaaattcc atagtgtgtc caggaggtgg cacacagagt aaaagatcat    45600
tctgaaggtt taaggtttaa tgttgttttc tatgttgggt tttgtacttt cctggaacca    45660 gttaccctt ttcccttgcc tcttttttcct tttagaatgg gaatgtctgt cctatgcctg    45720
ttccactgtt gtattttgga agtcaataac ttgttttgac tttacaggct tacagccaga    45780
gggaatctcc catagaatga attgtaccctt aagtctcacc cacatctgat ttagatgaga   45840
ccatggactt tggaattttg agttggtgct ggaacaagtt aagactttgg gggttgtcta    45900
agtgtggtgt ttcatgcctg taatcccagt gatttgggag gctgaggtgg gaggattgct    45960
tgagcccagg agttcaagac cagcctaggc aacatagtga gacctgtctc tacaaaaata    46020
aaaataaaaa gttagccagg tattgtggca tgtgcctgta attctagcta ctcaggaggc    46080
tgaggtgaga ggatcacttg agcccaggag tttgaggctg cagtgagcta tggtcgtgcc    46140
actgcattcc agccagggca acagagtgag actctgtctc tacaaataag attaaataaa    46200
cgtagctgga gatggtggca cacgtctgta gtcctagcta ctcaggaggc tgagacagga    46260
ggattacttg agccaaggag tttgaggctg cagtgagcta tgatcatgcc actgcattcc    46320
agcctggatg atagagcaaa atcccatctt taaaaaaaaa aaaaaaaaa aaaaaatat      46380 atatatatat atatatatat atatatatat atatatatat actttggtgc tattgggatg    46440
aattttgcat gtacgaagga catgcatttt ggggctggg gcagaatgct atggtttgaa     46500
tgcatccctc aaatttcatg tgttggagac ttaatctcca aattcatatg ttgatgaaat    46560
tggaggtgaa gcctttggga ggtaactagg attagataaa gtcatcaggg tggggccct    46620 atgatgagac tggtggctta caagaggaag agagacctga gctgacatgc tcttgccctc    46680
ttgccatgtg atacctctg ccatgttatg gcacagcaag aaggtcctca acagatgcca    46740
gcagcatgct cttagacttc ccagcctcca gaaccatgag ctatatataa ttatttata     46800 aattaccat tctgtggtat tctgttatag caacagaaag tgaactgaga taatatacat     46860
ggaatcatac agtaagtctg tgcttttgta tgcttctttt actcaacatt gtagttgtga    46920
gattcatcca ggttgttaag cattgctgta ctttttttcc actgggatat agtgttctgt    46980
catgcttggg tcttaattta taaggtgac tgagtggcat tttcttccag tattattgga     47040
aggaaagttt tgttgttcac agttcccctg taaaaagag gcagaacacg tcttgcaggg     47100
ccacacaaaa ctgtgtcatc cagggaccag gcagcagaaa gagaggggga actgggccta   47160
tgcctttatg aaaaagagtg gtgggagagt aactgggtga gggcatccac taatgggcag   47220
```

```
gaagtgaaaa cacatatgtt ggaatttgta gctgaggggt ttataatatg agtttcccat    47280
gcctgagaaa gctgacttgc aagaaaacga gataaacaac tttggccatt agtgtggccc    47340
tgtcataaat gaatgccgga tagacaaatc gagaatctaa gaaaagatag ttggaacaag    47400
tgttccattg tgtgaatgca gcagaattta tttatccatt attgaggagg atttgggtag    47460
tttccagttt ggagctatta tgaatattct agtattgctc ctctgaacat tctagcactt    47520
ttgttttggg agcacacgaa tgcacttctg ttgattatat gcctagaagt gaaattgttg    47580
agttatacag tattcacaca gtcagcctta gtggctactg ctaaacagtt ttctctagta    47640
gtttgcgcca atctaatcac cagtagtgta tagaagctcc ttttactcca cattttgtta    47700
acacttggtg ttttccttct ttttgattag tcatttagca gtgaaaccta tttttacat     47760 tttgatatct ccaataacta actaaatgga gcacttttaa tatgcttttt ggacagttga    47820
atatcttttc ttgtgaaatg tctattcaag ttagtttgcc cattttctat tgtggtgttc    47880 tgtcttttc ttattgattt taggaattcc ttacatatcc tggatatgaa tcccactatg     47940
tggcttacct ttttccttct ttcttttga aacagagtct ccttctgtca cccaggctgg     48000
aatgcagtgg cgctatctca gctcactaca acctctgcct cccaggttca agcaattctc    48060
atacttcagc ctcctgagta gcttagatta caggtgcatg ccaccatgcc caccgaattt    48120
ttgtatagac aaaataattt ttggtagaga cagggttttg ccatgttggc caggctgatc    48180
ttgaatccta gcctcaactt tggcccacct tggcctccca aagtgccagg attacaggt    48240 tgagccacca tgcccagccc accttttact ttcttaatgg tgtcttttga acaaggaggt    48300
tcttaatttt aatatagccc aatttatcat tgttcccttt atgcttagtt cttttatgtc    48360
ctgtttaaga attttttgcag ccagctcggt ggctcacacc tgtaatccca gcactttggg   48420
aggctgaggc tggcagatca caaggtcaag agatcgagat catcctggcc aacatggtga    48480
aaccctgtcc ttactaaaaa tacaaaaaat tagctgggcg ttgtggctct tgcctgtagt    48540
ctcagctact cgggaggctg agatcacgcc actgcactcc agcctggtga cacagcaaga    48600
ctccatctaa aaaaaaaaga aatttgcaag gtcatgcata tgtccccctg aattttttc    48660 taaaaatcac ttaattttag atcaatgaat tgagtaattg actccatttt tcagtcattc    48720
aacaaacatt tccctgaggt tttgataacc tgaactgtgt ttggagctgg ggaggaagca    48780
aactattgaa tatatacaaa gatggcaaag atgagggcct ggagcttgcc acacggaagg    48840
ggggatggct gcctgaatgg ttgggcaggt agttgttgac atctgcactc cctacaagag    48900
cagcagggtg gcaactcttt ttatcttttt aatttatttt tcttttctct ttttttttg    48960 agatggagtc ttgctctgtt gcccaggctg gagtgcagtg gcgtgatctc agctcactgc    49020
aaactccacc tcctgggttc acccgttct cctgcctcag cctcctgagt agctgggact    49080
gcaggcacct gccaccactc ccggctaatg ttttgtattt ttagtagaga gggggtttca    49140
ctgtgttagc caggatggtc tccatctcct gacctcatga tccacccgcc tcggcctccc    49200
aaagtgcggg gattacaggt gtgagccacc acacccggcc ttaatttatt tttctagtct    49260
gcaggtaatt ctttttaatt ctctccactc tcctatgatc ttatgaggta gggactgtga    49320
ttatttctcc cactttataa tgaacaatca gtaaagacag ggaagataac caaatgacat    49380
acaaggtggg gtccacccca tgaggctgca ggcttggagc tttcctttgt cttaaaaatg    49440
agaacatgag ctgcccacct gttgagacaa gaaataggaa aggcttaaaa aactggcttg    49500
ttgtgtacaa ctatccgtgg ggctgcagtg aacgggctgg cagtgcccag gtgcatgctg    49560
aaccctggga caatcacatt cagcatccag gggcccccgt aatagcttaa tgtttgaatt    49620
```

```
gaaccccctgg ggttgccttg aaggagagag atcctggaag tatgttcaag gggtagggat   49680
gggcagggga gatgggtctg aaagccaagc tctaccccac ccaccttgcc ccaagagaaa   49740
tagaaccttc atctttaatt gcctaacgag aaaactgggg ctggccagat gtggtggctc   49800
atgtctgtaa tcccagcaat ttgggaggcc aaggcgggca gatcacttga ggtcaggagt   49860
tcgagttcag cctggtcaac atggtgaaac cccgtctcta ttaataatac aaaaattatc   49920
caggtatggt ggcgcatgcc tgtagtccca gctacttgag gcacaagaat cgcttgaacc   49980
tgggggacag aggttgcagt gagccgacca ctgcactcca gtctggacga cagagtgaga   50040
ctccatctca caaacaaaaa cagaaaaaaa aaaaaaaaa agagagagag agaaaactgg    50100
aggctctgag aggttaaagg acttgcccag ggtcttgcag ctagtaagtg acagagctgg   50160
gacttgagct tgggttttct gactcctggt ctggttcatt atccatgagg tgctgggaac   50220
taaaataagc cacaatcttg gaatctccgt cgcctccctc cctcccacat gtctgcgtgg   50280 cttttttggga aaatgccagg ggaatgtacc agccagggag aggacccttg ttttcctcat  50340
ggcccttcct ggcaatggca ctactgacac cgacagtcct ttttgtccct gatgacctct   50400
gctgcctgat gcccaagtga ccacctctgc tttgtcattt ctaggattgg cttccaggtc   50460
ctcctcagca ttggggaact cagcttggcc atcgtgatag ctctcacgtc tggtctcctg   50520
acaggtcagt gtgaggccac ctttcttcca ccattgccag gacacagcac ccacgtccag   50580
agcgcaccct gccgtgtggc tggatgtcta tgtgccccat ctccttccct gaggatcaca   50640
taatttcaga attggaaagg ttcttagagg tcacctgctg ctaatgtgga ctgtgaggcc   50700
agggcaggga agggacatcc ctgaggttat aagtagggtg agtggcaacg ttgcagactt   50760
ttgaacccag ggctggtgat cacactcagt tttgcacaga agcccgagaa aatccttaca   50820
cccaaaagcc tacctttat ttctgaggac acccataata ctattttatt caacagatat    50880
ttattcaata tccactatga gccaggcact ggggacacag cagtgagcaa aacaaattcc   50940
ctgaccccat ggaattgacc ttctagtggg ggaaggtatt agcaataaat agacaaataa   51000
gtgtctacta cgccagatgg gaagaagtgg ctgtgaagac agagcaaact agagaaacat   51060
agagtcaatg tgggatgggg tgttcttta ggggggtggt cagggaaagc ttatctgagt    51120
agttagcttt taagcagaga ccccaatgaa gaggagggag atatgcgatg catttagtta   51180
ggggaagaac attccatgaa aataggatag caagtgcaaa ggccctgaga cagcagcatg   51240
ctttgtgtgt tgagggaaca gtaaggagac cagtgtggtt ggtgtgaatg gagtgagaag   51300
gagcagcagg ggttgagggc agaatggtag tgaggagcag gcccttataa aagatgggaa   51360
gccactggag atctttcaac aaaggggaaa agtatgtttc tgttcttgca atacaataga   51420
aaagcaaaaa atctagggga gttgctaatt agccagtttt acttatatgc caggtgaaaa   51480
tatgtggcta ggtgcagtgg ctcataccctg taattgcagc agtttgggag accgaagtgg   51540
gcagatcatc tgaggtcagg attcaagacc agcctgccca acatggtgaa accctgtctc   51600
tactaaaaat taaaaaatta gccaggcgtg gtggtgggca cctgtaatcc cagctacttg   51660
ggaggctgag gcaggagaat tgcttaaacc cgggaggcag aggttgcagt gggccgagac   51720
tctgtctaaa aaaaaagaa aatacacatt caggccaggc acagtggctc acgcctgtaa    51780
tcccagcact ttgggaggct gaggcaggta gatcacctga ggtcaggagt tcgagaccag   51840
cctgaccaac atgggaaaac cctgtctctg ccagaaatac aaaaattagc caggcgtggt   51900
ggtgtgtgcc tgtagtccca gctactcggg aggctgaagt aggggaatgg cttgaccccca  51960
```

```
ggaggtggag gttatagtga gccaaggttg caccagccta ggtgacagag tgagactgtc   52020
tcaaaaaaaa aaaaaagaaa gaaaatatac attccatcca gaacttgtta ttctacaagc   52080
aaacatcttt tattggttag acacccatat atgtgtccct aagcaggagg tggatgccaa   52140
ataagagaca aatggcgtaa gacactatga gttgtgtggt gacattgggc atgtcacttc   52200
actccctctg agccttggtt agcttctctg taaaatgaaa ggattatggt aactaagctg   52260
gcttccttcc agctttaaca aactgtatgg aggtacattt tggagttact tgggtaattt   52320
ttgagtgtga gattggctag aattgctttta atataccaat gtctggcctt agcttttggc   52380
agagtctgtg tgaagaagca gaggcggagt agagttaatt ccgtaagtta acgttcagtt   52440
cgtggcagct ggcaatccaa ccctgggaaa ggctgccgga tttagcaaaa atgcaaggtg   52500
tctgttttta aattcgcaat gaattgggta tcctgcattt tatttggcaa ccctgtcctg   52560
ggactcacac tattcactgt tatcactggt atattcgaag tggtgctgac ttgccctctg   52620
tcttgcaaag tacccggggg tcttttctta tgcttcactg gagtcaaaaa agagaataga   52680
ggaaaagaca atcatattgt tccttttaaga gttaagacca caagctttc ttctttacat   52740 gttgttttg acatgagcaa actggtgatt aaaaacaact tgggtggctc atacttgtaa   52800
tcccagcact ttggaaagct gaggtgggag aatagcttga ggccaggagt tcaagccagg   52860
gcaatcctat agtgagaccc catctctaca aaagatacaa aaattagcca ggtgtggtgg   52920
tacacctgta gtcccagctg ctccggaggc tgagatggga ggatcagttg agcttgggag   52980
gcagaagttg cagtgagctg agatcgtgcc actgcactcc agcctggaca acagagcaag   53040
accctgtctc aaaaaaggaa acaaaacaac ttggacaatg gaaggggag aaagttcctc   53100 aagaagccaa aattgcacca aatggactcc cagaagccaa gcatttaact tgttaattga   53160
gccctctgtg ggcctgtcta tacttattta aggaacaatc ctatcaagca tagttattgg   53220
gtttctcagc ccaggtagat tagaaatagc agattagagg tgggctaggt ttctagaggt   53280
aaagtacacc agcagaagtt agaagtgaaa gcaaagagcc taacagagga agagaaattc   53340
tttttttttt ttttagacgg agttttgctc ttgttgccca ggctggagtg caatggcgct   53400
atctcggctc aacgcaacct ccgcctcctg ggttcaagtg attctcctgc ctcagcctcc   53460
tgagtagctg ggattacagg catgcaccac cacgcccggc taattttgta tttttagtag   53520
agacagggtt tctccatgtt ggtcatgctg gtctcgaact cctgacctca ggtgatccgc   53580
ccaccttggc ctcccaaagt gctgggatta caggcataag ccactgtgcc cggccaacaa   53640
attcttaaaa ctggacacaa gaacacaaaa cgcttgggct gctgagagat tagaccaaca   53700
accctccacg gctacaaacc ttttccacgt tatatggcac gttataagtg ggtgttccta   53760
gtgatggttc tgattttttt tttaaaaagt ctaaatatgt ttaatgttgt ctcagaagac   53820
aaaatatatt ttagacagat attcctcagt gatgagtaag cctcagctat ctggaaaatt   53880
catgcaggcg ccagagatca ttactgagta attcaagcta ataactgcgt catgctggtt   53940
gtaccctgca tgccaatatc tgctaaaagc agcaccacga aagggaaata cgaatctcac   54000
taagcactca cccattcttg ttaacgacac tggaactgat catccttaat aatacacaga   54060
taaatctatc aggagcattt ccttgcttcc tgtgaaagga agtactcatt ccatgtgtcc   54120
tgtgaaattc agccagcttc gggaagctgg aggaatacat atggccaagc tacctgggca   54180
gagagtagac agggaatgga ggttgggcac agtggctcac acctgtaatt gcagcccttt   54240
agaaggcaaa ggcgggcaga tcacttgagc tcaggtgttc aagaccagcc tgggcaacat   54300
ggctaaaccc cgtctctgca aaaaatacaa aaaaatgagc tgggtatggt agcacacact   54360
```

```
tgtggtccca gctacttggg aggctgaggt gggggggttg cttgtgcctg ggagtttgag    54420
gctgcaatga gctgtgattg tgccactgca ctccagcctg gataacagaa tgagaccctg    54480
ttccaaaaat aaaaaataaa atcaaagaca cttaaaaaga tggggaaaag gaaggacagg    54540
cacttaagca agttataagc tactttccta actacacaag tggaatctta agctgaggtt    54600
cccaggagtt gactggagcc agagaagaca gacctatagg agcacccaac tggagtcgcc    54660
ctccatagta gcccatatgt cttacatgga tcagctttcg tggggccctt ctactccgtc    54720
tggggaaggg cgtcagatct gtggctctca tgtactgctc agtacactgc cattcccagt    54780 tcttttttc aaaaaaaaa aaattgttta cagaatcggc cgggtgtggt ggcttatgcc    54840
tataatacta gcaatttgga aggctgaggt gggtggatca cctgaggtca ggagttcgag    54900
accagcctgg ccaacatggt gaaacccccat cctactaaaa aaaaaaaaa aaaaaaatta    54960 gctggatgtg gtggcaggcg cctataatct tagctacttg ggaggctgag gcaggagaat    55020
cgcttgaacc tgggaggcag aggctgcagt gagccgagat catgccacgg tactccagcc    55080
tgggtgatag agtgagactc tgtctcaaaa taaataaaat aaaataaaat aaaataaaat    55140
aaaataaaat agtctacaga attaagctgg tccaggaatg acagggcgtc catttatttg    55200
tctttcaatt gtgggagaaa aaggatttct gttgagacac tgtcgttttg acacacacaa    55260
tattttgatt aatcttgaga ttaaaaatcc tgtgctccaa atctttttaac attaaattat    55320 gcatttaaac aggtttgctc ctaaatctca aaatatggaa agcacctcat gtggctaaat    55380
attttgatga ccaagttttc tggaaggtaa gattttttcac ctattaacgt gatagatttt    55440
gagtgcatga acttaaaaac atacctgggt atatatgttg acttgctgtt tatgagtaaa    55500
acaaaaacaa aaatggagta aggagcattg caggaggaac tagaggagaa acaaatccat    55560
gatatgcatg tgtgtgggg agggtggcgg ggaggtggta aaggtcacca tttccctgat    55620
acctcaaatt cattcagagt cagggatgag acagctttca ctggccacac ttcccctccc    55680
gctatctgca gtcctcagcg tagccaaata gtttgacatg cgggtgacag aaccccgcaa    55740
tgcaaaagct ggaagaaacc tcaagccttg gagtccaacc cctttttgtga cagatgctaa    55800 gagtggagac atgacttatc aagatcttac aactggctgg gcacggtggc tgacgcctgt    55860
aatcccagca cttttgggag gctgaggtggg gcgatcacct gaggccagga gttcgagacc    55920
agcctggcca acgtgtcaaa accccatctc tactaaaaat acaaaagtta gctgggcgtg    55980
gtagcacatg cctgtaatcc cagttactca ggaggctgag gcaagagaat cgcttgaaat    56040
caggaggcag aggttgcagt gagctgagat tgcgccactg cactccagcc tgggtgacaa    56100
gagctgacac tctgtctcaa aaaaaaaaaa aaaaaaaaaa aattcttaca gtgtgtgagt    56160
atccaggctg agtcctgaac acagctcttg ataaatgata acaagcaggc acaaaaaaat    56220
tgtagtacag gagtctgagg tcacttagca aagggacata aagttcaaac agctcagcag    56280
ctgctgaggg tcccgtgtta cattgtagca tttgttgttg tgactgggct agaaagaagg    56340
tgaagaaggt tggagctcac tccctgcctc ccctcccact ctcctcccctt tgacctacac    56400 tcatagttca cgcagcactc tgatgtgtcc ccttaggcca tcctctagtc aatgctgtgg    56460
gtaggctgga ccagcaggga ccagtattgt cacagcaagt ccaggccaac agtggtcagg    56520
ctgctgcccg tgttgtgcc tttgtgagtg gcagatccaa gaccggaacc caggccttct    56580
gagtcccagg ccaatgcttg ccccacccag catccaagat gttgctcact aaagagacag    56640
agaagcagcc ttattatggg cctggacacc tgtgcatgag gggtcaagca gagaggacct    56700
```

```
ggggagagac cctgcccctt cttttccttc tccttcctct cctttctctt cttcttcctc   56760
ttcaaatagc ttttttgaggt gtaactggca tacaatcaat tgtacatatt taggctgggt   56820
atggtggctc acgcctgtaa tcccagcact ttgggaggcc aaggcgggtg gatcacttga   56880
ggtcaggagt ttgagaccag cctgggcaac ccggtgaaac cccgtctcca ctaaaactac   56940
aaaaattagc caggcgtggt ggcagctgcc tgtaatcccg gctactcggg aggctgaggc   57000
aggagaatca cttgaacctg ggaagcgaag tttgcagtga tctgagatca tgccactgca   57060
ctccagcctg ggtgacagag cgagactttg cctcaaaaac aaaacaaaac aattgtacat   57120
atttaaagtg ttgtaaccaa gtgagttaca gagaaacacc acactttgag cctaattcag   57180
gagtcccttta ttagccggcg acctagagac gactagtgct caaaattctc tcggccccaa   57240
agaaggggct agattttctt ttataccttg gtttagaaag ggggaggggga attgagctga   57300
agcaatctta cagaagtaaa acaggcaaaa aagttaaaaa gacaaatggt tacaggaaaa   57360
caaacagttc caggtgcagg agctttaaag ccatcacaag gtgacaggtg cgggggctct   57420
gggtgctatc tgccggacac aaacgcaggg gcactagagt actatcaccc gggcaaattc   57480
ctgggaactg cggacacagc ttgccacagt accttatcag ctaattgcac tctttgatgt   57540
gctgggagtc agcttgcaca agttaagtcc ttgaggaagg gggtgggtaa ggagcccttta  57600
acgtcttgca aatgaaggag ccgaatggaa tccctccggc tttcttagct aagagagagt   57660
caatcaagtt aatacaagtt agggtatcac aaaagtatat aatttgatac attttaacgt   57720
atttatacac tgaagagacc atcaccacca tcaagacaag gagcacaccc atcacttcca   57780
cacacttcct cctgctcctt tgaaattcct cccttcctac ccacctggtc ccacccaaag   57840
gcaaccactg aactactttc tgtcactaag gtttgcgttt tctgtaattt ttttgtttga   57900
gacagggtct cactccgcca cccacaccgt aatgcagtgg caccatcatg actcactgta   57960
gcctcaacct ccccaggctc aggagatcct ccccctcag cctcctgagt agctaggacc   58020
acaggtgtag gccaccatgg caggctaatt tttgtatttt tttgtagaga tggggtttca   58080
ccgtattacc taggctggtc tcgaactcat gggttcaagc aatcctcctg ccttggcctc   58140
tcaaagtgct gggattatag gcatgagcca ctgtgcccag ccctctgtaa tgttacacaa   58200
agggaatcat gcagcacgta ctgcccttgg tctggcctct tttgctcagc atgattattc   58260
tgagaatcat ccgtgttgtt gcgtgtaact gacttcatca gcttctctct gcagctgtca   58320
gctcttggct tctcccaaca gccaatctct ctttatcccc tgcaagtgtt cttgcctatt   58380
tagcagaatc aaggtactct atcgaaaaga ctcggaaaat tggtttaatc tattcattca   58440
ttcctcaggt atttatcgaa taactattct ataccaagta ctatgctaat caaccaagga   58500
cagcacaaac aggagaaatc tccagctcag tcacttgagt tgcaataaat atttgctgga   58560
taggtcaggt gcagtggctc acacttgtaa tcccagcact ttggggatta ctgagacggg   58620
aggatctctt gagcccagga ggccaaggct gcagagaacc atgatcatgc cactgcactc   58680
cagcctgggt gacagagtga gatcctgtct ctgaaaaaaa atatttgctg gataaattaa   58740
ggaaatctga cgaaccccat cagtagccat tgcagcaaca ggtaaactag aacgagtgtg   58800
aatttggaat gaggaaaccc gatgttggcc atcattctgt aatgtcatgt attatgtaat   58860
gtattatata ttaatgtatg tattatgtag gcaagttcct tgacctctct cactggtaac   58920
ataagagtag taatctttgt gctacttcac tgggttattt caaagatcaa gtgaggtaat   58980
aatgtctgta acaacattct gtaaaatgca aaccgccaca tgaatgtgaa agtttattac   59040
tagggatttta gccaaccaca agggaatgtg tgagcataag agctatcata ttgcaagcct   59100
```

```
acagtttctg attttgtgct aggtgctttt ccacattacc tgattttatc ctcacaacag   59160
tcctgcataa aagtaagtat gtcgcccagg tgcggtggct catgcctata atcccagcac   59220
tttgggagcc cgaggtgggc aaatcacttg agatcaggag tttgaaacca gcctggtcaa   59280
cgtggtgcaa ccctgtctct actaaaaata caaaaaaaaa ttagacaggc gtggtggtgg   59340
atgcctgtaa tcccagctac ttgggaagct gaggcaggag aatggcttga gcccgggaga   59400
tggagattgc agtgagatga gattgcgcca ctgcactcca gcctgggtga cagagcaagg   59460
ctatgtctca aaagagaaaa aaaagtaag tatctcagtc ttgaagatga tgaaatggag   59520
gcctagagag attaagtaac ttgcccaaaa tgacagaact aatgcataga aagaagaaa   59580 tgtgatgtct tttggctcca aagacacccc acatatgcgt tggttacagt tactagagaa   59640
aagttattcc accccacccc acccccagaa atcttctga cttgttttct cgcagttgag   59700
taggaccatt tattcggcag tgtaccattc tcagcttgca gttgaaagcc aaatatccat   59760
taaagaggca aggatgcaaa cttgctaagc tgataaatcc aggggtgatt tttttttttt   59820
ttgcaaacca tccaacaaga cattttaaat actcattgaa tttcatagaa ctgactgcca   59880
ggattggaaa gacattaaag ccagctcagc cactgcctcg ctggttggcc agaccacgcc   59940
tggcacttct ggggggagc actcaccacc ccccaagggc acccatctca tcctccgaag   60000
gtttatgaaa atgcactcat catttgctaa ttcattccac tacgtgtatt acctaatttg   60060
tgacacgatg tgaagtacca gagagataat tctaaataaa atatagttat gggtctcaag   60120
gagccagata tgctaatctc ctatcctcct gcagtttaca gtggtcctca ccagatactt   60180
atttacaaaa attcagttta ttatttattt ttttgagaca gagtcttgct ctatagctca   60240
ggctagagtg taatggtgtg atctcggctc acttcaacct ctgcctccca ggttcaagtg   60300
attctcctgc ctcaacctcc caagtagctg ggactacagg cacctgccac cacggctaat   60360
ttttggagtt ttagtagaga cagggtttca ccacgttggc caggctggcc tcgaactcct   60420
gacctcaggt gatctgccca catcagcctc ccaaaatgtt gggattacag gcgtgagcca   60480
ccatgcccgg ccaaaacttc agtttataac acaatctttc acgtgtcttc tgctttcatt   60540
aaaagaatag acagttccct tctttatttc agtttaataa accatggatt ttatttcatg   60600
ctttgcaaaa cacaagggct cactgacatg cacttcttaa actaattctg ctggtcgcc   60660 tgtaattcca gcactttggg aggctgaggc cgacagatca cttcaagtca ggagttcaag   60720
accagcctgg ccaatatggt gaaaccacgt ctctaccaaa aatataaaaa attagccagg   60780
tgtggtggtg cgtgactata atcccagcta ctcaggggcc tgaggcagaa aaatcacttg   60840
aacccgggag gcggaggtta cagtgagctg agatcgcgcc actgcactcc agcctgggcg   60900
acagagtgag actctgtctc aaaaaataaa taaatacaaa taatgtaaaa tacgaaacaa   60960
gcaatcctgg cagtagctgc tggaatgaga ggagggagag gtcatagga ggtcggggac   61020 aatggagcat ggagttgtgt tggatttggc taagcagcag gaagtgcaag gcattccaag   61080
caagaggagg ggggcaggtg gggagcatct gcaagaacag aagcagcatg agcaacctgg   61140
ctcggcagtg tgtgaaaagg ctgaaaggtg gctagagcca cttcaatttc atccttcagg   61200
caaatgggaa attcccaaag gtttgagtgg ggaagcaatg cctacaatga agtttgaga   61260 gtgaagcaga gtgatcgaat taagcatgta ggccgagttc tgaaataact gcaatgtgct   61320
gaagatcatc cattggcttc tgaatgagta tttgcagttt atttttttaaa atgattttat   61380 tgccaagaaa gataaacact actgttttgg tacaaaaaca taacaaaatg tgttgagtcc   61440
```

```
ctcttgctgt tttacgcgaa gttttaaaaa tctactcttg tcacagtggt atcacccta    61500
cttctgattt caaataaatg ttctagagac acagtaaggg cccaacaaac gcttgttcaa   61560
caacacaagg agagccagct tttaaagtag gaaaacaggc cgggcgccgt ggctcacacc   61620
tgtaatccca cactttggg  aggctgaggt gggcagatca cttgaggtca ggagttcaag   61680
aacagcttgg ccaacatggt gaaaccctgt ctctactaaa aacacaaaca ttagccaggc   61740
gtggtggtgc acaccagtag tcccagctat tcaggaggct gaggcaggaa aatggcttga   61800
actggggagg cagtggttgc agtgagccga gatcgtgcca ctgcactcca gcctggggga   61860
cagagggaga ctccatctca aaataaaaca aaacaaaacc aaatcataca aaaacattag   61920
ctgggtgtgg tggtgcatac ctgtaatccc agctacttgg gaagctgagg cagaattact   61980
tgaaccctg  gggggaggtt gcagtgagct gagatcttgc cactacactc cagcctgggc   62040
aacagagtga ggagactctg tctcaaaaaa tatatatatt aaaaaaaga aaaaaaaag    62100
taaactagga aaacacatca gcagcctgcc aacagactcc cctagcctcg gtgagggcca   62160
gtgttctggg aggcagatct gaattctagt cctagttcac ccactggcag gctggtgccc   62220
ttgggcaggt cgcttctctg gggctcagtt tcttcctcta taaatgagaa tcaaatccca   62280
tgttctaaga gtttgtgctc tggagtcaga cagatctggg ttctaccact gccagctctg   62340
tgatcttgta gcttcagtct cgtcatctga catggagata acagtaactg tctcactgtg   62400
ttgttagggt ttaaggaga  taatgtatgt gaaatgttag caaacaagtg ttagctaccc   62460
tgatttccgg tttcagagtt ctgtggtccc agtttatgcc acatgcagtg acgttgtatg   62520
gtaggctgtg gtgtggcacc acttcagaac tcagcgcatg cacagcttgc agaagagaag   62580
gccagaggag acctaagaag gctcttcgaa cacttgaaag accggcatgt aggccgggcg   62640
cagtgactca cgcctgtaat cccagcagtt ttggaggtcg aggcgggtgg atcacctgag   62700
tttgggagtt tgataccagc ctgaccaaca aggtgaaacc ccgtctctac taaaaaatac   62760
aaacattagc tgggcatggt ggcgggtgcc tgtaatccca gctactccgg tggttgaggc   62820
agaattgctt gaacccggga ggcagaggtt gcagtgagct gagattgcat cactgcactc   62880
cagcctgaga caagagcgaa actccatctc aaacaaaaca aacaaccaac caaacaaaac   62940
caaaaaaaaa actggcatgt agaagaaaaa tacttttct  ctacacttct ccaaagaatt   63000
taactaggcc caggggaggt gcagtataaa tttctaacaa tctcaactgt ctgccaaatg   63060
gaatgagcta cttcatatgg cagtagtgag tcctctgtct ttggaggcat tcaaataaaa   63120
gccagatggc catttatcaa caatccatgt aaaacgttag atgaaataaa acctatatat   63180
ccaagatctc ttccaattca gattttatga aagaatttct aaggtctttg taatgagaca   63240
tttaggctgt ttcaagagat caagccaaaa tcagtatgtg ggttcatctg caataaaaat   63300
gtttgttttg cttttacagt ttcctcattt ggctgttgga ttttaagcaa aagcatccaa   63360
gaaaaacaag gcctgttcaa aaacaagaca acttcctctc actgttgcct gcatttgtac   63420
gtgagaaacg ctcatgacag caaagtctcc ttatgtataa tgaaacaagg tcagagcag   63480
atttgatatt aaaaaattaa agactaaaaa cttagtttaa gagtcaattt aataagttta   63540
aaataaatgt ttagtttcat taggatgatg ctatcaatat tttcttggtt acagacacat   63600
tattaaagtt ttgggttaat tttattgaca attcttaaga ttctttctca tgcttaataa   63660
agcatgctac tcagttaact cttgtctaca tcagcaaagc agataataca aaacaggaaa   63720
attacaaatc actgatactt agtccttgtg ggaatcatgc ttttctccca gcagttttac   63780
aaggtggctg gcattccctg agcatattct gaattgcact gtggggaaag aggttgtgct   63840
```

```
cagttgtagg gtgggggat  gcactgcctg  aggattaaaa aactagttct  gtgaccgtga  63900
ggaagtcgtt taaatttcca  tggtctgttc  cctcctatgt gaaaagagaa  ggtgggcttc  63960
aacctctaag atcttctcca  gttttcacat  tttatggact tttgtagaaa  aaacatcagg  64020
agttcatgtg ggatgacagc  aagtcatttc  tttgaggaga gtcttgatca  ccaggcaata  64080
ttcacagtgt agagactgtc  agatgaccat  ggctagcatg gaaatgagac  ccacacattt  64140
aaatcaccca gcaaatattc  cgaaggctaa  ttgtagcaca ttttatgaaa  gacatttcaa  64200
actgtggtcc tgaagagtgt  atcccatctt  gcagaggtgg ggagcctggg  gggacaagag  64260
ttctgaagag gaagagacaa  caagagttcc  cagtagctaa tgtttgtcat  tctagttgac  64320
cgtgctggtc tattaggcta  gtggttcagt  acacagatga aatgcaacat  ggaacccagt  64380
ttattatcag aacaactaca  aagaaattgt  ccctgtcta  agactggagt  gtcaagtctc  64440
tgcccttttt tcctttcctt  caatggtgga  tgtggagtga ctgtgcatcc  caccagaacc  64500
acgtgtcatg gctgagtcac  atcttcctgc  ccttggaatg agaggcacag  cggaagacct  64560
tcccatggaa gggacacagg  gagcctggtg  gctggaccat ggtgcttctc  tcttccaaca  64620
cgtccactca cccctttggga  gaccctcaaa  agccagttac attacatgtt  cacagaattt  64680
ttggtaaaag taaataccaa  ttatagtgag  gaagaatttt gaccacggaa  tatttaaaa   64740
actaaaaaat gtttatattt  catttaacat  ttgacacaga agagaccaca  tttgaataaa  64800
cacattaaat cttcagagca  cttcattgt   ggttttggac ctcagatatg  acaaatactt  64860
acattgacaa atccataatt  tcttttgtaa  tttcttttta  ttttacaaa  ttataccatg  64920
ataaatttg  acaaaatta   ttcatgtgaa  agtttcctct aacatttat   aagttaatca  64980
agtgcatacc acaatagatt  tttggttgtt  gtttaggtgt tctcgtgatt  ttagtattac  65040
acaactttaa gctgagacta  cactcagaaa  taagtttaga aatggcatt   acaaaaggtt  65100
gggagtgagc agtaaaaaaa  caaacaaacc  catgcagggc tgttgtgctg  tgggaaatca  65160
gatgtgttca ctgccataag  tcttcagtgc  ggccaaactt aaaaaccagc  cctctgtgaa  65220
taaaacaaga aatatcacat  gactccctga  atttgagaaa agagtatgtg  agatttcgag  65280
aatggtgtga aacaaacaac  gaagaataat  tgatgagttg tagaagaaat  tttggtacga  65340
aatgtatcaa aacagaaact  gatcattcta  aggtagtgaa ttcttccatt  atgttcaact  65400
gtgctattaa ccaccatatt  cccaacaacc  ttaactttca agtactgaat  acacatgtga  65460
cttttaaaaa gttaccagtg  tttactatgt  aaccattata tgtctgattt  ttttttttt   65520
ttttgagaca gagtcttgct  ctgtcgccca  ggctggagtg cagtggcgtg  atctcggctc  65580
actgcaagct ctgcctcccg  ggttcatgcc  attctcctgc ctct                    65624
```

<210> SEQ ID NO 24
<211> LENGTH: 27
<212> TYPE: DNA
<213> ORGANISM: Artificial sequence
<220> FEATURE:
<223> OTHER INFORMATION: Synthetic sequence: Probe

<400> SEQUENCE: 24
caaaagctga tatgtcatgt ttagtta                                         27

<210> SEQ ID NO 25
<211> LENGTH: 25
<212> TYPE: DNA
<213> ORGANISM: Artificial sequence
<220> FEATURE:

<223> OTHER INFORMATION: Synthetic sequence: Primer

<400> SEQUENCE: 25
gcaaatatgg aaatttgatc atgta                                     25

<210> SEQ ID NO 26
<211> LENGTH: 31
<212> TYPE: DNA
<213> ORGANISM: Artificial sequence
<220> FEATURE:
<223> OTHER INFORMATION: Synthetic sequence: Primer

<400> SEQUENCE: 26
cttaatcaca agattatttt cagaatctaa c                              31

<210> SEQ ID NO 27
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 27
gggccttgga caagttgtta                                           20

<210> SEQ ID NO 28
<211> LENGTH: 26
<212> TYPE: DNA
<213> ORGANISM: Artificial sequence
<220> FEATURE:
<223> OTHER INFORMATION: Synthetic sequence: Primer

<400> SEQUENCE: 28
ggcaaatatg gaaatttgat catgta                                    26

<210> SEQ ID NO 29
<211> LENGTH: 250
<212> TYPE: DNA
<213> ORGANISM: Homo sapiens

<400> SEQUENCE: 29
ttattcccaa ggcaaatatg gaaatttgat catgtactaa tcataataaa gctggattct    60
ctttaagaga ttgagaaatt aaaaggcaaa agctgatata tcatgtttag ttatattgtg   120
agtcttataa gaagctggga ggcaaccccca ttaactcacc agaatacaga actcagtctc   180
acaacttaga tataattcct ctcaaacctt ttcctcaaag attaaattct gaaataatc    240 ttgtgattaa                                                         250

<210> SEQ ID NO 30
<211> LENGTH: 249
<212> TYPE: DNA
<213> ORGANISM: Homo sapiens

<400> SEQUENCE: 30
ttattcccaa ggcaaatatg gaagtttgat catatgctaa tcatactaaa gctggattct    60
ctttaagaga ttgagaaatt aaaaggcaaa agctgatata tcatgtttag ttatactgtg   120
agtcttataa gaagctggga ggcaaccccca ttaactcacc agaatacaga actcagtctc   180
acaacttaaa tataattcct ctcaaacctt ttcctcaaag ttaaattctg aaataatct    240 tgtgattaa                                                          249

```
<210> SEQ ID NO 31
<211> LENGTH: 249
<212> TYPE: DNA
<213> ORGANISM: Homo sapiens

<400> SEQUENCE: 31
ttattcccaa ggcaaatatg gaaatttgat catgtactaa tcatactaaa gctggattct      60
ctttaagaga ttgagaaatt aaaaggcaaa agctgatatg tcatgtttag ttatattgtg     120
agtcttataa gaagctggga ggcaaccccca ttaactcacc agaatacaga actcagtctc    180
acaacttaaa tataattcct ctcaaacctt ttcctcaaag ttaaattctg aaaataatct     240
tgtgattaa                                                            249

<210> SEQ ID NO 32
<211> LENGTH: 250
<212> TYPE: DNA
<213> ORGANISM: Homo sapiens

<400> SEQUENCE: 32
ttattcccaa ggcaaatatg gaaatttgat catgtactaa tcataataaa gctggattct     60
ctttaagaga ttgagaaatt aaaaggcaaa agctgatatg tcatgtttag ttatattgtg    120
agtcttataa gaagctggga ggcaaccccca ttaactcacc agaatacaga actcagtctc   180
acaacttaga tataattcct ctcaaacctt ttcctcaaag attaaattct gaaaataatc    240
ttgtgattaa                                                          250
```